(12) United States Patent
Miller et al.

(10) Patent No.: US 7,947,665 B2
(45) Date of Patent: May 24, 2011

(54) LPA RECEPTOR AGONISTS AND ANTAGONISTS AND METHODS OF USE

(76) Inventors: Duane D. Miller, Germantown, TN (US); Gabor Tigyi, Memphis, TN (US); Gangadhar G. Durgam, Memphis, TN (US); Tamas Virag, Chicago, IL (US); Michelle D. Walker, Memphis, TN (US); Ryoko Tsukahara, Memphis, TN (US)

( * ) Notice: Subject to any disclaimer, the term of this patent is extended or adjusted under 35 U.S.C. 154(b) by 51 days.

(21) Appl. No.: 11/748,331

(22) Filed: May 14, 2007

(65) Prior Publication Data

US 2008/0090783 A1 Apr. 17, 2008

Related U.S. Application Data

(63) Continuation of application No. 10/963,085, filed on Oct. 12, 2004, now Pat. No. 7,217,704.

(60) Provisional application No. 60/509,971, filed on Oct. 9, 2003.

(51) Int. Cl.
*A61K 31/675* (2006.01)

(52) U.S. Cl. .......... 514/94; 514/114; 514/119; 514/120; 514/143

(58) Field of Classification Search .............. 514/94, 514/114, 119, 120, 143
See application file for complete search history.

(56) References Cited

U.S. PATENT DOCUMENTS

| 5,565,439 | A | * | 10/1996 | Piazza et al. | 514/110 |
| 6,495,532 | B1 | * | 12/2002 | Bathurst et al. | 514/110 |
| 6,949,529 | B2 | * | 9/2005 | Bathurst et al. | 514/110 |

OTHER PUBLICATIONS

Guest et al. (Experimental Hematology, 29 (2001); p. 123-137).*
Deng et al. (Gastroenterology, 2002 (123); p. 206-216).*

* cited by examiner

*Primary Examiner* — Yong Chu
*Assistant Examiner* — Valerie Rodriguez-Garcia
(74) *Attorney, Agent, or Firm* — Donna J. Russell

(57) ABSTRACT

Disclosed are compounds according to formula (I) as well as pharmaceutical compositions which include those compounds. Also disclosed are methods of using such compounds, which have activity as agonists or as antagonists of LPA receptors; such methods including inhibiting LPA activity on an LPA receptor, modulating LPA receptor activity, treating cancer, enhancing cell proliferation, treating a wound, treating apoptosis or preserving or restoring function in a cell, tissue, or organ, culturing cells, preserving organ or tissue function, and treating a dermatological condition.

7 Claims, 6 Drawing Sheets

Scheme 1[a]
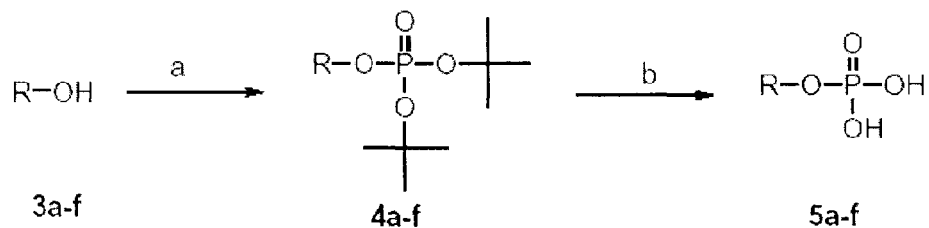
Scheme 2[a]
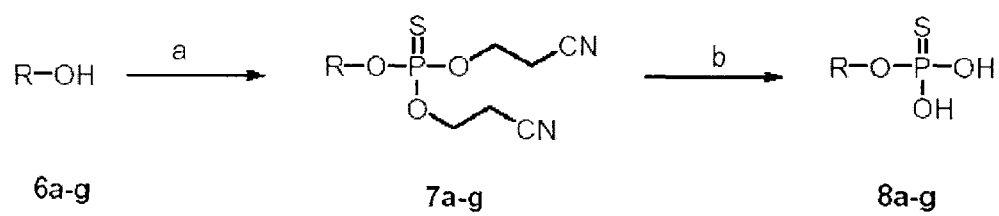
Scheme 3[a]
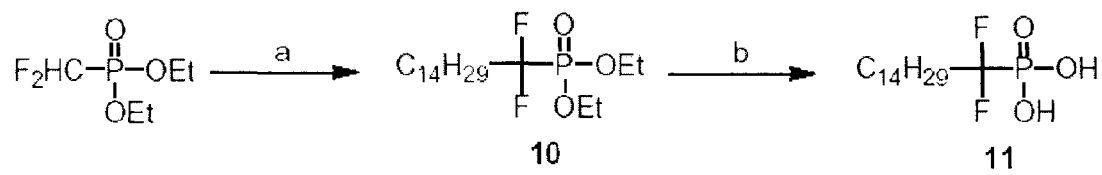
Figure 1

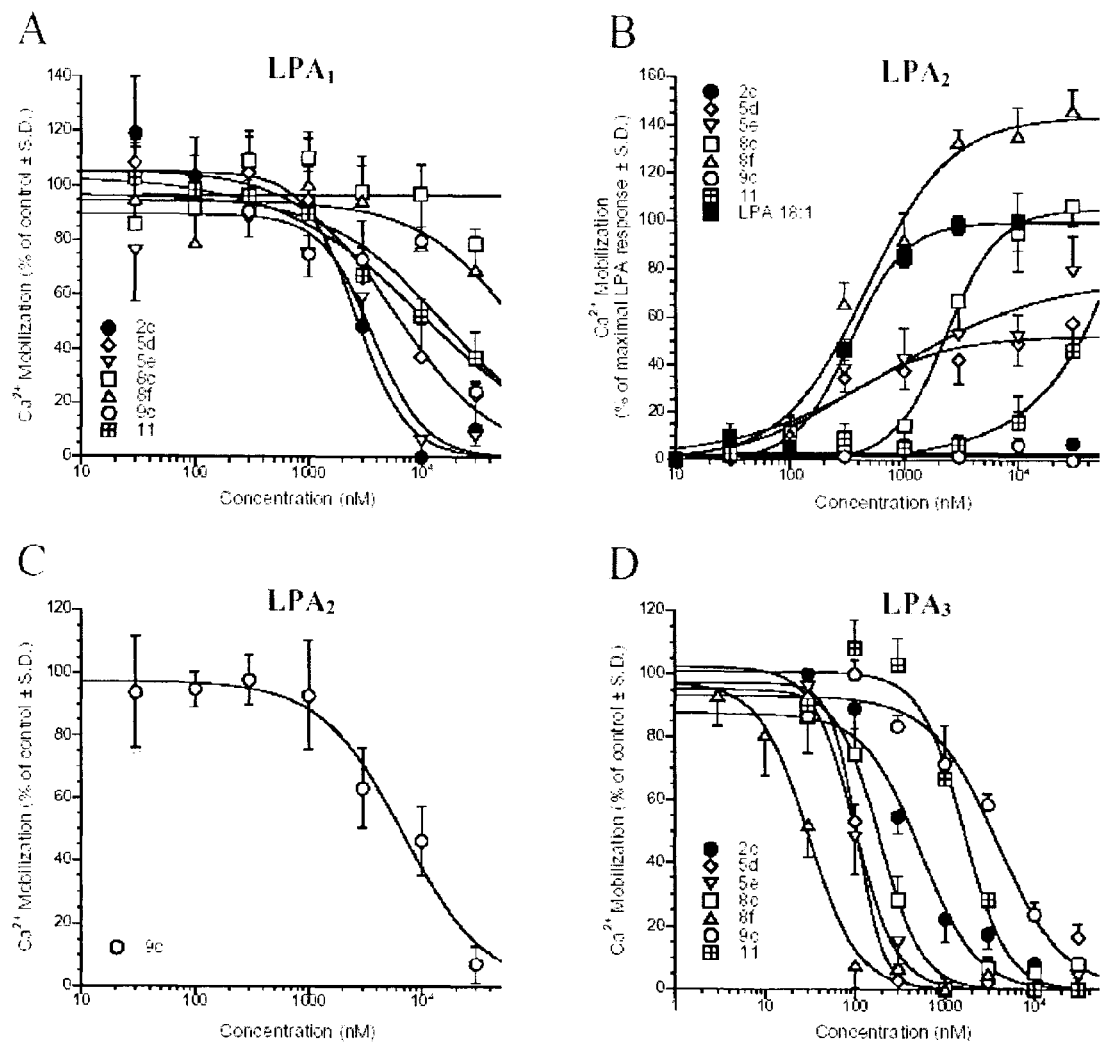
Figures 2A-D

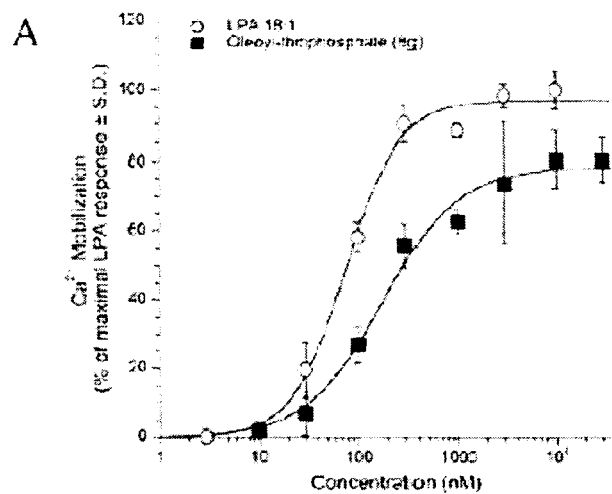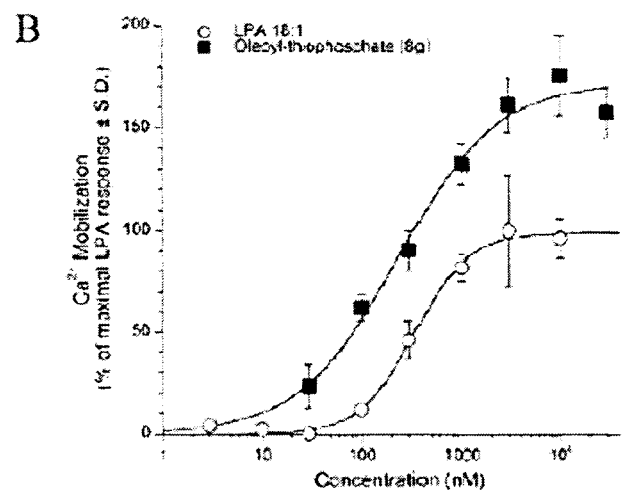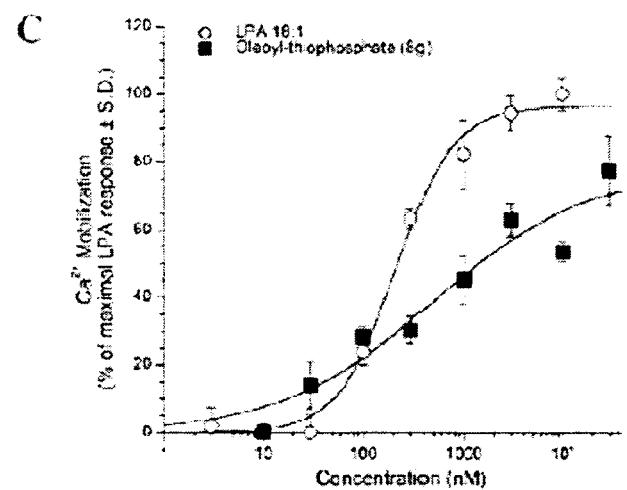
Figures 3A-C

SEQUENCE LISTING

```
<160> NUMBER OF SEQ ID NOS: 8

<210> SEQ ID NO 1
<211> LENGTH: 1095
<212> TYPE: DNA
<213> ORGANISM: Homo sapiens
<220> FEATURE:
<221> NAME/KEY: mRNA
<222> LOCATION: (1)..(1095)
<220> FEATURE:
<221> NAME/KEY: mRNA
<222> LOCATION: (1)..(1095)
<223> OTHER INFORMATION: Human lysophosphatidic acid receptor-1 homolog
      mRNA
<300> PUBLICATION INFORMATION:
<308> DATABASE ACCESSION NUMBER: Genbank/U80811
<309> DATABASE ENTRY DATE: 1996-12-02
```

<313> RELEVANT RESIDUES: (1)..(1095)

<400> SEQUENCE: 1

```
atggctgcca tctctacttc catccctgta atttcacagc cccagttcac agccatgaat    60
gaaccacagt gcttctacaa cgagtccatt gccttctttt ataaccgaag tggaaagcat   120
cttgccacag aatggaacac agtcagcaag ctggtgatgg acttggaat cactgtttgt    180
atcttcatca tgttggccaa cctattggtc atggtggcaa tctatgtcaa ccgccgcttc   240
catttcccta tttattacct aatggctaat ctggctgctg cagacttctt tgctgggttg   300
gcctacttct atctcatgtt caacacagga cccaatactc ggagactgac tgttagcaca   360
tggctcctgc gtcagggcct cattgacacc agcctgacgg catctgtggc caacttactg   420
gctattgcaa tcgagaggca cattacggtt ttccgcatgc agctccacac acggatgagc   480
aaccggcggg tagtggtggt cattgtggtc atctggacta tggccatcgt tatgggtgct   540
atcccagtg tgggctggaa ctgtatctgt gatattgaaa attgttccaa catggcaccc   600
ctctacagtg actcttactt agtcttctgg gccatttca acttggtgac ctttgtggta   660
atggtggttc tctatgctca catctttggc tatgttcgcc agaggactat gagaatgtct   720
cggcatagtt ctgtaccccg gcggaatcgg gataccatga tgagtcttct gaagactgtg   780
gtcattgtgc ttggggcctt tatcatctgc tggactcctg gattggtttt gttacttcta   840
gacgtgtgct gtccacagtg cgacgtgctg gcctatgaga aattcttcct tctccttgct   900
gaattcaact ctgccatgaa ccccatcatt tactcctacc gcgacaaaga aatgagcgcc   960
accttaggc agatcctctg ctgccagcgc agtgagaacc ccaccggccc cacagaaagc  1020
tcagaccgct cggcttccct cctcaaccac accatcttgg ctggagttca cagcaatgac  1080
cactctgtgg tttag                                                   1095
```

<210> SEQ ID NO 2
<211> LENGTH: 364
<212> TYPE: PRT
<213> ORGANISM: Homo sapiens
<300> PUBLICATION INFORMATION:
<308> DATABASE ACCESSION NUMBER: GenBank/U80811
<309> DATABASE ENTRY DATE: 1996-12-02
<313> RELEVANT RESIDUES: (1)..(364)

<400> SEQUENCE: 2

```
Met Ala Ala Ile Ser Thr Ser Ile Pro Val Ile Ser Gln Pro Gln Phe
1               5                   10                  15

Thr Ala Met Asn Glu Pro Gln Cys Phe Tyr Asn Glu Ser Ile Ala Phe
            20                  25                  30

Phe Tyr Asn Arg Ser Gly Lys His Leu Ala Thr Glu Trp Asn Thr Val
        35                  40                  45

Ser Lys Leu Val Met Gly Leu Gly Ile Thr Val Cys Ile Phe Ile Met
    50                  55                  60

Leu Ala Asn Leu Leu Val Met Val Ala Ile Tyr Val Asn Arg Arg Phe
65                  70                  75                  80

His Phe Pro Ile Tyr Tyr Leu Met Ala Asn Leu Ala Ala Ala Asp Phe
                85                  90                  95

Phe Ala Gly Leu Ala Tyr Phe Tyr Leu Met Phe Asn Thr Gly Pro Asn
            100                 105                 110

Thr Arg Arg Leu Thr Val Ser Thr Trp Leu Leu Arg Gln Gly Leu Ile
        115                 120                 125

Asp Thr Ser Leu Thr Ala Ser Val Ala Asn Leu Leu Ala Ile Ala Ile
    130                 135                 140
```

Glu Arg His Ile Thr Val Phe Arg Met Gln Leu His Thr Arg Met Ser
145                 150                 155                 160

Asn Arg Arg Val Val Val Ile Val Val Ile Trp Thr Met Ala Ile
            165                 170                 175

Val Met Gly Ala Ile Pro Ser Val Gly Trp Asn Cys Ile Cys Asp Ile
        180                 185                 190

Glu Asn Cys Ser Asn Met Ala Pro Leu Tyr Ser Asp Ser Tyr Leu Val
        195                 200                 205

Phe Trp Ala Ile Phe Asn Leu Val Thr Phe Val Val Met Val Val Leu
    210                 215                 220

Tyr Ala His Ile Phe Gly Tyr Val Arg Gln Arg Thr Met Arg Met Ser
225                 230                 235                 240

Arg His Ser Ser Gly Pro Arg Arg Asn Arg Asp Thr Met Met Ser Leu
                245                 250                 255

Leu Lys Thr Val Val Ile Val Leu Gly Ala Pro Ile Ile Cys Trp Thr
            260                 265                 270

Pro Gly Leu Val Leu Leu Leu Asp Val Cys Cys Pro Gln Cys Asp
        275                 280                 285

Val Leu Ala Tyr Glu Lys Phe Phe Leu Leu Leu Ala Glu Phe Asn Ser
    290                 295                 300

Ala Met Asn Pro Ile Ile Tyr Ser Tyr Arg Asp Lys Glu Met Ser Ala
305                 310                 315                 320

Thr Phe Arg Gln Ile Leu Cys Cys Gln Arg Ser Glu Asn Pro Thr Gly
                325                 330                 335

Pro Thr Glu Ser Ser Asp Arg Ser Ala Ser Ser Leu Asn His Thr Ile
                340                 345                 350

Leu Ala Gly Val His Ser Asn Asp His Ser Val Val
                355                 360

<210> SEQ ID NO 3
<211> LENGTH: 1056
<212> TYPE: DNA
<213> ORGANISM: Homo sapiens
<300> PUBLICATION INFORMATION:
<308> DATABASE ACCESSION NUMBER: GenBank/NM_004720
<309> DATABASE ENTRY DATE: 2000-10-30
<313> RELEVANT RESIDUES: (1)..(1056)

<400> SEQUENCE: 3
atggtcatca tgggccagtg ctactacaac gagaccatcg gcttcttcta taacaacagt    60
ggcaaagagc tcagctccca ctggcggccc aaggatgtgg tcgtggtggc actggggctg   120
accgtcagcg tgctggtgct gctgaccaat ctgctggtca tagcagccat cgcctccaac   180
cgccgcttcc accagcccat ctactacctg tcggcaatc tggccgcggc tgacctcttc   240
gcgggcgtgg cctacctctt cctcatgttc cacactggtc ccgcacagc ccgactttca   300 cttgagggct ggttcctgcg gcagggcttg ctggacacaa gctcactgc gtcggtggcc   360 acactgctgg ccatcgccgt ggagcggcac cgcagtgtga tggccgtgca gctgcacagc   420
cgcctgcccc gtggccgcgt ggtcatgctc attgtgggcg tgtgggtggc tgccctgggc   480
ctggggctgc tgcctgccca ctcctggcac tgcctctgtg ccctggaccg ctgctcacgc   540 atggcaccc tgctcagccg ctcctatttg ccgtctggg ctctgtcgag cctgcttgtc   600
ttcctgctca tggtggctgt gtacacccgc attttcttct acgtgcggcg gcgagtgcag   660
cgcatggcag agcatgtcag ctgccacccc cgctaccgag agaccacgct cagcctggtc   720
aagactgttg tcatcatcct ggggcgttc gtggtctgct ggacaccagg ccaggtggta   780

```
ctgctcctgg atggtttagg ctgtgagtcc tgcaatgtcc tggctgtaga aaagtacttc      840
ctactgttgg ccgaggccaa ctcactggtc aatgctgctg tgtactcttg ccagagatgct    900 gagatgcgcc gcaccttccg ccgccttctc tgctgcgcgt gcctccgcca gtccacccgc     960
gagtctgtcc actatacatc ctctgcccag ggaggtgcca gcactcgcat catgcttccc    1020
gagaacggcc acccactgat ggactccacc ctttag                              1056
```

<210> SEQ ID NO 4
<211> LENGTH: 351
<212> TYPE: PRT
<213> ORGANISM: Homo sapiens
<300> PUBLICATION INFORMATION:
<308> DATABASE ACCESSION NUMBER: GenBank/NM_004720
<309> DATABASE ENTRY DATE: 2000-10-30
<313> RELEVANT RESIDUES: (1)..(351)

<400> SEQUENCE: 4

```
Met Val Ile Met Gly Gln Cys Tyr Tyr Asn Glu Thr Ile Gly Phe Phe
1               5                   10                  15

Tyr Asn Asn Ser Gly Lys Glu Leu Ser Ser His Trp Arg Pro Lys Asp
            20                  25                  30

Val Val Val Ala Leu Gly Leu Thr Val Ser Val Leu Val Leu Leu
        35                  40                  45

Thr Asn Leu Leu Val Ile Ala Ala Ile Ala Ser Asn Arg Arg Phe His
    50                  55                  60

Gln Pro Ile Tyr Tyr Leu Leu Gly Asn Leu Ala Ala Ala Asp Leu Phe
65                  70                  75                  80

Ala Gly Val Ala Tyr Leu Phe Leu Met Phe His Thr Gly Pro Arg Thr
                85                  90                  95

Ala Arg Leu Ser Leu Glu Gly Trp Phe Leu Arg Gln Gly Leu Leu Asp
            100                 105                 110

Thr Ser Leu Thr Ala Ser Val Ala Thr Leu Leu Ala Ile Ala Val Glu
        115                 120                 125

Arg His Arg Ser Val Met Ala Val Gln Leu His Ser Arg Leu Pro Arg
    130                 135                 140

Gly Arg Val Val Met Leu Ile Val Gly Val Trp Val Ala Ala Leu Gly
145                 150                 155                 160

Leu Gly Leu Leu Pro Ala His Ser Trp His Cys Leu Cys Ala Leu Asp
                165                 170                 175

Arg Cys Ser Arg Met Ala Pro Leu Leu Ser Arg Ser Tyr Leu Ala Val
            180                 185                 190

Trp Ala Leu Ser Ser Leu Leu Val Phe Leu Leu Met Val Ala Val Tyr
        195                 200                 205

Thr Arg Ile Phe Phe Tyr Val Arg Arg Arg Val Gln Arg Met Ala Glu
    210                 215                 220

His Val Ser Cys His Pro Arg Tyr Arg Glu Thr Thr Leu Ser Leu Val
225                 230                 235                 240

Lys Thr Val Val Ile Ile Leu Gly Ala Phe Val Cys Trp Thr Pro
                245                 250                 255

Gly Gln Val Val Leu Leu Leu Asp Gly Leu Gly Cys Glu Ser Cys Asn
            260                 265                 270

Val Leu Ala Val Glu Lys Tyr Phe Leu Leu Leu Ala Glu Ala Asn Ser
        275                 280                 285

Leu Val Asn Ala Ala Val Tyr Ser Cys Arg Asp Ala Glu Met Arg Arg
    290                 295                 300
```

```
Thr Phe Arg Arg Leu Leu Cys Cys Ala Cys Leu Arg Gln Ser Thr Arg
305                 310                 315                 320

Glu Ser Val His Tyr Thr Ser Ser Ala Gln Gly Gly Ala Ser Thr Arg
                325                 330                 335

Ile Met Leu Pro Glu Asn Gly His Pro Leu Met Asp Ser Thr Leu
            340                 345                 350
```

<210> SEQ ID NO 5
<211> LENGTH: 1062
<212> TYPE: DNA
<213> ORGANISM: Homo sapiens
<300> PUBLICATION INFORMATION:
<308> DATABASE ACCESSION NUMBER: GenBank/NM_012152
<309> DATABASE ENTRY DATE: 1999-02-10
<313> RELEVANT RESIDUES: (1)..(1062)

<400> SEQUENCE: 5

```
atgaatgagt gtcactatga caagcacatg gacttttttt ataataggag caacactgat      60
actgtcgatg actggacagg aacaaagctt gtgattgttt tgtgtgttgg gacgtttttc     120
tgcctgttta ttttttttc taattctctg gtcatcgcgg cagtgatcaa aacagaaaa      180
tttcatttcc ccttctacta cctgttggct aatttagctg ctgccgattt cttcgctgga    240
attgcctatg tattcctgat gtttaacaca ggcccagttt caaaaacttt gactgtcaac    300
cgctggtttc tccgtcaggg gcttctggac agtagcttga ctgcttccct caccaacttg    360
ctggttatcg ccgtggagag gcacatgtca atcatgagga tgcgggtcca tagcaacctg    420
accaaaaaga gggtgacact gctcattttg cttgtctggg ccatcgccat ttttatgggg    480
gcggtcccca cactgggctg gaattgcctc tgcaacatct ctgcctgctc ttccctggcc    540
cccatttaca gcaggagtta ccttgttttc tggacagtgt ccaacctcat ggccttcctc    600
atcatggttg tggtgtacct gcggatctac gtgtacgtca agaggaaaac caacgtcttg    660
tctccgcata caagtgggtc catcagccgc cggaggacac ccatgaagct aatgaagacg    720
gtgatgactg tcttagggc gtttgtggta tgctggaccc cgggcctggt ggttctgctc    780
ctcgacggcc tgaactgcag cagtgtggc gtgcagcatg tgaaaaggtg gttcctgctg    840
ctggcgctgc tcaactccgt cgtgaacccc atcatctact cctacaagga cgaggacatg    900
tatggcacca tgaagaagat gatctgctgc ttctctcagg agaacccaga gaggcgtccc    960
tctcgcatcc cctccacagt cctcagcagg agtgacacag gcagccagta catagaggat   1020
agtattagcc aaggtgcagt ctgcaataaa gcacttcct aa                        1062
```

<210> SEQ ID NO 6
<211> LENGTH: 351
<212> TYPE: PRT
<213> ORGANISM: Homo sapiens
<300> PUBLICATION INFORMATION:
<308> DATABASE ACCESSION NUMBER: GenBank/NM_012152
<309> DATABASE ENTRY DATE: 1999-02-10
<313> RELEVANT RESIDUES: (1)..(351)

<400> SEQUENCE: 6

```
Met Asn Glu Cys His Tyr Asp Lys His Met Asp Phe Phe Tyr Asn Arg
1               5                   10                  15

Ser Asn Thr Asp Thr Val Asp Asp Trp Thr Gly Thr Lys Leu Val Ile
            20                  25                  30

Val Leu Cys Val Gly Thr Phe Phe Cys Leu Phe Ile Phe Phe Ser Asn
        35                  40                  45

Ser Leu Val Ile Ala Ala Val Ile Lys Asn Arg Lys Phe His Phe Pro
    50                  55                  60
```

```
Phe Tyr Tyr Leu Leu Ala Asn Leu Ala Ala Ala Asp Phe Phe Ala Gly
 65                  70                  75                  80

Ile Ala Tyr Val Phe Leu Met Phe Asn Thr Gly Pro Val Ser Lys Thr
                 85                  90                  95

Leu Thr Val Asn Arg Trp Phe Leu Arg Gln Gly Leu Leu Asp Ser Ser
            100                 105                 110

Leu Thr Ala Ser Leu Thr Asn Leu Leu Val Ile Ala Val Glu Arg His
        115                 120                 125

Met Ser Ile Met Arg Met Arg Val His Ser Asn Leu Thr Lys Lys Arg
130                 135                 140

Val Thr Leu Leu Ile Leu Leu Val Trp Ala Ile Ala Ile Phe Met Gly
145                 150                 155                 160

Ala Val Pro Thr Leu Gly Trp Asn Cys Leu Cys Asn Ile Ser Ala Cys
                165                 170                 175

Ser Ser Leu Ala Pro Ile Tyr Ser Arg Ser Tyr Leu Val Phe Trp Thr
            180                 185                 190

Val Ser Asn Leu Met Ala Phe Leu Ile Met Val Val Val Tyr Leu Arg
        195                 200                 205

Ile Tyr Val Tyr Val Lys Arg Lys Thr Asn Val Leu Ser Pro His Thr
210                 215                 220

Ser Gly Ser Ile Ser Arg Arg Arg Thr Pro Met Lys Leu Met Lys Thr
225                 230                 235                 240

Val Met Thr Val Leu Gly Ala Phe Val Val Cys Trp Thr Pro Gly Leu
                245                 250                 255

Val Val Leu Leu Leu Asp Gly Leu Asn Cys Arg Cys Gly Val Gln His
            260                 265                 270

Val Lys Arg Trp Phe Leu Leu Leu Ala Leu Leu Asn Ser Val Val Asn
        275                 280                 285

Pro Ile Ile Tyr Ser Tyr Lys Asp Glu Asp Met Tyr Gly Thr Met Lys
290                 295                 300

Lys Met Ile Cys Cys Phe Ser Gln Glu Pro Glu Arg Arg Pro Ser Arg
305                 310                 315                 320

Ile Pro Ser Thr Val Leu Ser Arg Ser Asp Thr Gly Ser Gln Tyr Ile
                325                 330                 335

Glu Asp Ser Glu Ser Gln Gly Ala Cys Cys Asn Lys Ser Thr Ser
            340                 345                 350

<210> SEQ ID NO 7
<211> LENGTH: 1260
<212> TYPE: DNA
<213> ORGANISM: Homo sapiens
<300> PUBLICATION INFORMATION:
<308> DATABASE ACCESSION NUMBER: GenBank/AB030566
<309> DATABASE ENTRY DATE: 1999-07-28
<313> RELEVANT RESIDUES: (1)..(1260)

<400> SEQUENCE: 7
atggtcttct cggcagtgtt gactgcgttc cataccggga catccaacac aacatttgtc      60
gtgtatgaaa acacctacat gaatattaca ctccctccac cattccagca tcctgacctc     120
agtccattgc ttagatatag ttttgaaacc atggctccca ctggtttgag ttccttgacc     180
gtgaatagta cagctgtgcc cacaacacca gcagcattta gagcctaaa cttgcctctt      240 cagatcaccc tttctgctat aatgatattc attctgtttg tgtcttttct tgggaacttg     300
gttgtttgcc tcatggttta ccaaaaagct gccatgaggt ctgcaattaa catcctcctt     360
gccagcctag cttttgcaga catgttgctt gcagtgctga acatgccctt tgccctggta     420
```

```
actattctta ctacccgatg gattttgggg aaattcttct gtagggtatc tgctatgttt      480
ttctggttat ttgtgataga aggagtagcc atcctgctca tcattagcat agataggttc      540
cttattatag tccagaggca ggataagcta aacccatata gagctaaggt tctgattgca      600
gtttcttggg caacttcctt ttgtgtagct tttcctttag ccgtaggaaa ccccgacctg      660
cagatacctt cccgagctcc ccagtgtgtg tttgggtaca caaccaatcc aggctaccag      720
gcttatgtga ttttgatttc tctcatttct ttcttcatac ccttcctggt aatactgtac      780
tcatttatgg gcatactcaa caccccttcgg cacaatgcct tgaggatcca tagctaccct      840
gaaggtatat gcctcagcca ggccagcaaa ctgggtctca tgagtctgca gagacctttc      900
cagatgagca ttgacatggg ctttaaaaca cgtgccttca ccactatttt gattctcttt      960
gctgtcttca ttgtctgctg ggccccattc accacttaca gccttgtggc aacattcagt     1020
aagcactttt actatcagca caactttttt gagattagca cctggctact gtggctctgc     1080
tacctcaagt ctgcattgaa tccgctgatc tactactgga ggattaagaa attccatgat     1140
gcttgcctgg acatgatgcc taagtccttc aagttttttgc cgcagctccc tggtcacaca     1200
aagcgacgga tacgtcctag tgctgtctat gtgtgtgggg aacatcggac ggtggtgtga     1260
```

<210> SEQ ID NO 8
<211> LENGTH: 419
<212> TYPE: PRT
<213> ORGANISM: Homo sapiens
<300> PUBLICATION INFORMATION:
<308> DATABASE ACCESSION NUMBER: GenBank/AB030566
<309> DATABASE ENTRY DATE: 1999-07-28
<313> RELEVANT RESIDUES: (1)..(419)

<400> SEQUENCE: 8

```
Met Val Phe Ser Ala Val Leu Thr Ala Phe His Thr Gly Thr Ser Asn
1               5                   10                  15

Thr Thr Phe Val Val Tyr Glu Asn Thr Tyr Met Asn Ile Thr Leu Pro
            20                  25                  30

Pro Pro Phe Gln His Pro Asp Leu Ser Pro Leu Leu Arg Tyr Ser Phe
        35                  40                  45

Glu Thr Met Ala Pro Thr Gly Leu Ser Ser Leu Thr Val Asn Ser Thr
    50                  55                  60

Ala Val Pro Thr Thr Pro Ala Ala Phe Lys Ser Leu Asn Leu Pro Leu
65                  70                  75                  80

Gln Ile Thr Leu Ser Ala Ile Met Ile Phe Ile Leu Phe Val Ser Phe
                85                  90                  95

Leu Gly Asn Leu Val Val Cys Leu Met Val Tyr Gln Lys Ala Ala Met
            100                 105                 110

Arg Ser Ala Ile Asn Ile Leu Leu Ala Ser Leu Ala Phe Ala Asp Met
        115                 120                 125

Leu Leu Ala Val Leu Asn Met Pro Phe Ala Leu Val Thr Ile Leu Thr
    130                 135                 140

Thr Arg Trp Ile Phe Gly Lys Phe Phe Cys Arg Val Ser Ala Met Phe
145                 150                 155                 160

Phe Trp Leu Phe Val Ile Glu Gly Val Ala Ile Leu Leu Ile Ile Ser
                165                 170                 175

Ile Asp Arg Phe Leu Ile Ile Val Gln Arg Gln Asp Lys Leu Asn Pro
            180                 185                 190

Tyr Arg Ala Lys Val Leu Ile Ala Val Ser Trp Ala Thr Ser Phe Cys
        195                 200                 205
```

```
Val Ala Phe Pro Leu Ala Val Gly Asn Pro Asp Leu Gln Ile Pro Ser
    210                 215                 220

Arg Ala Pro Gln Cys Val Phe Gly Tyr Thr Thr Asn Pro Gly Tyr Gln
225                 230                 235                 240

Ala Tyr Val Ile Leu Ile Ser Leu Ile Ser Phe Phe Ile Pro Phe Leu
                245                 250                 255

Val Ile Leu Tyr Ser Phe Met Gly Ile Leu Asn Thr Leu Arg His Asn
                260                 265                 270

Ala Leu Arg Ile His Ser Tyr Pro Glu Gly Ile Cys Leu Ser Gln Ala
            275                 280                 285

Ser Lys Leu Gly Leu Met Ser Leu Gln Arg Pro Phe Gln Met Ser Ile
        290                 295                 300

Asp Met Gly Phe Lys Thr Arg Ala Phe Thr Thr Ile Leu Ile Leu Phe
305                 310                 315                 320

Ala Val Phe Ile Val Cys Trp Ala Pro Phe Thr Thr Tyr Ser Leu Val
                325                 330                 335

Ala Thr Phe Ser Lys His Phe Tyr Tyr Gln His Asn Phe Phe Glu Ile
                340                 345                 350

Ser Thr Trp Leu Leu Trp Leu Cys Tyr Leu Lys Ser Ala Leu Asn Pro
        355                 360                 365

Leu Ile Tyr Tyr Trp Arg Ile Lys Lys Phe His Asp Ala Cys Leu Asp
370                 375                 380

Met Met Pro Lys Ser Phe Lys Phe Leu Pro Gln Leu Pro Gly His Thr
385                 390                 395                 400

Lys Arg Arg Ile Arg Pro Ser Ala Val Tyr Val Cys Gly Glu His Arg
                405                 410                 415

Thr Val Val
```

LPA RECEPTOR AGONISTS AND ANTAGONISTS AND METHODS OF USE

CROSS-REFERENCE TO RELATED APPLICATIONS

This application is a continuation application of and claims the priority benefit of U.S. patent application Ser. No. 10/963,085, filed Oct. 12, 2004, now U.S. Pat. No. 7,217,704, which claimed the benefit of priority of earlier-filed Provisional Patent Application Ser. No. 60/509,971, filed Oct. 9, 2003. The disclosures of both applications are incorporated herein by reference in their entirety.

STATEMENT OF GOVERNMENT RIGHTS

This invention was funded, in part, by the National Institutes of Health Grant No. CA92160. The U.S. government may have certain rights in this invention.

FIELD OF THE INVENTION

This invention relates to lysophosphatidic acid ("LPA") derivatives which have activity as either agonists or antagonists on LPA receptors and various therapeutic uses thereof including, but not limited to, prostate cancer therapy, ovarian cancer therapy, and wound healing.

BACKGROUND OF THE INVENTION

Non-transformed cells require growth factors for their survival and proliferation. In addition to polypeptide growth factors, an emerging class of lipids with growth factor-like properties has been discovered, collectively known as phospholipid growth factors (PLGFs). Although they have similar pharmacologic properties in inducing the proliferation of most quiescent cells (Jalink et al., 1994a; Tokumura, 1995; Moolenaar et al., 1997), PLGFs can be sub-divided structurally into two broad categories. The first category contains the glycerophospholipid mediators (GPMs), which possess a glycerol backbone. Exemplary GPMs include LPA, phosphatidic acid (PA), cyclic phosphatidic acid (cyclic-PA), alkenyl glycerol phosphate (alkenyl-GP), and lysophosphatidyl serine (LPS). The second category contains the sphingolipid mediators (SPMs), which possess a sphingoid base motif. Exemplary SPMs include sphingosine-1-phosphate (SPP), dihydrosphingosine-1-phosphate, sphingosylphosphorylcholine (SPC), and sphingosine (SPH).

LPA (Tigyi et al., 1991; Tigyi and Miledi, 1992), PA (Myher et al., 1989), alkenyl-GP (Liliom et al., 1998), cyclic-PA (Kobayashi et al., 1999), SPP (Yatomi et al., 1995), and SPC (Tigyi et al., 2000) have been detected in serum. These lipid mediators have been identified and characterized. There are still yet unknown PLGFs present in the serum and plasma that exhibit growth factor-like properties (Tigyi and Miledi, 1992). LPA, at a concentration of ≈20 μM, is the most abundant PLGF present in the serum (Tigyi and Miledi, 1992; Jalink et al., 1993).

In eukaryotic cells, LPA is a key intermediate in the early stages of phospholipid biosynthesis, which takes place predominantly in the membrane of endoplasmic reticulum (ER) (Bosch, 1974; Bishop and Bell, 1988). In the ER, LPA is derived from the action of Acyl-CoA on glycerol-3-phosphate, which is further acylated to yield PA. Because the rate of acylation of LPA to PA is very high, very little LPA accumulates at the site of biosynthesis (Bosch, 1974). Since LPA is restricted to the ER, its role as a metabolic intermediate is most probably unrelated to its role as a signaling molecule.

LPA is a constituent of serum and its levels are in the low micromolar (μM) range (Eicholtz et al., 1993). This level is expected because LPA is released by activated platelets during the coagulation process. Unlike serum, it is not detectable in fresh blood or plasma (Tigyi and Miledi, 1992; Eicholtz et al., 1993). LPA that is present in the serum is bound to albumin, and is responsible for a majority of the heat-stable, and non-dialysable biological activity of the whole serum (Moolenaar, 1994). The active serum component that is responsible for eliciting an inward chloride current in *Xenopus* oocyte was identified to be LPA (18:0) (Tigyi and Miledi, 1992). The bulk of the albumin-bound LPA (18:0) is produced during the coagulation process, rather than by the action of lysophospholipase D (PLD) on lyso-PC. The latter pathway is responsible for the presence of LPA in 'aged' plasma that has been de-coagulated by the action of heparin or citrate plus dextrose (Tokumura et al., 1986). Furthermore, LPA is not present in plasma that has been treated with EDTA. This fact implies that plasma lysophospholipase may be $Ca^{2+}$-dependent (Tokumura et al., 1986).

The role of albumin is to protect LPA from the actions of phospholipases present in the serum (Tigyi and Miledi, 1992). Tigyi and Miledi suggested that albumin not only acts as a carrier of LPA in the blood stream, but also increases its physiological half-life. There are yet unidentified lipid mediators present in serum albumin that mimic the actions of LPA in eliciting chloride current in *Xenopus* oocytes.

LPA-responsive cell types extend from those of slime mold amoebae and *Xenopus* oocyte to mammalian somatic cells. Thus, it seems likely that the source of LPA and its release may not be restricted only to activated platelets. Recent experiments showed that, on stimulation by peptide growth factors, mammalian fibroblasts rapidly produce LPA, which is followed by its release into the extracellular medium (Fukami and Takenawa, 1992).

There is evidence that relatively high amounts of bioactive LPA of unknown cellular origin are present in the ascitic fluid of ovarian cancer patients (Xu et al., 1995a), and that the ascitic fluid from such patients is known to possess potent mitogenic activity for ovarian carcinoma cells (Mills et al., 1988; Mills et al., 1990). It remains to be established whether it is secreted by tumor cells into the extracellular fluid, secreted by leukocytes, or produced from more complex lipids via the actions of various phospholipases.

GPMs and SPMs elicit a wide variety of cellular responses that span the phylogenetic tree (Jalink et al., 1993a). LPA induces transient $Ca^{2+}$ signals that originate from intracellular stores in a variety of cells such as neuronal (Jalink et al., 1993; Durieux et al., 1992), platelets, normal as well as transformed fibroblasts (Jalink et al., 1990), epithelial cells (van Corven et al., 1989; Moolenaar, 1991), and *Xenopus* oocytes (Tigyi and Miledi, 1992; Durieux et al., 1992; Fernhout et al., 1992). LPA induces platelet aggregation (Schumacher et al., 1979; Tokumura et al., 1981; Gerrard et al., 1979; Simon et al., 1982) and smooth muscle contraction (Tokumura et al., 1980; Tokumura et al., 1994), and upon intravenous administration it induces species-dependent changes in blood pressure ((Schumacher et al., 1979; Tokumura et al., 1978).

LPA, when added to quiescent fibroblasts, stimulates DNA synthesis and cell division (van Corven et al., 1989; van Corven et al., 1992). The growth-like effects of LPA do not require the presence of peptide growth factors. This observation makes LPA different from endothelin or vasopressin, which require the presence of insulin or epidermal growth factor (Moolenaar, 1991) to sustain cell proliferation. Notably, in Sp2 myeloma cells, LPA demonstrated an antimitogenic response, which was mediated by an increase in cAMP levels (Tigyi et al., 1994; Fischer et al., 1998). Unlike the mitogenic pathway, the anti-mitogenic pathway was not affected by pertussis toxin (PTX). Also, on addition of forskolin and isobutyl methyl xanthin, the antimitogenic actions of LPA in Sp myeloma cells were additive (Tigyi et al., 1994). In various cell types, LPA causes cytoskeletal changes, which include formation of focal adhesions and stress fibers in fibroblasts (Ridley and Hall, 1992). LPA also promotes the reversal and suppression of neuroblastoma differentiation by inducing the retraction of developing neurites (Jalink et al., 1994a; Jalink et al., 1994b). Addition of nanomolar (nmol) amounts of LPA (Jalink and Moolenaar, 1992) to serum-starved N1E-115 neuroblastoma cells caused immediate neurite retraction, which was accompanied by rapid, but transient, rounding of the cell body (Jalink et al., 1993b). When a continuous presence of LPA is provided, neuroblastoma cells maintain their undifferentiated phenotype, but fail to undergo mitosis (Jalink et al., 1993b). Additional factors, such as insulin-like growth factors, are required for the progression of the cell cycle. Once the cells have undergone morphological differentiation, the addition of LPA reverses this morphological change. Thus, LPA-induced neurite retractions result from the contraction of the actin-cytoskeleton, rather than from loss of adhesion to the substratum (Jalink et al., 1993b; Jalink et al., 1994b).

LPA, similar to other physiological chemoattractants (e.g., interleukin-8), induces cell migration by a haptotactic mechanism in human monocytes (Zhou et al., 1995). In addition to inducing cell migration, LPA promotes the invasion of hepatoma and carcinoma cells into the monolayer of mesothelial cells (Imamura et al., 1993). The mechanism that underlies this invasion is still unclear, but it may be due to enhanced cell motility and increased cell adhesion. Finally, LPA is also known to block neonatal cardiomyocyte apoptosis (Umansky et al., 1997).

A unique natural phospholipid, namely cyclic-PA, was shown to be responsible for cellular actions that were similar to or opposite to other GPMs, depending on the cell type. When tested on the *Xenopus* oocyte, it elicited chloride current just like other GPMs; but its response was not desensitized by LPA (Fischer et al., 1998). Murakami-Murofushi et al. (1993) showed that cyclic-PA exhibited antiproliferative actions, unlike LPA, which induces proliferation.

PLGF receptors (PLGFRs) belong to a seven-transmembrane (7 TM) guanine nucleotide-binding regulatory protein (G protein)-coupled receptors (GPCR) superfamily. Seven-TM GPCRs are a family of cell-surface receptors that mediate their cellular responses via interacting with the heterotrimeric G-protein. A number of LPA receptors have been identified including, among others, EDG-2, EDG-4, EDG-7, and PSP-24. A phylogenetic tree illustrating the relatedness of these LPA receptors and others is shown in FIG. 1.

In 1996, Hecht et al. used differential hybridization to clone a cDNA encoding a putative serpentine receptor from mouse neocortical cell lines (Hecht et al., 1996). The gene was termed as ventricular zone gene-1 (Vzg-1). The gene was expressed in cortical neurogenic regions and encoded a protein with a molecular weight of 41 kDa (364 amino acids). Vzg-1 was very similar to an unpublished sheep sequence termed endothelial differentiation gene-2 (EDG-2). The same cDNA was also isolated as an orphan receptor from mouse and bovine libraries, and was known as rec1.3 (Macrae et al., 1996). It was widely distributed in the mouse tissue, with the highest expression in the brain and heart.

In 1996, Guo et al., using a PCR base protocol, isolated another putative LPA receptor PSP-24 (372 amino acids) from *Xenopus* oocyte (Guo et al., 1996). This receptor showed little similarity with Vzg-1/EDG-2/rec1.3 (Guo et al., 1996). A sequence based search for sphingolipid receptors, using the cDNA sequence of the EDG-2 human LPA receptor, led to two closely related GPCRs, namely, rat H218 (EDG-5, 354 amino acids) and EDG-3 (378 amino acids) (An et al., 1997a). Northern analysis showed a high expression of mRNA that encoded EDG-3 and EGD-5 in heart tissue.

The recent identification of EDG-2 as a functional receptor for LPA prompted An et al. to perform a sequence-based search for a novel subtype of LPA receptor (An et al., 1998a). A human cDNA, encoding a GPCR, was discovered and designated EDG-4 (An et al., 1998a). Northern blot analysis showed that, although EDG-2 and EDG-4 both serve as GPM receptors, their tissue distributions were very different. Unlike EDG-2, EDG-4 was primarily expressed in peripheral blood leukocytes and testes (An et al., 1998a).

PCR amplification cDNA from human Jurkat T cells identified a previously unknown GPCR belonging to the EDG family. The identified GPCR was designated EDG-7. It has a molecular mass of 40 kDa (353 amino acids). Northern blot analysis of EDG-7 expression in human tissues showed that it is expressed in heart, pancreas, prostate, and testes (Bandoh et al., 1999). Thus, there are two distinct families of PLGF receptors PSP24 and EDG, with a total of ten individual PLGFRs (FIG. 1). The list continues to grow.

These various receptors can be classified based on their ligand specificities for GPMs or SPMs, as shown in Table 1 below.

TABLE 1

Phospholipid Growth Factor Receptor (PLGFR), Length and Principle Ligand

| PLGFR | Number of amino acids | Principle Ligand |
|---|---|---|
| EDG-1 | 381 | SPP |
| EDG-2 | 364 | LPA |
| EDG-3 | 378 | SPP |
| EDG-4 | 382 | LPA |
| EDG-5 | 354 | SPP |
| EDG-6 | 385 | SPP |
| EDG-7 | 353 | LPA |
| EDG-8 | 400 | SPP *Xenopus* |
| PSP24 | 372 | LPA Murine |
| PSP24 | 373 | LPA |

*Xenopus* PSP24 and murine expressed PSP24 specifically transduce GPM-evoked oscillatory chloride-currents (LPA, Fischer et al., 1998). These are not structurally homologous to the EDG family (Tigyi and Miledi, 1992; Fernhout et al., 1992). The EDG family can be divided into two distinct subgroups. The first group includes EDG-2, EDG-4, and EDG-7, which serve as receptors for only GPM (Hecht et al., 1996; An et al., 1998a; Bandoh et al., 1999; An et al., 1998b) and transmit numerous signals in response to ligand binding. The second group involves EDG-1, EDG-3, EDG-5, EDG-6, and EDG-8, and is specific for SPMs (An et al., 1997a; Im et al., 2000; van Brocklyn et al., 1998; van Brocklyn et al., 2000; Spiegel and Milstein, 2000). Principle tissue expression of the various PLGFR's is shown in Table 2 below.

TABLE 2

Human Tissue Expression of Phospholipid Growth Factor Receptors

| PLGFR | Human Tissue with Highest Expression |
|---|---|
| EDG-1 | Ubiquitous |
| EDG-2 | Cardiovascular, CNS, Gonadal tissue, GI |
| EDG-3 | Cardiovascular, Leukocyte |
| EDG-4 | Leukocyte, Testes |
| EDG-5 | Cardiovascular, CNS, Gonadal tissue, Placenta |
| EDG-6 | Lymphoid, Hematopoietic tissue |
| EDG-7 | Heart, Pancreas, Prostate, Testes |
| EDG-8 | Brain PSP24 CNS |

PLGFs activate multiple G-protein-mediated signal transduction events. These processes are mediated through the heterotrimeric G-protein families $G_{q/11}$, $G_{i/O}$, and $G_{12/13}$ (Moolenaar, 1997; Spiegel and Milstein, 1995; Gohla, et al., 1998).

The $G_{q/11}$ pathway is responsible for phospholipase C (PLC) activation, which in turn induces inositol triphosphate ($IP_3$) production with subsequent mobilization of $Ca^{2+}$ in a wide variety of cells (Tokumura, 1995). In some cells, this response is PTX-sensitive, implying that there is involvement of multiple PTX-sensitive and insensitive pathways (Tigyi et al., 1996). This pathway is also responsible for the diacyl glycerol (DAG)-mediated activation of protein kinase C (PKC). PKC activates cellular phospholipase D (PLD), which is responsible for the hydrolysis of phosphatidyl choline into free choline and PA (van der Bend et al., 1992a). Also, PLC is capable of activating MAP kinase directly, or via DAG activation of PKC in some cell types (Ghosh et al., 1997).

The mitogenic-signaling pathway is mediated through the G-protein heterotrimeric $G_{i/O}$ subunit. Transfection studies indicate that the $G_{i\beta\gamma}$ dimer rather than the αi subunit is responsible for Ras-MAP kinase activation. The activation of Ras is preceded by the transactivation of the receptor tyrosine kinases (RTKs) such as EGF (Cunnick et al., 1998) or PDGF receptors (Herrlich et al., 1998). The transactivated RTKS activate Ras, which leads to the activation of MAP kinases (ERK 1, 2) via Raf. The $G_{i\alpha}$ subunit, which is PTX-sensitive, inhibits adenylyl cyclase (AC), resulting in βγ dimer docking to a G-protein-coupled receptor kinase (GRKs) that phosphorylates and desensitizes the receptor. The phosphorylated receptor is recruited by β-arrestin, thus recruiting src kinase, which phosphorylates the EGF-receptor, generating its active conformation (Lin et al., 1997; Ahn et al., 1999; Luttrell et al., 1999). The transactivated RTKs, in turn, activate Ras, which leads to the activation of MAP kinases (ERK 1, 2) via Raf. The $G_{i\alpha}$ subunit, which is PTX-sensitive, inhibits AC, resulting in decreased levels of cyclic-AMP (cAMP). The opposite cellular effects by LPA, that is, mitogenesis and antimitogenesis, are accompanied by opposing effects on the cAMP second messenger system. Mitogenesis is mediated through the $G_{i\alpha}$ pathway, which results in decreased levels of cAMP (van Corven et al., 1989; van Corven et al., 1992), whereas anti-mitogenesis is accompanied by a non-PTX sensitive $Ca^{2+}$-dependent elevation of cAMP (Tigyi et al., 1994; Fischer et al., 1998).

In contrast, very little is known about the PTX-insensitive $G_{12/13}$ signaling pathway, which leads to the rearrangement of the actin-cytoskeleton. This pathway may also involve the transactivation of RTKs (Lin et al., 1997; Ahn et al., 1999; Luttrell et al., 1999; Gohla et al., 1998) and converge on a small GTPase, Rho (Moolenaar, 1997). Much more is known about the down-stream signaling of Rho because various protein partners have been isolated and identified. Rho activates Ser/Thr kinases, which phosphorylate, and as a result inhibit, myosin light chain phosphatase (MLC-phosphatase) (Kimura et al., 1996). This path results in the accumulation of the phosphorylated form of MLC, leading to cytoskeletal responses that lead to cellular effects like retraction of neurites (Tigyi and Miledi, 1992; Tigyi et al., 1996; Dyer et al., 1992; Postma et al., 1996; Sato et al., 1997), induction of stress fibers (Ridley and Hall, 1992; Gonda et al., 1999), stimulation of chemotaxis (Jalink et al., 1993a), cell migration (Zhou et al., 1995; Kimura et al., 1992), and tumor cell invasiveness (Imamura et al., 1993; Imamura et al., 1996). The PLGF-induced, Rho-mediated, tumor cell invasiveness is blocked by C. botulinium C3-toxin, which specifically ribosylates Rho in an ADP-dependent mechanism (Imamura et al., 1996).

Rho also has the ability to stimulate DNA synthesis in quiescent fibroblasts (Machesky and Hall, 1996; Ridley, 1996). The expression of Rho family GTPase activates serum-response factor (SRF), which mediates early gene transcription (Hill et al., 1995). Furthermore, PLGF (LPA) induces tumor cell invasion (Imamura et al., 1996); however, it is still unclear whether it involves cytoskeletal changes or gene transcription, or both.

By virtue of LPA/LPA receptor involvement in a number of cellular pathways and cell activities such as proliferation and/or migration, as well as their implication in wound healing and cancer, it would be desirable to identify novel compounds which are capable of acting, preferably selectively, as either antagonists or agonists at the LPA receptors identified above.

There are currently very few synthetic or endogenous LPA receptor inhibitors which are known. Of the antagonists reported to date, the most work was done on SPH, SPP, N-palmitoyl-1-serine (Bittman et al., 1996), and N-palmitoyl-1-tyrosine (Bittman et al., 1996). It is known that the above-mentioned compounds inhibit LPA-induced chloride currents in the Xenopus oocyte (Bittman et al., 1996; Zsiros et al., 1998). However, these compounds have not been studied in all cell systems. It is also known that SPP inhibits tumor cell invasiveness, but it is uncertain whether SPP does so by being an inhibitor of LPA or via the actions of its own receptors. N-palmitoyl-1-serine and N-palmitoyl-1-tyrosine also inhibited LPA-induced platelet aggregation (Sugiura et al., 1994), but it remains to be seen whether these compounds act at the LPA receptor. Lysophosphatidyl glycerol (LPG) was the first lipid to show some degree of inhibition of LPA actions (van der Bend et al., 1992b), but it was not detectable in several LPA-responsive cells types (Liliom et al., 1996). None of these inhibitors was shown to selectively act at specific LPA receptors.

A polysulfonated compound, Suramin, was shown to inhibit LPA-induced DNA synthesis in a reversible and dose-dependent manner. However, it was shown that Suramin does not have any specificity towards the LPA receptor and blocked the actions of LPA only at very high millimolar (mM) concentrations (van Corven et al., 1992).

The present invention is directed to addressing the lack of agents which act as LPA agonists and LPA antagonists.

SUMMARY OF THE INVENTION

The present invention relates to compounds according to formula (I)

$$\begin{array}{c} X^3 \\ | \\ CQ^1-CH-CQ^2 \\ | \quad\quad\quad | \\ X^1 \quad\quad\quad X^2 \end{array} \quad (I)$$

wherein, at least one of $X^1$, $X^2$, and $X^3$ is $(HO)_2PS-Z^1-$, or $(HO)_2PO-Z^2-P(OH)S-Z^1-$, $X^1$ and $X^2$ are linked together as $-O-PS(OH)-O-$, or $X^1$ and $X^3$ are linked together as $-O-PS(OH)-NH-$;

at least one of $X^1$, $X^2$, and $X^3$ is $R^1-Y^1-A-$ with each being the same or different when two of $X^1$, $X^2$, and $X^3$ are $R^1-Y^1-A-$, or $X^2$ and $X^3$ are linked together as $-N(H)-C(O)-N(R^1)-$;

optionally, one of $X^1$, $X^2$, and $X^3$ is H;

A is either a direct link, $(CH_2)_k$ with k being an integer from 0 to 30, or O;

$Y^1$ is $-(CH_2)_l-$ with l being an integer from 1 to 30, $-O-$, $-S-$, $$-\overset{O}{\underset{\|}{C}}-$$

or $-NR^2-$;

$Z^1$, is $-(CH_2)_m-$, $-CF_2-$, $-CF_2(CH_2)_m-$, or $-O(CH_2)_m-$ with m being an integer from 1 to 50, $-C(R^3)H-$, $-NH-$, $-O-$, or $-S-$;

$Z^2$ is $-(CH_2)_n-$ or $-O(CH_2)_n-$ with n being an integer from 1 to 50 or $-O-$;

$Q^1$ and $Q^2$ are independently $H_2$, $=NR^4$, $=O$, or a combination of H and $-NR^5R^6$;

$R^1$, for each of $X^1$, $X^2$, or $X^3$, is independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl, $$-\underset{NH_2}{\overset{CH}{\underset{\|}{}}}, \quad \begin{array}{c}N\\ \diagup\diagdown \\ N \\ \quad R^8\end{array}\!\!R^7, \quad \begin{array}{c}N\\ \diagup\diagdown \\ N \\ \quad R^8\end{array}\!\!R^7,$$

$$-\underset{NR^8}{\overset{C}{\underset{\|}{}}}-NH-R^7, \quad -\underset{O}{\overset{C}{\underset{\|}{}}}-NH-R^7, \quad -\underset{S}{\overset{C}{\underset{\|}{}}}-NH-R^7,$$

$$-\underset{O}{\overset{C}{\underset{\|}{}}}-O-R^7; \text{ and}$$

$R^2$, $R^3$, $R^4$, $R^5$, $R^6$, $R^7$, and $R^8$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alky, or an aryloxyalkyl including straight or branched-chain C1 to C30 alkyl.

Also disclosed are pharmaceutical compositions which include a pharmaceutically-acceptable carrier and a compound of the present invention.

A further aspect of the present invention relates to a method of inhibiting LPA activity on an LPA receptor which includes providing a compound of the present invention which has activity as an LPA receptor antagonist and contacting an LPA receptor with the compound under conditions effective to inhibit LPA-induced activity of the LPA receptor.

Another aspect of the present invention relates to a method of modulating LPA receptor activity which includes providing a compound of the present invention which has activity as either an LPA receptor agonist or an LPA receptor antagonist and contacting an LPA receptor with the compound under conditions effective to modulate the activity of the LPA receptor.

Still another aspect of the present invention relates to a method of treating cancer which includes providing a compound of the present invention and administering an effective amount of the compound to a patient in a manner effective to treat cancer.

Yet another aspect of the present invention relates to a method of enhancing cell proliferation which includes providing a compound the present invention which has activity as an agonist of an LPA receptor and contacting the LPA receptor on a cell with the compound in a manner effective to enhance LPA receptor-induced proliferation of the cell.

A further aspect of the present invention relates to a method of treating a wound which includes providing a compound of the present invention which has activity as an agonist of an LPA receptor and delivering an effective amount of the compound to a wound site, where the compound binds to LPA receptors on cells that promote healing of the wound, thereby stimulating LPA receptor agonist-induced cell proliferation to promote wound healing.

A still further aspect of the present invention relates to a method of making the compounds of the present invention. One approach for making the compounds of the present invention includes:

reacting $(Y^2O)_2PO-Z^{11}-Z^{13}$ or $(Y^2O)_2PO-Z^{12}-P(OH)-O-Z^{11}-Z^{13}$, where $Z^{11}$ is $-(CH_2)_m-$, $CF_2-$, $-CF_2(CH_2)_m-$, or $-O(CH_2)_m-$ with m being an integer from 1 to 50, $-C(R^3)H-$, $-NH-$, or $-S-$;

$Z^{12}$ is $-(CH_2)_n-$ or $-(CH_2)_n-$ with n being an integer from 1 to 50 or $-O-$, $Z^{13}$ is H or a first leaving group or $-Z^{11}-Z^{13}$ together form the first leaving group; and $Y^2$ is H or a protecting group, with an intermediate compound according to formula (IX) in the presence of sulfur $$\begin{array}{c} X^{13} \\ | \\ CQ^{11}-CH_2-CQ^{12} \\ | \quad\quad\quad\quad | \\ X^{11} \quad\quad\quad X^{12} \end{array} \quad (IX)$$

where, at least one of $X^{11}$, $X^{12}$, and $X^{13}$ is $R^{11}-Y^{11}-A-$ with each being the same or different when two of $X^{11}$, $X^{12}$, and $X^{13}$ are $R^{11}-Y^{11}-A-$, or $X^{12}$ and $X^{13}$ are linked together as $-N(H)-C(O)-N(R^{11})-$;

at least one of $X^{11}$, $X^{12}$, and $X^{13}$ is OH, NH$_2$, SH, or a second leaving group;

optionally, one of $X^{11}$, $X^{12}$, and $X^{13}$ is H;

A is either a direct link, (CH$_2$)$_k$ with k being an integer from 0 to 30, or O;

$Y^{11}$ is —(CH$_2$)$_l$— with l being an integer from 1 to 30, —O—,

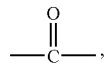

—S—, or —NR$^{12}$—;

$Q^1$ and $Q^2$ are independently H$_2$, =NR$^{13}$, =O, a combination of H and —NR$^{14}$R$^{15}$;

$R^{11}$, for each of $X^{11}$, $X^{12}$, or $X^{13}$, is independently hydrogen, a straight or branched-chain C1 to C30 alkyl, a straight or branched-chain C2 to C30 alkenyl, an aromatic or heteroaromatic ring with or without

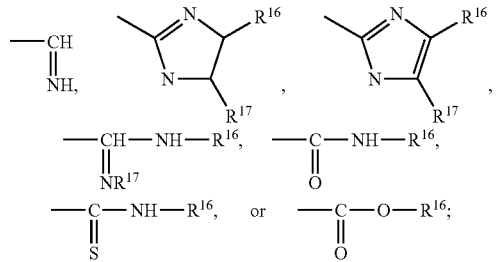

and mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl, $R^{12}$, $R^{13}$, $R^{14}$, $R^{15}$, $R^{16}$, and $R^{17}$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl; followed by a de-protection step, if necessary, with both said reacting and the deprotection step being performed under conditions effective to afford a compound according to formula (I) where one or two of $X^1$, $X^2$, and $X^3$ is (HO)$_2$PS—$Z^1$— or (HO)$_2$PS—$Z^2$—P(OH)S—$Z^1$—.

Yet another aspect of the present invention relates to a method of treating apoptosis or preserving or restoring function in a cell, tissue, or organ which includes: providing a compound of the present invention which has activity as an agonist of an LPA receptor; and contacting a cell, tissue, or organ with an amount of the compound which is effective to treat apoptosis or preserve or restore function in the cell, tissue, or organ.

A further aspect of the present invention relates to a method of culturing cells which includes: culturing cells in a culture medium which includes a compound of the present invention which has activity as an agonist of an LPA receptor and is present in an amount which is effective to prevent apoptosis or preserve the cells in culture.

Another aspect of the present invention relates to a method of preserving an organ or tissue which includes: providing a compound of the present invention which has activity as an agonist of an LPA receptor; and treating an organ or tissue with a solution comprising the compound in an amount which is effective to preserve the organ or tissue function.

A related aspect of the present invention relates to an alternative method of preserving an organ or tissue which includes: providing a compound of the present invention which has activity as an agonist of an LPA receptor; and administering to a recipient of a transplanted organ or tissue an amount of the compound which is effective to preserve the organ or tissue function A still further aspect of the present invention relates to a method of treating a dermatological condition which includes: providing a compound of the present invention which has activity as an LPA receptor agonist; and topically administering a composition comprising the compound to a patient, the compound being present in an amount which is effective to treat the dermatological condition The compounds of the present invention which have been identified herein as being either agonists or antagonists of one or more LPA receptors find uses to inhibit or enhance, respectively, biochemical pathways mediated by LPA receptor signaling. By modulating LPA receptor signaling, the antagonists and agonists find specific and substantial uses as described herein.

BRIEF DESCRIPTION OF THE DRAWINGS

FIG. 1 illustrates three reaction schemes used to prepare fatty acid phosphates (Scheme 1), fatty acid thiophosphonates (Scheme 2), and difluorophosphonates (Scheme 3).

FIGS. 2A-D are graphs illustrating the effects of modified C-14 analogs on RH7777 cells stably transfected with LPA$_{1-3}$ receptors. 200 nM of LPA 18:1 was co-applied with increasing concentrations of C-14 analogs to RH7777 cells stably expressing LPA$_1$ and LPA$_3$. Increasing concentrations of different C-14 analogs were applied to measure their agonistic properties at LPA$_2$. Data points represent average of four measurements. FIG. 2A shows inhibition of the LPA response by C-14 analogs at LPA$_1$; FIG. 2B shows activation of LPA$_2$ by C-14 FAP analogs; FIG. 2C shows inhibition of the LPA response by C-14 phosphonate 9c at LPA$_2$; and FIG. 2D shows inhibition of the LPA response by C-14 analogs at LPA$_3$.

FIGS. 3A-C are graphs illustrating that oleoyl-thiophosphate (8 g) is an agonist at LPA$_1$, LPA$_2$ and LPA$_3$ receptors expressed in RH7777 cells. Intracellular Ca$^{2+}$ transients were measured in response to the application of increasing concentrations of 8 g and compared to transients elicited by the corresponding amount of LPA 18:1. Data points represent the average of four measurements. Dose-response relationships for LPA 18:1 and 8 g in RH7777 cells expressing LPA$_1$ (FIG. 3A), LPA$_2$ (FIG. 3B), and LPA$_3$ (FIG. 3C).

DETAILED DESCRIPTION OF THE INVENTION

Figure 4:
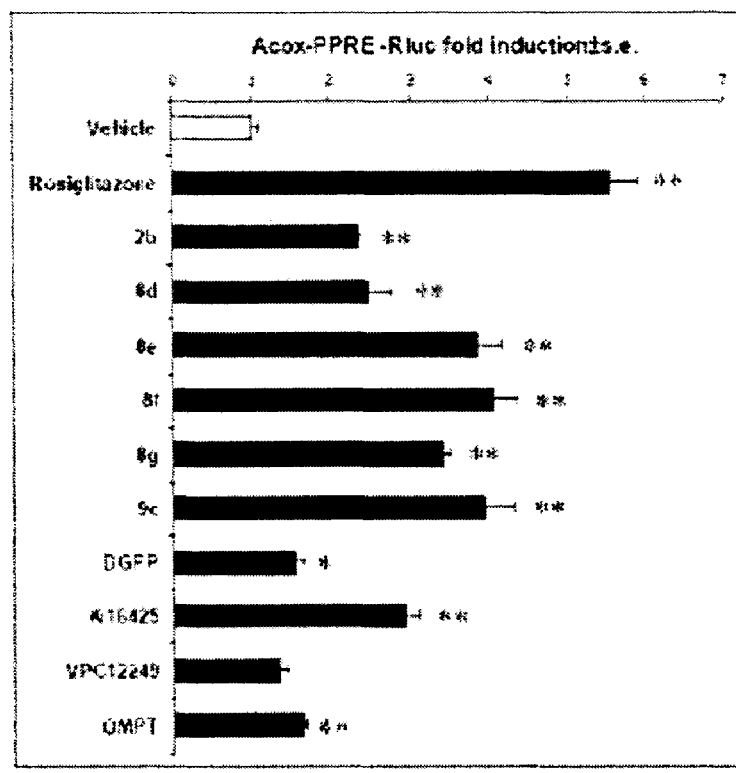
FIG. 4 is a bar graph depicting the results of in vitro PPARγ activation by selected compounds in CV1 cells transfected with PPARγ and PPRE-Acox-Rluc reporter gene. Comparing the effects with the Rosiglitazone, a known PPARγ agonist, CV1 cells were treated with 1% DMSO or 10 μM of test compound dissolved in DMSO for 20 h. Luciferase and β-galactosidase activities (mean ±SEM) were measured in the cell lysate (n=4). *P<0.05 and **P<0.01, significant differences over vehicle control.

One aspect of the present invention relates to a compound according to formula (I)

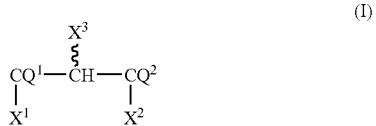

wherein, at least one of $X^1$, $X^2$, and $X^3$ is $(HO)_2PS-Z^1-$, or $(HO)_2PS-Z^2-P(OH)S-Z^1-$, $X^1$ and $X^2$ are linked together as $-O-PS(OH)-O-$, or $X^1$ and $X^3$ are linked together as $-O-PS(OH)-NH-$;

at least one of $X^1$, $X^2$, and $X^3$ is $R^1-Y^1-A-$ with each being the same or different when two of $X^1$, $X^2$, and $X^3$ are $R^1-Y^1-A-$, or $X^2$ and $X^3$ are linked together as $-N(H)-C(O)-N(R^1)-$;

optionally, one of $X^1$, $X^2$, and $X^3$ is H;

A is either a direct link, $(CH_2)_k$ with k being an integer from 0 to 30, or $-O-$;

$Y^1$ is $-(CH_2)_l-$ with l being an integer from 1 to 30, $-O-$,

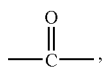

$-S-$, or $-NR^2-$;

$Z^1$ is $-(CH_2)_m-$, $-CF_2-$, $-CF_2(CH_2)_m-$, or $-O(CH_2)_m-$ with m being an integer from 1 to 50, $-C(R^3)H-$, $-NH-$, $-O-$, or $-S-$;

$Z^2$ is $-(CH_2)_n-$ or $-O(CH_2)_n-$ with n being an integer from 1 to 50 or $-O-$;

$Q^1$ and $Q^2$ are independently $H_2$, $=NR^4$, $=O$, a combination of H and $-NR^5R^6$;

$R^1$, for each of $X^1$, $X^2$, or $X^3$, is independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, an aryloxyalkyl including straight or branched-chain C1 to C30 alkyl,

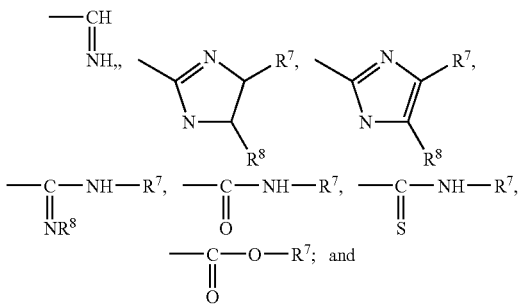

$R^2$, $R^3$, $R^4$, $R^5$, $R^6$, $R^7$, and $R^8$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl.

For each of the above-identified R groups (e.g., $R^1-R^8$), straight chain alkyls have the formula $-(CH_2)_xCH_3$ where x is from 0 to 29; branched chain alkyls have the formula as defined above for straight chain alkyl, except that one or more $CH_2$ groups are replaced by CHW groups where W is an alkyl side chain; straight chain alkenyls have the formula $-(CH_2)_{Xa}CH=CH(CH_2)_{Xb}CH_3$ where Xa and Xb each are from 0 to 27 and (Xa+Xb) is not more than 27; and branched chain alkenyls have the formula as defined above for straight chain alkenyl, except that one or more $CH_2$ groups are replaced by CHW groups or a CH group is replaced by a CW group, where W is an alkyl side chain. Preferred hydrocarbon groups are preferably between about 8 to about 18 carbon atoms in length, more preferably between about 10 to about 16 carbon atoms in length, and may contain one or more double bonds.

Aromatic or heteroaromatic rings include, without limitation, phenyls, indenes, pyrroles, imidazoles, oxazoles, pyrazoles, pyridines, pyrimidines, pyrrolidines, piperidines, thiophenes, furans, napthals, bi-phenyls, and indoles. The aromatic or heteroaromatic rings can include mono-, di-, or tri-substitutions of the ring located at the ortho, meta, or para positions on the rings relative to where the ring binds to the $Y^1$ group of the $R^1-Y^1-A-$ chain. Substitutions on the rings can include, without limitation, alkyl, alkoxy, amine (including secondary or tertiary amines), alkylamine, amide, alkylamide, acids, alcohols.

Acyl groups can include either alkyl alkenyl, or aromatic or heteroaromatic rings as described above.

Arylalkyl and aryloxyalkyl groups can include, without limitation, straight or branched-chain C1 to C30 alkyl groups as described above, with the alkyl group binding to the $Y^1$ group of the $R^1-Y^1-A-$ chain.

Exemplary compounds according to formula (I) are the subclass compounds according to formulae (II)-(VII) below.

In the structures of formulae (II)A and (II)B, $Q^1$ and $Q^2$ are both $H_2$; one of $X^1$, $X^2$, and $X^3$ is $(HO)_2PS-Z^2-P(OH)S-Z^1-$, with $Z^1$ and $Z^2$ being O; and two of $X^1$, $X^2$, and $X^3$ are $R^1-Y^1-A-$, with A being a direct link and $Y^1$ being O for each. Each $R^1$ is defined independently as above for formula (I).

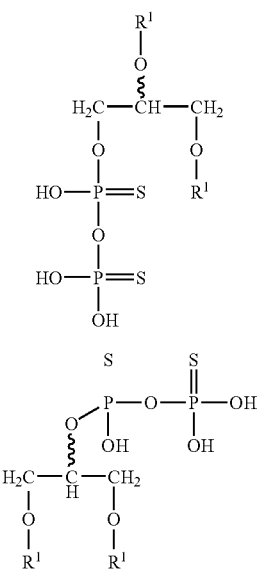

(II)A (II)B

In the structures of formula (III), $Q^1$ is $H_2$; $Q^2$ is —O—; $X^1$ is $(HO)_2PO$—$Z^1$—, with $Z^1$ being O; and $X^2$ and $X^3$ are $R^1$—$Y^1$-A-, with A being a direct link and $Y^1$ being —NH— for each. Each $R^1$ is defined independently as above for formula (I). Preferred species of within the scope of formula III are where $X^3$ is —$NH_2$ and $X^2$ is —$NHR^1$ with $R^1$ being a C10 to C18 alkyl, more preferably either a C14 alkyl or a C18 alkyl; or where $X^3$ is —$NHR^1$ with $R^1$ being an acetyl group and $X^2$ is —$NHR^1$ with $R^1$ being a C14 alkyl.

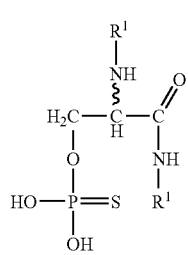

(III)

In the structures of formula (IV), $Q^1$ is =$NR^4$; $Q^2$ is $H_2$; $X^1$ and $X^2$ are linked together as —O—PO(OH)—O—; and $X^3$ is $R^1$—$Y^1$-A-, with A being a direct link and $Y^1$ being —NH—. $R^1$ and $R^4$ are as defined above for formula (I).

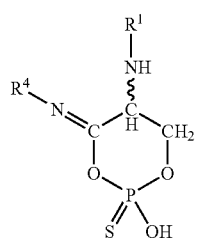

(IV)

In the structures of formulae (V)A and (V)B, $Q^1$ and $Q^2$ are both $H_2$; two of $X^1$, $X^2$, and $X^3$ are $(HO)_2PO$—$Z^1$—, with $Z^1$ being O for each; and one of $X^1$, $X^2$, and $X^3$ is $R^1$—$Y^1$-A-, with A being a direct link and $Y^1$ being —O—. $R^1$ is as defined above for formula (I). Preferred species within the scope of formulae (V)A and (V)B include the compounds where $R^1$ is an acyl including a C21 alkyl or where $R^1$ is a C18 alkyl.

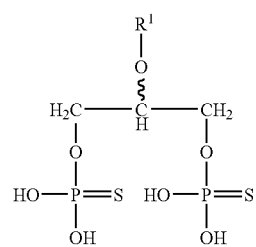

(V)A

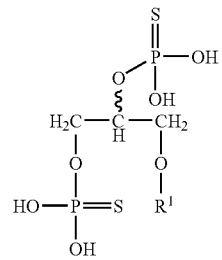

(V)B

The compounds according to formula (I), as well as the subgenus compounds according to formulae (II)A, (II)B, (III), (IV), (V)A, and (V)B, may be prepared using the synthesis schemes described in PCT/US01/08729, filed Mar. 19, 2001, (incorporated by reference in its entirety) except that phosphoramidate or pyrophosphates can be reacted in the presence of sulfur (with reflux) to obtain the thio-substituted derivatives.

In the compounds according to formula (VI), $Q^1$ and $Q^2$ are both $H_2$; one of $X^1$ and $X^2$ is $(HO)_2PS$—$Z^1$—, with $Z^1$ being O; and one of $X^1$, $X^2$, and $X^3$ is $R^1$—$Y^1$-A-, with A being a direct link and $Y^1$ being —$CH_2$—. $R^1$ is as defined above for formula (I). Preferred $R^1$ groups are saturated and unsaturated C2 to C24 hydrocarbons, both straight and branched chain, and arylakyl groups containing C2 to C24 hydrocarbons; most preferred $R^1$ groups are saturated and unsaturated C4 to C18 hydrocarbons. A preferred compound according to formula VI is thiophosphoric acid O-octadec-9-enyl ester (8 g; also referred to as FAP 18:1d9).

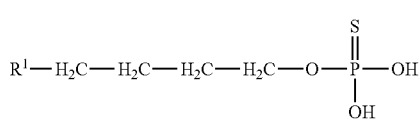

(VI)

The synthesis of thiophosphonates according to formula (VI) is outlined in scheme 2 of FIG. 1. The protected thiophosphoric acid O,O'-bis-(2-cyano-ethyl) ester O"-alkyl/alkenyl esters can be synthesized using a modified method of Haines et al. (1996). Commercially available fatty alcohols (6a-g) can be treated with a mixture of 1H-tetrazole and bis(2-cyanoethyl)-N,Ndiisopropyl phosphoramidite in anhydrous methylene chloride followed by reflux in the presence of elemental sulfur to give bis-cyanoethyl protected fatty alcohol thiophosphates (7a-g). These protected thiophosphates can be treated with methanolic KOH, followed by acidification to yield the required thiophosphates (8a-g).

In the structures of formulae (VII)A and (VII)B, $Q^1$ and $Q^2$ are both H2; one of $X^1$, $X^2$, and $X^3$ is $(HO)_2PS$—$Z^1$—with $Z^1$ being O; and two of $X^1$, $X^2$, and $X^3$ are $R^1$—$Y^1$-A-, with A being a direct link and $Y^1$ being O for each. Each $R^1$ is defined independently as above for formula (I).

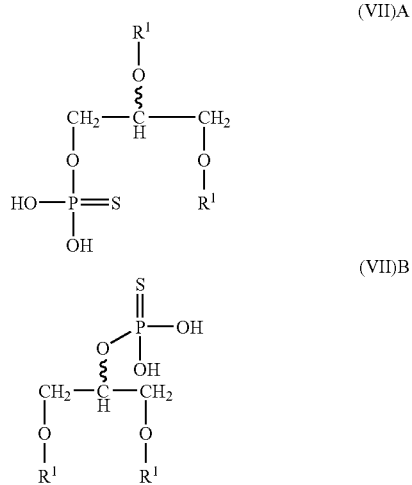

Preferred $R^1$ groups are saturated and unsaturated C6 to C24 hydrocarbons, both straight and branched chain; most preferred $R^1$ groups are saturated and unsaturated C8 to C18 hydrocarbons. Two preferred compounds according to group (VII)A are the (R) and (S) enantiomers where both $R^1$ groups are saturated octyl groups. The (R) enantiomer is a partial $LPA_1$ agonist ($EC_{50}$: 695 nM), a transient partial $LPA_2$ agonist ($EC_{50}$: 1.02 µM), and a full $LPA_3$ ($EC_{50}$: 3 nM) agonist. The (S) enantiomer is an agonist of the $LPA_1$ and $LPA_3$ receptors ($IC_{50}$ 328 nM for $LPA_1$ and $IC_{50}$ 184 nM for $LPA_3$ (both for 200 nM LPA)).

The compounds of formulae (VII)A and (VII)B can be prepared using the synthesis schemes described in PCT/US01/08729, filed Mar. 19, 2001, which is hereby incorporated by reference in its entirety, except that phosphoramidate can be reacted in the presence of sulfur (with reflux) to obtain the thio-substituted derivatives.

In the compounds according to formula (VIII), $Q^1$ and $Q^2$ are both $H_2$; one of $X^1$ and $X^2$ is $(HO)_2PS$—$Z^1$—, with $Z^1$ being $CF_2$; and one of $X^1$, $X^2$, and $X^3$ is $R^1$—$Y^1$-A-, with A being a direct link and $Y^1$ being —$CH_2$—. $R^1$ is as defined above for formula (I).

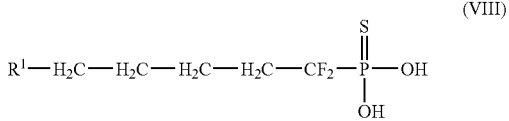

Preferred $R^1$ groups are saturated and unsaturated C2 to C20 hydrocarbons, both straight and branched chain; most preferred $R^1$ groups are saturated and unsaturated C4 to C12 hydrocarbons.

The synthesis of difluorothiophosphonates according to formula (VIII) is outlined in Scheme 3 of FIG. 1. The tetradecyl difluorophosphonate analog was synthesized in two steps (Scheme 3) using diethyl difluoromethanephosphonate as the starting material (Halazy et al., 1991). Diethyl difluoromethanephosphonate was treated with LDA at −78° C. followed by reacting the anion with tetradecyl bromide to give the protected phosphonate 10. Compound 10 was deprotected using bromotrimethyl silane to yield the required difluorophosphonate compound (11).

Thus, the non-cyclic compounds of the present invention can be prepared by reacting $(Y^2O)_2PO$—$Z^{11}$—$Z^{13}$, $(Y^2O)_2PO$—$Z^{12}$-P(OH)S—$Z^{11}$—$Z^{13}$, where $Z^{11}$ is —$(CH_2)_m$—, —$CF_2$—, —$CF_2(CH_2)_m$, or —$O(CH_2)_m$— with m being an integer from 1 to 50, —$C(R^3)H$—, or —O—, $Z^{12}$ is —$(CH_2)_n$— or —$O(CH_2)_n$— with n being an integer from 1 to 50 or —O—, $Z^{13}$ is H or a first leaving group or —$Z^{11}$—$Z^{13}$ together to form the first leaving group, and $Y^2$ is H or a protecting group; with an intermediate compound according to formula (IX) in the presence of sulfur, followed by a de-protection step, if necessary, both performed under conditions effective to afford a compound according to formula (I) where one or two of $X^1$, $X^2$, and $X^3$ is $(HO)_2PS$—$Z^1$—or $(HO)_2PS$—$Z^2$—P(OH)S—$Z^1$—with $Z^1$ and $Z^2$ being defined as above.

The intermediate compound of formula (IX) has the following structure:

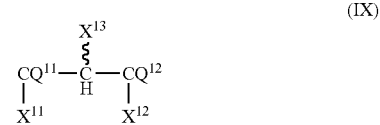

wherein, at least one of $X^{11}$, $X^{12}$, and $X^{13}$ is $R^{11}$—$Y^{11}$-A- with each being the same or different when two of $X^{11}$, $X^{12}$, and $X^{13}$ are $R^{11}$—$Y^{11}$-A-, or $X^{12}$ and $X^{13}$ are linked together as —N(H)—C(O)—N($R^{11}$)—;

at least one of $X^{11}$, $X^{12}$, and $X^{13}$ is OH, $NH_2$, SH, or a second leaving group;

optionally, one of $X^{11}$, $X^{12}$, and $X^{13}$ is H;

A is either a direct link, $(CH_2)_k$ with k being an integer from 0 to 30, or O;

$Y^{11}$ is —$(CH_2)_l$— with l being an integer from 1 to 30, —O—,

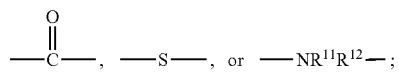

$Q^1$ and $Q^2$ are independently $H_2$, =$NR^{13}$, =O, a combination of H and —$NR^{14}R^{15}$;

$R^{11}$, for each of $X^{11}$, $X^{12}$, or $X^{13}$, is independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl,

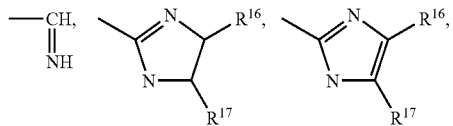

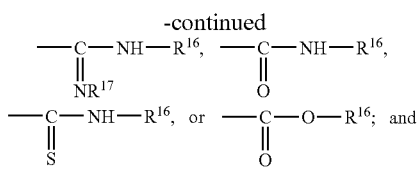

$R^{12}$, $R^{13}$, $R^{14}$, $R^{15}$, $R^{16}$, and $R^{17}$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl.

Having prepared the LPA receptor agonists and antagonists of the present invention, such compounds can be used to prepare pharmaceutical compositions suitable for treatment of patients as described hereinafter. Therefore, a further aspect of the present invention relates to a pharmaceutical composition that includes a pharmaceutically-acceptable carrier and a compound of the present invention. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 20 to 75 percent of active compound(s), together with the carrier, excipient, stabilizer, etc.

The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The compounds of the present invention may also be administered in injectable or topically-applied dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Compositions within the scope of this invention include all compositions wherein the compound of the present invention is contained in an amount effective to achieve its intended purpose. While individual needs vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art.

Certain compounds of the present invention have been found to be useful as agonists of LPA receptors while other compounds of the present invention have been found useful as antagonists of LPA receptors. Due to their differences in activity, the various compounds find different uses. The preferred animal subject of the present invention is a mammal. The invention is particularly useful in the treatment of human subjects.

One aspect of the present invention relates to a method of modulating LPA receptor activity which includes providing a compound of the present invention which has activity as either an LPA receptor agonist or an LPA receptor antagonist and contacting an LPA receptor with the compound under conditions effective to modulate the activity of the LPA receptor.

The LPA receptor is present on a cell which either normally expresses the LPA receptor or has otherwise been transformed to express a particular LPA receptor. Suitable LPA receptors include, without limitation, EDG-2 ($LPA_1$), EDG-4 ($LPA_2$), EDG-7 ($LPA_3$), GPR23 ($LPA_4$) (Noguchi et al. 2003), and PSP-24 receptors. The tissues which contain cells that normally express these receptors are indicated in Table 1. When contacting a cell with the LPA receptor agonist or LPA receptor antagonist of the present invention, the contacting can be carried out while the cell resides in vitro or in vivo.

To heterologously express these receptors in host cells which do not normally express them, a nucleic acid molecule encoding one or more of such receptors can be inserted in sense orientation into an expression vector which includes appropriate transcription and translations regulatory regions (i.e., promoter and transcription termination signals) and then host cells can be transformed with the expression vector. The expression vector may integrate in the cellular genome or simply be present as extra-chromosomal nuclear material. Expression can be either constitutive or inducible, although constitutive expression is suitable for most purposes.

The nucleotide and amino acid sequences for EDG-2 is known and reported in An et al. (1997b) and Genbank Accession No. U80811, which is hereby incorporated by reference. An EDG-2 ($LPA_1$) encoding nucleic acid molecule has a nucleotide sequence according to SEQ. ID. No. 1 as follows:

```
atggctgcca tctctacttc catccctgta atttcacagc cccagttcac agccatgaat    60
gaaccacagt gcttctacca cgagtccatt gccttctttt ataaccgaag tggaaagcat   120
```

-continued

```
cttgccacag aatggaacac agtcagcaag ctggtgatgg gacttggaat cactgtttgt   180
atcttcatca tgttggccaa cctattggtc atggtggcaa tctatgtcaa ccgccgcttc   240
cattttccta tttattacct aatggctaat ctggctgctg cagacttctt tgctgggttg   300
gcctacttct atctcatgtt caacacagga cccaatactc ggagactgac tgttagcaca   360
tggctcctgc gtcagggcct cattgacacc agcctgacgg catctgtggc caacttactg   420
gctattgcaa tcgagaggaa cattacggtt ttccgcatgc agctccacac acggatgagc   480
aaccggcggg tagtggtggt cattgtggtc atctggacta tggccatcgt tatgggtgct   540
atacccagtg tgggctggaa ctgtatccgt gatattgaaa attgttccaa catggcaccc   600
ctctacagtg actcttactt agtcttctgg gccattttca cttggtgac ctttgtggta   660 atggtggttc tctatgctca catctttggc tatgttcgcc agaggactat gagaatgtct   720
cggcatagtt ctggaccccg gcggaatcgg gataccatga tgagtcttct gaagactgtg   780
gtcattgtgc ttggggcctt tatcatctgc tggactcctg gattggtttt gttacttcta   840
gacgtgtgct gtccacagtg cgacgtgctg gcctatgaga aattctttt tctccttgct   900 gaattcaact ctgccatgaa ccccatcatt tactcctacc gcgacaaaga aatgagcgcc   960
acctttaggc agatcctctg ctgccagcgc agtgagaacc ccaccggccc cacagaaagc  1020
tcagaccgct cggcttcctc cctcaaccac accatcttgg ctggagttca cagcaatgac  1080
cactctgtgg tttag                                                   1093
```

The encoded EDG-2 (LPA$_1$) receptor has an amino acid sequence according to SEQ. ID. No. 2 as follows:

```
MAAISTSIPV ISQPQFTAMN EPQCFYNESI AFFYNRSGKH LATEWNTVSK LVMGLGITVC   60

IFIMLANLLV MVAIYVNRRF HFPIYYLMAN LAAADFFAGL AYFYLMFNTG PNTRRLTVST  120

WLLRQGLIDT SLTASVANLL AIAIERHITV FRMQLHTRMS NRRVVVVIVV IWTMAIVMGA  180

IPSVGWNCIC DIENCSNMAP LYSDSYLVFW AIFNLVTFVV MVVLYAHIFG YVRQRTMRMS  240

RHSSGPRRNR DTMMSLLKTV VIVLGAFIIC WTPGLVLLLL DVCCPQCDVL AYEKFFLLLA  300

EFNSAMNPII YSYRDKEMSA TFRQILCCQR SENPTGPTES SDRSASSLNH TILAGVHSND  360

HSVV                                                               364
```

The nucleotide and amino acid sequences for EDG-4 (LPA$_2$) is known and reported in An et al. (1998b) and Genbank Accession No. NM$_{004720}$. An EDG-4 encoding nucleic acid molecule has a nucleotide sequence according to SEQ. ID. No. 3 as follows:

```
atggtcatca tgggccagtg ctactacaac gagaccatcg gcttcttcta taacaacagt    60
ggcaaagagc tcagctccca ctggcggccc aaggatgtgg tcgtggtggc actggggctg   120
accgtcagcg tgctggtgct gctgaccaat ctgctggtca tagcagccat cgcctccaac   180
cgccgcttcc accagcccat ctactacctg ctcggcaatc tggccgcggc tgacctcttc   240
gcgggcgtgg cctacctctt cctcatgttc cacactggtc cccgcacagc ccgacttca   300 cttgagggct ggttcctgcg gcagggcttg ctggacacaa gctcactgc gtcggtggcc   360 acactgctgg ccatcgccgt ggagcggcac cgcagtgtga tggccgtgca gctgcacagc   420
cgcctgcccc gtgccgcgt ggtcatgctc attgtgggcg tgtgggtggc tgccctgggc   480
ctggggctgc tgcctgccCa ctcctggcac tgcctctgtg ccctggaccg ctgctcacgc   540
```

```
atggcacccc tgctcagccg ctcctatttg gccgtctggg ctctgtcgag cctgcttgtc    600
ttcatgctca tggtggctgt gtacacccgc attttcttct acgtgcggcg gcgagtgcag    660
cgcatggcag agcatgtcag ctgccacccc cgctaccgag agaccacgct cagcctggtc    720
aagactgttg tcatcatcct gggggcgttc gtggtctgct ggacaccagg ccaggtggta    780
ctgctcctgg atggtttagg ctgtgagtcc tgcaatgtcc tggctgtaga aaagtacttc    840
ctactgttgg ccgaggccaa ctcactggtc aatgctgctg tgtactcttg ccgagatgct    900
gagatgcgcc gcaccttccg ccgccttctc tgctgcgcgt gcctccgcca gtccacccgc    960
gagtctgtcc actatacatc ctctgcccag ggaggtgcca gcactcgcat cacgcttccc   1020
gagaacggcc acccactgat ggactccacc ctttag                             1056
```

The encoded EDG-4 (LPA$_2$) receptor has an amino acid sequence according to SEQ. ID. No. 4 as follows:

```
MVIMGQCYYN ETIGFFYNNS GKELSSHWRP KDVVVVALGL TVSVLVLLTN LLVIAAIASN     60

RRFHQPIYYL LGNLAAADLF AGVAYLFLMF HTGPRTARLS LEGWFLRQGL LDTSLTASVA    120

TLLAIAVERH RSVMAVQLHS RLPRGRVVML IVGVWVAALG LGLLPAHSWH CLCALDRCSR    180

MAPLLSRSYL AVWALSSLLV FLLMVAVYTR IFFYVRRRVQ RMAEHVSCHP RYRETTLSLV    240

KTVVIILGAF VVCWTPGQVV LLLDGLGCES CNVLAVEKYF LLLAEANSLV NAAVYSCRDA    300

EMRRTFRRLL CCACLRQSTR ESVHYTSSAQ GGASTRIMLP ENGHPLMDST 1             351
```

The nucleotide and amino acid sequences for EDG-7 (LPA$_3$) is known and reported in Bandoh et al. (1999) and Genbank Accession No. NM$_{012152}$. An EDG-7 encoding nucleic acid molecule has a nucleotide sequence according to SEQ. ID. No. 5 as follows:

```
atgaatgagt gtcactatga caagcacatg gactttttt ataataggag caacactgat      60
actgtcgatg actggacagg aacaaagctt gtgattgttt tgtgtgttgg gacgtttttc    120
tgcctgttta tttttttttc taattctctg gtcatcgcgg cagtgatcaa aaacagaaaa    180
tttcatttcc ccttctacta cctgttggct aatttagctg ctgccgattt cttcgctgga    240
attgcctatg tattcctgat gtttaacaca ggcccagttt caaaaacttt gactgtcaac    300
cgctggtttc tccgtcaggg gcttctggac agtagcttga ctgcttccct caccaacttg    360
ctggttatcg ccgtggagag gcacatgtca atcatgagga tgcgggtcca tagcaacctg    420
accaaaaaga gggtgacact gctcattttg cttgtctggg ccatcgccat ttttatgggg    480
gcggtcccca cactgggctg gaattgcctc tgcaacatct ctgcctgctc ttccctggcc    540
cccatttaca gcaggagtta ccttgttttc tggacagtgt ccaacctcat ggccttcctc    600
atcatggttg tggtgtacct gcggatctac gtgtacgtca agaggaaaac caacgtcttg    660
tctccgcata caagtgggtc catcagccgc cggaggacac ccatgaagct aatgaagacg    720
gtgatgactg tcttaggggc gtttgtggta tgctggaccc cgggcctggt ggttctgctc    780
ctcgacggcc tgaactgcag gcagtgtggc gtgcagcatg tgaaaaggtg gttcctgctg    840
ctggcgctgc tcaactccgt cgtgaacccc atcatctact cctacaagga cgaggacatg    900
tatggcacca tgaagaagat gatctgctga ttctctcagg agaacccaga gaggcgtccc    960
tctcgcatcc cctccacagt cctcagcagg agtgacacag gcagacagta catagaggat   1020
agtattagcc aaggtgcagt ctgcaataaa agcacttcct aa                      1062
```

The encoded EDG-7 (LPA₃) receptor has an amino acid sequence according to SEQ. ID. No. 6 as follows:

```
MNECHYDKHM DFFYNRSNTD TVDDWTGTKL VIVLCVGTFF CLFIFFSNSL VIAAVIKNRK   60

FHFPFYYLLA NLAAADFFAG IAYVFLMFNT GPVSKTLTVN RWFLRQGLLD SSLTASLTNL  120

LVIAVERHMS IMRMRVHSNL TKKRVTLLIL LVWAIAIFMG AVPTLGWNCL CNISACSSLA  180

PIYSRSYLVF WTVSNLMAFL IMVVVYLRIY VYVKRKTNVL SPHTSGSISR RRTPMKLMKT  240

VMTVLGAFVV CWTPGLVVLL LDGLNCRQCG VQHVKRWFLL LALLNSVVNP IIYSYKDEDM  300

YGTMKKMICC FSQENPERRP SRIPSTVLSR SDTGSQYIED SISQGACCNK STS         353
```

The nucleotide and amino acid sequences for PSP-24 is known and reported in Kawasawa et al. (2000) and Genbank Accession No. AB030566. A PSP-24 encoding nucleic acid molecule has a nucleotide sequence according to SEQ. ID. No. 7 as follows:

```
atggtcttct cggcagtgtt gactgcgttc cataccggga catccaacac aacatttgtc   60
gtgtatgaaa acacctacat gaatattaca ctccctccac cattccagca tcctgacctc  120
agtccattgc ttagatatag ttttgaaacc atggctccca ctggtttgag ttccttgacc  180
gtgaatagta cagctgtgcc cacaacacca gcagcattta agagcctaaa cttgcctctt  240
cagatcaccc tttctgctat aatgatattc attctgtttg tgtcttttct tgggaacttg  300
gttgtttgcc tcatggttta ccaaaaagct gccatgaggt ctgcaattaa catcctcctt  360
gccagcctag cttttgcaga catgttgctt gcagtgctga acatgccctt tgccctggta  420
actattctta ctacccgatg gattttgggg aaattcttct gtagggtatc tgctatgttt  480
ttctggttat ttgtgataga aggagtagcc atcctgctca tcattagcat agataggttc  540
cttattatag tccagaggca ggataagcta aacccatata gagctaaggt tctgattgca  600
gtttcttggg caacttcctt ttgtgtagct tttcctttag ccgtaggaaa ccccgacctg  660
cagatacctt cccgagctcc ccagtgtgtg tttgggtaca caaccaatcc aggataccag  720
gcttatgtga ttttgatttc tctcatttct ttcttcatac ccttcctggt aatactgtac  780
tcatttatgg gcatactcaa cacccttcgg cacaatgcct tgaggatcca tagctaccct  840
gaaggtatat gcctcagcca ggccagcaaa ctgggtctca tgagtctgca gagacctttc  900
cagatgagca ttgacatggg ctttaaaaca cgtgccttca ccactatttt gattctcttt  960
gctgtcttca ttgtctgctg ggcccccatt accacttaca gccttgtggc aacattcagt 1020
aagcactttt actatcagca caactttttt gagattagca cctggctact gtggctctgc 1080
tacctcaagt ctgcattgaa tccgctgatc tactactgga ggattaagaa attccatgat 1140
gcttgcctgg acatgatgcc taagtccttc aagtttttgc cgcagctccc tggtcacaca 1200
aagcgacgga tacgtcctag tgctgtctat gtgtgtgggg aacatcggac ggtggtgtga 1260
```

The encoded PSP-24 receptor has an amino acid sequence according to SEQ. ID. No. 8 as follows:

```
MFFSAVLTAF HTGTSNTTFV VYENTYMNIT LPPPFQHPDL SPLLRYSFET MAPTGLSSLT   60

VNSTAVPTTP AAFKSLNLPL QITLSAIMIF ILFVSFLGNL VVCLMVYQKA AMRSAINILL  120

ASLAFADMLL AVLNMPFALV TILTTRWIFG KFFCRVSAMF FWLFVIEGVA ILLIISIDRF  180

LIIVQRQDKL NPYRAKVLIA VSWATSFCVA FPLAVGNPDL QIPSPAPQCV FGYTTMPGYQ  240

AYVILISLIS FFIPPFLVILY SFMGILNTLR HNALRIHSYP EGICLSQASK LGLMSLQRPF  300
```

```
-continued
QMSIDMGFKT RAFTTILILF AVFIVCWAPF TTYSLVATFS KHFYYQHNFF EISTWLLWLC    360

YLKSALNPLI YYWRIKKFHD ACLDMMPKSF KFLPQLPGHT KRRIRPSAVY VCGEHRTVV     419
```

LPA receptor agonists will characteristically induce LPA-like activity from an LPA receptor, which can be measured either chemically, e.g., $Ca^{2+}$ or $Cl^-$ current in oocytes, or by examining changes in cell morphology, mobility, proliferation, etc. In contrast, LPA receptor antagonists will characteristically block LPA-like activity from an LPA receptor. This too can be measured either chemically, e.g., $Ca^{2+}$ or $Cl^-$ current in oocytes, or by examining changes in cell morphology, mobility, proliferation, etc.

By virtue of the compounds of the present invention acting as LPA receptor antagonists, the present invention also relates to a method of inhibiting LPA-induced activity on an LPA receptor. This method includes providing a compound of the present invention which has activity as an LPA receptor antagonist and contacting an LPA receptor with the compound under conditions effective to inhibit LPA-induced activity of the LPA receptor. The LPA receptor can be as defined above. The LPA receptor is present on a cell which normally expresses the receptor or which heterologously expresses the receptor. The contacting of the LPA receptor with the compound of the present invention can be performed either in vitro or in vivo.

As noted above, LPA is a signaling molecule involved in a number of different cellular pathways which involve signaling through LPA receptors, including those LPA receptors described above. Therefore, it is expected that the compounds of the present invention will modulate the effects of LPA on cellular behavior, either by acting as LPA receptor antagonists or LPA receptor agonists.

One aspect of the present invention relates to a method of treating cancer which includes providing a compound of the present invention and administering an effective amount of the compound to a patient in a manner effective to treat cancer. The types of cancer which can be treated with the compounds of the present invention include those cancers characterized by cancer cells whose behavior is attributable at least in part to LPA-mediated activity. Typically, these types of cancer are characterized by cancer cells which express one or more types of LPA receptors. Exemplary forms of cancer include, without limitation, prostate cancer, ovarian cancer, and bladder cancer.

The compounds of the present invention which are particularly useful for cancer treatment are the LPA receptor antagonists.

When administering the compounds of the present invention, they can be administered systemically or, alternatively, they can be administered directly to a specific site where cancer cells are present. Thus, administering can be accomplished in any manner effective for delivering the compound to cancer cells. LPA receptor antagonists, upon binding to LPA receptors, inhibit proliferation or metastasis of the cancer cells or destroy those cancer cells. As shown in Example 12, several LPA antagonist compounds of the present invention were cytotoxic to prostate cancer cell lines which express one or more LPA receptors of the type described above.

When the LPA antagonist compounds or pharmaceutical compositions of the present invention are administered to treat cancer, the pharmaceutical composition can also contain, or can be administered in conjunction with, other therapeutic agents or treatment regimen presently known or hereafter developed for the treatment of various types of cancer.

Cancer invasion is a complex multistep process in which individual cells or cell clusters detach from the primary tumor and reach the systemic circulation or the lymphatics to spread to different organs (Liotta et al., 1987). During this process, tumor cells must arrest in capillaries, extravasate, and migrate into the stroma of the tissue to make secondary foci. First, tumor cells must recognize signals on the endothelial cell that arrest them from the circulation. Second, tumor cells must attach to the basement membrane glycoprotein laminin via the cell surface laminin receptors. Following attachment to the basement membrane, tumor cells secrete proteases to degrade the basement membrane. Following attachment and local proteolysis, the third step of invasion is tumor cell migration. Cell motility plays a central role in tumor cell invasion and metastasis. The relationship between motility of tumor cells in vitro and the metastatic behavior in animal experiments indicates a strong direct correlation (Hoffman-Wellenhof et al., 1995). It is a well-documented fact that PLGFs promote proliferation and increase invasiveness of cancer cell in vitro. Imamura and colleagues established that cancer cells require serum factors for their invasion (Imamura et al., 1991), and later identified LPA as the most important serum component that is fully capable of restoring tumor cell invasion in serum-free systems (Xu et al., 1995a; Imamura et al., 1993; Mukai et al., 1993).

It has been shown that PLGFR are expressed in ovarian cancer cell lines; namely, OCC1 and HEY cells. Specifically, RT-PCR analyses show the presence of EDG-2 and EDG-7 receptors in these cell lines. Recently, Im et al. (2000) demonstrated that EDG-7 is expressed in prostate cancer cell lines; namely, PC-3 and LNCaP cells. RT-PCR analysis on the prostate cancer cell lines DU-145, PC-3, and LNCaP lines showed that EDG-2, 4, 5, and EDG-7 are present in all three prostate cancer cell lines, whereas EDG-3 is present in LNCaP and DU-145 prostate cancer cell lines.

Another aspect of the present invention relates to a method of enhancing cell proliferation. This method of enhancing cell proliferation includes the steps of providing a compound of the present invention which has activity as an agonist of an LPA receptor and contacting the LPA receptor on a cell with the compound in a manner effective to enhance LPA receptor-induced proliferation of the cell.

In addition to the roles that LPA plays in modulating cancer cell activity, there is strong evidence to suggest that LPA also has a physiological role in natural wound healing. At wound sites, LPA derived from activated platelets is believed to be responsible, at least in part, for stimulating cell proliferation at the site of injury and inflammation possibly in synchronization with other platelet-derived factors (Balazs et al., 2000). Moreover, LPA by itself stimulates platelet aggregation, which may in turn be the factor that initiates an element of positive feedback to the initial aggregatory response (Schumacher et al., 1979; Tokumura et al., 1981; Gerrard et al., 1979; Simon et al., 1982).

Due to the role of LPA in cell proliferation, compounds having LPA receptor agonist activity can be used in a manner effective to promote wound healing. Accordingly, another aspect of the present invention relates to a method of treating a wound. This method is carried out by providing a compound of the present invention which has activity as an agonist of an LPA receptor and delivering an effective amount of the compound to a wound site, where the compound binds to LPA receptors on cells that promote healing of the wound, thereby stimulating LPA receptor agonist-induced cell proliferation to promote wound healing.

The primary goal in the treatment of wounds is to achieve wound closure. Open cutaneous wounds represent one major category of wounds and include burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age (see Hunt and Goodson, 1988).

Phospholipids have been demonstrated to be important regulators of cell activity, including mitogenesis (Xu et al., 1995b), apoptosis, cell adhesion, and regulation of gene expression. Specifically, for example, LPA elicits growth factor-like effects on cell proliferation (Moolenaar, 1996) and cell migration (Imamura et al., 1993). It has also been suggested that LPA plays a role in wound healing and regeneration (Tigyi and Miledi, 1992).

In general, agents which promote a more rapid influx of fibroblasts, endothelial and epithelial cells into wounds should increase the rate at which wounds heal.

In vitro systems model different components of the wound healing process, for example the return of cells to a "wounded" confluent monolayer of tissue culture cells, such as fibroblasts (Verrier et al., 1986), endothelial cells (Miyata et al., 1990) or epithelial cells (Kartha et al., 1992). Other systems permit the measurement of endothelial cell migration and/or proliferation (Muller et al., 1987; Sato et al., 1988).

In vivo models for wound healing are also well-known in the art, including wounded pig epidermis (Ohkawara et al., 1977) or drug-induced oral mucosal lesions in the hamster cheek pouch (Cherrick et al., 1974).

The compounds of the present invention which are effective in wound healing can also be administered in combination, i.e., in the pharmaceutical composition of the present invention or simultaneously administered via different routes, with a medicament selected from the group consisting of an antibacterial agent, an antiviral agent, an antifungal agent, an antiparasitic agent, an antiinflammatory agent, an analgesic agent, an antipruritic agent, or a combination thereof.

For wound healing, a preferred mode of administration is by the topical route. However, alternatively, or concurrently, the agent may be administered by parenteral, subcutaneous, intravenous, intramuscular, intraperitoneal or transdermal routes. Alternatively, or concurrently, administration may be by the oral route. The dosage administered will be dependent upon the age, health, and weight of the recipient, kind of concurrent treatment, if any, frequency of treatment, and the nature of the effect desired.

For the preferred topical applications, especially for treatment of humans and animals having a wound, it is preferred to administer an effective amount of a compound according to the present invention to the wounded area, e.g., skin surfaces. This amount will generally range from about 0.001 mg to about 1 g per application, depending upon the area to be treated, the severity of the symptoms, and the nature of the topical vehicle employed. A preferred topical preparation is an ointment wherein about 0.01 to about 50 mg of active ingredient is used per ml of ointment base, such as PEG-1000.

The present invention further provides methods of inhibiting apoptosis or preserving or restoring cell, tissue or organ function. This method is carried out by providing a compound of the present invention which has activity as an agonist of an LPA receptor and contacting a cell, tissue, or organ with an amount of the compound which is effective to inhibit apoptosis, or preserve or restore function in the cell, tissue, or organ. The contacting can be carried out in vitro (i.e., during cell culture or organ or tissue transfer) or in vivo (i.e., by administering the effective amount of the compound to a patient as indicated below).

Various indications which can be treated, include, but are not limited to, those related to apoptosis, ischemia, traumatic injury, and reperfusion damage. Those conditions related to apoptosis include, but are not limited to, dermatological effects of aging, the effects of reperfusion after an ischemic event, immunosuppression, gastrointestinal perturbations, cardiovascular disorders, rejection of tissue transplantation, wound healing, and Alzheimer's disease. The treatment can also diminish the apoptosis-related problems associated with viral infection, chemotherapeutic agents, radiation, and immunosuppressive drugs. These stimuli trigger apoptosis in a variety of disorders, including, but not limited to, those of the digestive tract tissues.

A preferred compound for practicing this aspect of the present invention is compound 8 g, particularly with respect to the protection of gastroendothelial cells against chemotherapeutic- or radiation-induced apoptosis as described in the Examples herein.

The treatments are also suitable during all phases of organ transplantation. The compounds having agonist activity on an LPA receptor can be used to prepare the organ by administering an amount of the compound to the donor effective to stabilize or preserve the organ. The organ can be perfused and/or preserved in OPS containing the compound. The organ recipient can then be administered an amount of the compound effective to enhance organ stability and function. The compositions are also particularly suitable for use in treating cardioplegia, whether related to transplantation or other surgical intervention.

Gastrointestinal tissue damage includes, but is not limited to, damage to the lining of the gut, severe chronic ulcers, colitis, radiation induced damage, chemotherapy induced damage, and the perturbation of the gastrointestinal tract caused by parasites, and diarrhea from any other cause. Various viral and bacterial infections are known to result in gastrointestinal perturbations. The compounds having agonist activity on an LPA receptor are also suitable for use in treatment of the side effects associated with these infections. Such compounds are particularly suited for use in ameliorating the gastrointestinal disturbances associated with chemotherapy. Thus, such compounds are suitable for use not only in preventing the diarrhea associated with chemotherapy but also the nausea.

These compounds are particularly suited to treatment of various gastrointestinal conditions in animals, including, but not limited to livestock and domesticated animals. Such conditions, particularly diarrhea, account for the loss of many calves and puppies to dehydration and malnutrition. Treatment of gastrointestinal conditions is preferably by gastrointestinal administration. In the case of cattle and domesticated animals, an effective amount of these compounds can be conveniently mixed in with the feed. In humans, administration can be by any method known in the art of gastrointestinal administration. Preferably, administration is oral.

In addition, the compounds having agonist activity on an LPA receptor can be administered to immunodeficient patients, particularly HIV-positive patients, to prevent or at least mitigate apoptotic death of T cells associated with the condition, which results in the exacerbation of immunodeficiencies as seen in patients with AIDS. Preferably, administration to such patients is parenteral, but can also be transdermal or gastrointestinal.

The compounds having agonist activity on an LPA receptor can also be administered to treat apoptosis associated with reperfusion damage involved in a variety of conditions, including, but not limited to, coronary artery obstruction; cerebral infarction; spinal/head trauma and concomitant severe paralysis; reperfusion damage due to other insults such as frostbite, coronary angioplasty, blood vessel attachment, limb attachment, organ attachment and kidney reperfusion.

Myocardial and cerebral infarctions (stroke) are caused generally by a sudden insufficiency of arterial or venous blood supply due to emboli, thrombi, or pressure that produces a macroscopic area of necrosis; the heart, brain, spleen, kidney, intestine, lung and testes are likely to be affected. Cell death occurs in tissue surrounding the infarct upon reperfusion of blood to the area; thus, the compositions are effective if administered at the onset of the infarct, during reperfusion, or shortly thereafter. The present invention includes methods of treating reperfusion damage by administering a therapeutically effective amount of the compounds having agonist activity on an LPA receptor to a patient in need of such therapy.

The invention further encompasses a method of reducing the damage associated with myocardial and cerebral infarctions for patients with a high risk of heart attack and stroke by administering a therapeutically effective amount of the compounds having agonist activity on an LPA receptor to a patient in need of such therapy. Preferably, treatment of such damage is by parenteral administration of such compounds. Any other suitable method can be used, however, for instance, direct cardiac injection in the case of myocardial infarct. Devices for such injection are known in the art, for instance the Abojet cardiac syringe.

The invention further provides methods of limiting and preventing apoptosis in cells, or otherwise preserving cells, during the culture or maintenance of mammalian organs, tissues, and cells, by the addition of an effective amount of the compounds having agonist activity on an LPA receptor to any media or solutions used in the art of culturing or maintaining mammalian organs, tissues, and cells.

The invention further encompasses media and solutions known in the art of culturing and maintaining mammalian organs, tissues and cells, which include an amount of the compounds having agonist activity on an LPA receptor which is effective to preserve or restore cell, tissue or organ function, or limit or prevent apoptosis of the cells in culture. These aspects of the invention encompass mammalian cell culture media including an effective amount of at least one compounds having agonist activity on an LPA receptor and the use of such media to preserve or restore cell, tissue or organ function, or to limit or prevent apoptosis in mammalian cell culture. An effective amount is one which decreases the rate of apoptosis and/or preserves the cells, tissue or organ. Such compounds can limit or prevent apoptosis under circumstances in which cells are subjected to mild traumas which would normally stimulate apoptosis. Exemplary traumas can include, but are not limited to, low level irradiation, thawing of frozen cell stocks, rapid changes in the temperature, pH, osmolarity, or ion concentration of culture media, prolonged exposure to non-optimal temperature, pH, osmolarity, or ion concentration of the culture media, exposure to cytotoxins, disassociation of cells from an intact tissue in the preparation of primary cell cultures, and serum deprivation (or growth in serum-free media).

Thus, the invention encompasses compositions comprising tissue culture medium and an effective amount of the compounds having agonist activity on an LPA receptor. Serum-free media to which the compositions can be added as anti-apoptotic media supplements include, but are not limited to, AIM VP Media, Neuman and Tytell's Serumless Media, Trowell's T8 Media, Waymouth's MB 752/1 and 705/1 Media, and Williams' Media E. In addition to serum-free media, suitable mammalian cell culture media to which the compounds having agonist activity on an LPA receptor can be added as anti-apoptotic media supplements include, but are not limited to, Basal Media Eagle's, Fischer's Media, McCoy's Media, Media 199, RPMI Media 1630 and 1640, Media based on F-10 & F-12 Nutrient Mixtures, Leibovitz's L-15 Media, Glasgow Minimum Essential Media, and Dulbecco's Modified Eagle Media. Mammalian cell culture media to which the compounds having agonist activity on an LPA receptor can be added further include any media supplement known in the art. Exemplary supplements include, but are not limited to, sugars, vitamins, hormones, metalloproteins, antibiotics, antimycotics, growth factors, lipoproteins, and sera.

The invention further encompasses solutions for maintaining mammalian organs prior to transplantation, which solutions include an effective amount of the compounds having agonist activity on an LPA receptor, and the use of such solutions to preserve or restore organ function or to limit or prevent apoptosis in treated mammalian organs during their surgical removal and handling prior to transplantation. The solutions can be used to rush, perfuse and/or store the organs. In all cases, concentrations of the compounds (having agonist activity on an LPA receptor) required to limit or prevent damage to the organs can be determined empirically by one skilled in the art by methods known in the art.

In addition to the foregoing, the compounds having agonist activity on an LPA receptor can be topically applied to the skin to treat a variety of dermatologic conditions. These conditions include, but are not limited to, hair loss and wrinkling due to age and/or photo damage. The present invention also encompasses, therefore, methods of treating dermatological conditions. In particular, hair loss can be caused by apoptosis of the cells of the hair follicles (Stenn et al., 1994). Therefore, the compounds having agonist activity on an LPA receptor are suitable for use in topical treatment of the skin to prevent continued hair loss.

The various dermatologic conditions are preferably treated by topical application of an effective amount of a compound having agonist activity on an LPA receptor (or compositions which contain them). An effective amount of such compounds is one which ameliorates or diminishes the symptoms of the dermatologic conditions. Preferably, the treatment results in resolution of the dermatologic condition or restoration of normal skin function; however, any amelioration or lessening of symptoms is encompassed by the invention.

EXAMPLES

The following examples are intended to illustrate, but by no means are intended to limit, the scope of the present invention as set forth in the appended claims.

General Methods

All reagents were purchased from Sigma-Aldrich Chemical Co., Fisher Scientific (Pittsburgh, Pa.), Bedukian Research (Danbury, Conn.) and Toronto Research Chemicals (North York, ON, Canada) and were used without further purification. Phosphonate analogs were purchased from Lancaster (Pelham, N.H.; n-decyl-phosphonate (9a)), PolyCarbon (Devens, Mass.; n-dodecyl-phosphonate (9b)), Alfa Aesar (Ward Hill, Mass.; n-tetradecyl-phosphonate (9c) and n-octadecyl-phosphonate (9d)). LPA 18:1, DGPP, Ser-PA, and Tyr-PA were obtained from Avanti Polar Lipids (Alabaster, Ala.). Melting points were determined on a Thomas-Hoover capillary melting point apparatus and are uncorrected. Routine thin-layer chromatography (TLC) was performed on 250 μM glassbacked UNIPLATES (Analtech, Newark, Del.). Flash chromatography was performed on pre-packed silica gel columns using a Horizon HPFC system (Biotage, Charlottesville, Va.). $^1$H and $^{31}$P NMR spectra were obtained on a Bruker AX 300 (Billerica, Mass.) spectrometer. Chemical shifts for $^1$H NMR are reported as parts per million (ppm) relative to TMS. Chemical shifts for $^{31}$P NMR are reported as parts per million (ppm) relative to 0.0485 M triphenylphosphate in $CDCl_3$. Mass spectral data was collected on a Bruker ESQUIRE electrospray/ion trap instrument in the positive and negative ion modes. Elemental analyses were performed by Atlantic Microlab Inc., Norcross, Ga.

Example 1

Synthesis of Phosphoric Acid di-tert-butyl Ester Alkenyl Esters (4a-f)

Commercially available unsaturated fatty alcohols (3a-f) were used as starting materials. To a stirred solution of alcohol (2.5 mmol) and di-tert-butyl-N,N-diisopropyl phosphoramidite (1.51 g, 4 mmol) in methylene chloride (60 mL) was added 1H-tetrazole (578 mg, 8.25 mmol). After 30 minutes of stirring the mixture was cooled to 0° C. and 0.3 mL of 50% hydrogen peroxide was added. The mixture was stirred for 1 h., diluted with methylene chloride (100 mL), washed with 10% sodium metabisulfite (2×50 ml), saturated sodium bicarbonate (2×50 ml), water (50 ml), and brine (50 ml). The organic layer was dried over anhydrous sodium sulfate, filtered, and concentrated under vacuum. The resulting crude products were purified by silica gel chromatography using hexane/ethyl acetate (7:3) to elute the desired products, di-t-Boc protected fatty alcohol phosphates (4a-f).

Phosphoric acid di-tert-butyl ester dec-9-enyl ester (4a): Isolated as clear oil (75% yield). $^1$H NMR ($CDCl_3$): δ5.80 (m, 1H), 4.95 (m, 2H), 3.95 (q, J=7.5 Hz, 2H), 2.03 (q, J=7.1 Hz, 2H), 1.65 (quintet, 2H), 1.48 (s, 18H), 1.30 (br s, 10H); $^{31}$P NMR ($CDCl_3$): δ7.90; MS: [M+$^{23}$Na] at m/z 371.3.

Phosphoric acid di-tert-butyl ester dec-4-enyl ester (4b): Isolated as clear oil (68% yield). $^1$H NMR ($CDCl_3$): δ5.25 (m, 2H), 3.84 (q, J=6.8 Hz, 2H), 2.05 (q, J=7.0 Hz, 2H), 1.98 (q, J=6.8 Hz, 2H), 1.61 (quintet, 2H), 1.42 (s, 18H), 1.22 (br s, 6H), 0.80 (t, J=7.2 Hz, 3H); $^{31}$P NMR (MeOH-$d_4$): δ7.90; MS: [M+$^{23}$Na] at m/z 371.3.

Phosphoric acid di-tert-butyl ester dodec-9-enyl ester (4c): Isolated as clear oil (70% yield). $^1$H NMR ($CDCl_3$): δ5.26 (m, 2H), 3.88 (q, J=6.6 Hz, 2H), 1.94 (m, 4H), 1.59 (quintet, 2H), 1.42 (s, 18H), 1.24 (br s, 10H), 0.89 (t, J=7.5 Hz, 3H); $^{31}$P NMR ($CDCl_3$): δ7.80; MS: [M+$^{23}$Na] at m/z 399.5.

Phosphoric acid di-tert-butyl ester tetradec-9-enyl ester (4d): Isolated as clear oil (68% yield). $^1$H NMR ($CDCl_3$): δ5.34 (t, J=5.2 Hz, 2H), 3.94 (q, J=6.6 Hz, 2H), 2.01 (m, 4H), 1.65 (quintet, 2H), 1.48 (s, 18H), 1.30 (br s, 18H), 0.90 (t, J=7.4 Hz, 3H); $^{31}$P NMR ($CDCl_3$): δ7.90; MS: [M+$^{23}$ Na] at m/z 427.4.

Phosphoric acid di-tert-butyl ester tetradec-11-enyl ester (4e): Isolated as clear oil (82% yield). $^1$H NMR ($CDCl_3$): δ5.34 (m, 2H), 3.94 (q, J=6.5 Hz, 2H), 2.01 (m, 4H), 1.65 (quintet, 2H), 1.48 (s, 18H), 1.23 (br s, 14H), 0.95 (t, J=7.4 Hz, 3H); $^{31}$P NMR ($CDCl_3$): δ8.10; MS: [M+$^{23}$Na] at m/z 427.4.

Phosphoric acid di-tert-butyl ester octadec-9-enyl ester (4f): Isolated as clear oil (72% yield). $^1$H NMR ($CDCl_3$): δ5.34 (m, 2H), 3.94 (q, J=6.9 Hz, 2H), 2.01 (m, 4H), 1.66 (quintet, 2H), 1.48 (s, 18H), 1.28 (br s, 22H), 0.88 (t, J=6.6 Hz, 3H); $^{31}$P NMR ($CDCl_3$): δ8.10; MS: [M+$^{23}$ Na] at m/z 483.5.

Example 2

Synthesis of Phosphoric Acid Mono Alkenyl Esters (5a-f)

The Boc-protected FAPs (4a-f) were deprotected with TFA to yield the corresponding unsaturated FAPs (5a-f). To a solution of 100 mg of 1a-6a in methylene chloride (20 mL), trifluoroacetic acid (0.3 mL) was added. The mixture was allowed to stir for 4 h., and TLC showed the completion of the reaction. Solvents were evaporated; the residue was washed with methylene chloride (2×20 mL), and concentrated under vacuum to yield the desired phosphoric acid mono alkenyl esters as colorless oils.

Phosphoric acid monodec-9-enyl ester (5a): Isolated as an oil (85%). $^1$H NMR (MeOH-$d_4$): δ5.74 (m, 1H), 4.88 (m, 2H), 3.90 (q, J=6.6 Hz, 2H), 2.01 (q, J=6.9 Hz, 2H), 1.61 (quintet, 2H), 1.28 (br s, 10H); $^{31}$P NMR (MeOH-$d_4$): δ17.84; MS: [M-H]— at m/z 235.2. Anal. ($C_{10}H_{21}O_4P.0.1H_2O$)C, H.

Phosphoric acid monodec-4-enyl ester (5b): Isolated as an oil (78%). $^1$H NMR (MeOH-$d_4$): δ5.31 (m, 2H), 3.84 (q, J=6.8 Hz, 2H), 2.05 (q, J=7.0 Hz, 2H), 1.98 (q, J=6.8 Hz, 2H), 1.61 (quintet, 2H), 1.22 (br s, 6H), 0.80 (t, J=7.2 Hz, 3H); $^{31}$P NMR (MeOH-$d_4$): δ17.45; MS: [M-H]— at m/z 235.2. Anal. ($C_{10}H_{21}O_4P.0.5H_2O$)C, H.

Phosphoric acid monododec-9-enyl ester (5c): Isolated as an oil (82%). $^1$H NMR (DMSO/MeOH-$d_4$): δ5.28 (m, 2H), 3.82 (q, J=6.6 Hz, 2H), 1.96 (m, 4H), 1.54 (m, 2H), 1.25 (br s, 10H), 0.88 (t, J=7.2 Hz, 3H); $^{31}$P NMR (MeOH-$d_4$): Δ 16.22; MS: [M-H]— at m/z 263.0. Anal. ($C_{12}H_{25}O_4P.0.6H_2O$)C, H.

Phosphoric acid monotetradec-9-enyl ester (5d): Isolated as an oil (84%). $^1$H NMR ($CDCl_3$/MeOH-$d_4$): δ5.21 (m, 2H), 3.84 (q, J=6.5 Hz, 2H), 1.91 (m, 4H), 1.54 (m, 2H), 1.20 (br s, 14H), 0.78 (m, 3H); $^{31}$P NMR (MeOH-$d_4$): Δ 16.20; MS: [M-H]— at m/z 291.4. Anal. ($C_{14}H_{29}O_4P.0.25H_2O$)C, H.

Phosphoric acid monotetradec-11-enyl ester (5e): Isolated as an oil (78%). $^1$H NMR (MeOH-$d_4$): δ5.24 (m, 2H), 3.88 (q, J=6.6 Hz, 2H), 1.95 (m, 4H), 1.58 (m, 2H), 1.25 (br s, 14H), 0.86 (t, J=7.1 Hz, 3H); $^{31}$P NMR (MeOH-$d_4$): δ16.20; MS: [M-H]— at m/z 291.3. Anal. ($C_{14}H_{29}O_4P$)C, H.

Phosphoric acid monooctadec-9-enyl ester (5f): Isolated as an oil (86%). $^1$H NMR (MeOH-$d_4$): δ5.30 (m, 2H), 3.91 (q, J=6.6 Hz, 2H), 2.00 (m, 4H), 1.62 (quintet, 2H), 1.26 (br s, 22H), 0.86 (t, J=6.0 Hz, 3H); $^{31}$P NMR (MeOH-$d_4$): δ16.21; MS: [M-H]— at m/z 347.4. Anal. ($C_{18}H_{37}O_4P.0.4H_2O$)C, H.

Example 3

Synthesis of Thiophosphoric Acid O,O'-bis-(2-cyano-ethyl) Ester O''-alkyl/alkenyl Esters (7a-g)

Commercially available saturated or unsaturated fatty alcohols (6a-g) were used as starting materials. A solution of alcohol (2.0 mmol), bis-(2-cyanoethyl)-N,N-diisopropyl phosphoramidite (1.085 g, 4 mmol) and 1H-tetrazole (420 mg, 6 mmol) was stirred for 30 minutes at room temperature, followed by the addition of elemental sulfur (200 mg) and the mixture was refluxed for 2 h. The reaction mixture was cooled to room temperature and solvents were evaporated under vacuum. Addition of ethyl acetate (30 mL) precipitated excess sulfur, which was filtered out, and the solvent was evaporated to give the crude mixture. The mixture was purified by flash chromatography to give the desired products as colorless oils.

Thiophosphoric acid O,O'-bis-(2-cyano-ethyl) ester O"-decyl ester (7a): Isolated as colorless oil (72% yield). $^1$H NMR (CDCl$_3$): δ4.21-4.35 (m, 4H), 4.12 (m, 2H), 2.8 (t, J=6.3 Hz, 4H), 1.68 (quintet, 2H), 1.26 (br s, 14H), 0.88 (t, J=6.0 Hz, 3H); MS: [M+$^{23}$Na] at m/z 383.4.

Thiophosphoric acid O,O'-bis-(2-cyano-ethyl) ester O"-dodecyl ester (7b): Isolated as colorless oil (84% yield). $^1$H NMR (CDCl$_3$): δ4.26-4.33 (m, 4H), 4.12 (m, 2H), 2.8 (t, J=6.2 Hz, 4H), 1.71 (quintet, 2H), 1.26 (br s, 14H), 0.88 (t, J=6.6 Hz, 3H); MS: [M+$^{23}$Na] at m/z 411.4.

Thiophosphoric acid O,O'-bis-(2-cyano-ethyl) ester O"-tetradecyl ester (7c): Isolated as clear oil (82% yield). $^1$H NMR (CDCl$_3$): δ4.25-4.33 (m, 4H), 4.12 (m, 2H), 2.8 (t, J=6.0 Hz, 4H), 1.71 (quintet, 2H), 1.26 (br s, 18H), 0.88 (t, J=6.6 Hz, 3H); MS: [M+$^{23}$Na] at m/z 439.5.

Thiophosphoric acid O,O'-bis-(2-cyano-ethyl) ester O"-dec-9-enyl ester (7d): Isolated as clear oil (76% yield). $^1$H NMR (CDCl$_3$): δ5.81 (m, 1H), 4.96 (m, 2H), 4.22-4.32 (m, 4H), 4.11 (m, 2H), 2.8 (t, J=6.3 Hz, 4H), 2.01 (t, J=6.6 Hz, 4H), 1.70 (quintet, 2H), 1.31 (br s, 10H); MS: [M+$^{23}$Na] at m/z 381.3.

Thiophosphoric acid O,O'-bis-(2-cyano-ethyl) ester O"-dodec-9-enyl ester (7e): Isolated as clear oil (80% yield). $^1$H NMR (CDCl$_3$): δ5.34 (m, 2H), 4.25-4.33 (m, 4H), 4.11 (m, 2H), 2.8 (t, J=6.0 Hz, 4H), 2.07 (m, 2H), 1.70 (quintet, 2H), 1.31 (br s, 10H), 0.96 (t, J=7.5 Hz, 3H); MS: [M+$^{23}$Na] at m/z 409.5.

Thiophosphoric acid O,O'-bis-(2-cyano-ethyl) ester O"-tetradec-9-enyl ester (7f): Isolated as clear oil (75% yield). $^1$H NMR (CDCl$_3$): δ5.35 (m, 2H), 4.25-4.33 (m, H), 4.12 (m, 2H), 2.78 (t, J=6.0 Hz, 4H), 2.02 (m, 2H), 1.71 (quintet, 2H), 1.31 (br s, 14H), 0.90 (t, J=7.2 Hz, 3H); MS: [M+$^{23}$Na] at m/z 437.5.

Thiophosphoric acid O,O'-bis-(2-cyano-ethyl) ester O"-octadec-9-enyl ester (7 g): Isolated as clear oil (72% yield). $^1$H NMR (CDCl$_3$): δ5.35 (m, 2H), 4.27-4.31 (m, 4H), 4.12 (m, 2H), 2.78 (t, J=6.0 Hz, 4H), 2.02 (m, 2H), 1.71 (quintet, 2H), 1.27 (br s, 22H), 0.88 (t, J=7.2 Hz, 3H); MS: [M+$^{23}$ Na] at m/z 493.5.

Example 4

Synthesis of Thiophosphoric Acid O-alkyl/alkenyl Esters (8a-g)

Thiophosphoric acid O,O'-bis-(2-cyano-ethyl) ester O"-alkyl/alkenyl esters (7a-7 g) were used as starting materials. A solution of 100 mg of 7a-7 g in methanolic KOH (10 mL) was stirred for 2 h., and TLC showed the completion of the reaction. The solvent was evaporated to give the crude product, which was dissolved in water (20 mL), and acidified with HCl. The aqueous mixture was extracted with ethyl acetate (2×50 mL), organic layer was dried over sodium sulfate and concentrated under vacuum to give the desired compound as light yellow colored oil.

Thiophosphoric acid O-decyl ester (8a): Isolated as light yellow colored oil (80% yield). $^1$H NMR (DMSO): δ3.86 (m, 2H), 1.56 (quintet, 2H), 1.24 (br s, 14H), 0.86 (t, J=6.0 Hz, 3H); MS: [M-H]— at m/z 253.2. Anal. (C$_{10}$H$_{23}$O$_3$PS)C, H.

Thiophosphoric acid O-dodecyl ester (8b): Isolated as light yellow colored oil (73% yield). $^1$H NMR (DMSO): δ3.84 (m, 2H), 1.56 (quintet, 2H), 1.24 (br s, 18H), 0.83 (t, J=6.9 Hz, 3H); MS: [M-H]— at m/z 280.9. Anal. (C$_{12}$H$_{27}$O$_3$PS.0.5H$_2$O)C, H Thiophosphoric acid O-tetradecyl ester (8c): Isolated as light yellow colored oil (70% yield). $^1$H NMR (DMSO): δ3.85 (m, 2H), 1.56 (quintet, 2H), 1.24 (br s, 22H), 0.85 (t, J=6.0 Hz, 3H); MS: [M-H]— at m/z 309.4. Anal. (C$_{14}$H$_{31}$O$_3$PS.0.25H$_2$O)C, H.

Thiophosphoric acid O-dec-9-enyl ester (8d): Isolated as light yellow colored oil (76% yield). $^1$H NMR (DMSO): δ5.79 (m, 1H), 4.94 (m, 2H), 3.85 (m, 2H), 2.01 (q, J=6.6 Hz, 4H), 1.55 (quintet, 2H), 1.26 (br s, 10H); MS: [M-H]— at m/z 251.1. Anal. (C$_{10}$H$_{21}$O$_3$PS)C, H.

Thiophosphoric acid O-dodec-9-enyl ester (8e): Isolated as light yellow colored oil (80% yield). $^1$H NMR (DMSO): Δ 5.31 (m, 2H), 3.85 (q, J=6.6 Hz, 2H), 1.99 (m, 4H), 1.56 (quintet, 2H), 1.26 (br s, 10H), 0.91 (t, J=7.5 Hz, 3H); MS: [M-H]— at m/z 279.5. Anal. (C$_{12}$H$_{25}$O$_3$PS0.35H$_2$O)C, H.

Thiophosphoric acid O-tetradec-9-enyl ester (8f): Isolated as light yellow colored oil (72% yield). $^1$H NMR (DMSO): δ5.32 (m, 2H), 3.85 (m, 2H), 1.98 (m, 4H), 1.55 (quintet, 2H), 1.26 (br s, 14H), 0.86 (t, J=6.9 Hz, 3H); MS: [M-H]— at m/z 307.5. Anal. (C$_{14}$H$_{29}$O$_3$PS.0.3H$_2$O)C, H.

Thiophosphoric acid O-octadec-9-enyl ester (8 g): Isolated as light yellow colored oil (82% yield). $^1$H NMR (DMSO): δ5.32 (m, 2H), 3.85 (m, 2H), 1.97 (m, 4H), 1.55 (quintet, 2H), 1.24 (br s, 22H), 0.85 (t, J=6.9 Hz, 3H); MS: [M-H]— at m/z 363.5. Anal. (C$_{18}$H$_{37}$O$_3$PS.0.3H$_2$O)C, H.

Example 5

Synthesis of (1,1-Difluoro-pentadecyl) Phosphonic Acid Diethyl Ester (10)

To a solution of diethyl difluoromethanephosphonate (1.0 g, 5.316 mmol) in THF (50 mL) 2 M LDA (626 mg, 5.847 mmol) was added at −78° C. and stirred for 30 min. Tetradecyl bromide (1.474 g, 5.316 mmol) in THF (10 mL) was added to the mixture at −78° C. and the reaction mixture was stirred overnight. THF was evaporated and the residual oil was purified by flash chromatography using 30% ethyl acetate in hexane as eluent to give 817 mg (40%) of compound 10 as colorless oil. $^1$H NMR (CDCl$_3$): δ4.26 (m, 4H), 2.05 (m, 2H), 1.56 (m, 2H), 1.37 (t, J=6.9 Hz, 6H), 1.25 (br s, 22H), 0.87 (t, J=6.6 Hz, 3H); MS: [M+$^{23}$Na] at m/z 407.2.

Example 6

Synthesis of (1,1-Difluoro-pentadecyl) Phosphonic Acid (11)

To a solution of vacuum dried 10 (225 mg, 0.585 mmol) in methylene chloride (5 mL) bromotrimethyl silane (895 mg, 5.85 mmol) was added and the mixture was stirred at room temperature. TLC showed completion of the reaction after 6 h. Solvents were removed under reduced pressure, and the residue was stirred in 95% methanol (3 mL) for 1 h. The mixture was concentrated under reduced pressure, dried under vacuum to give 150 mg (78%) of 11 as light yellow solid. mp 66-69° C.; $_1$H NMR (CD$_3$OD): δ2.03 (m, 2H), 1.59

(m, 2H), 1.24 (br s, 22H), 0.90 (t, J=6.6 Hz, 3H); MS: [M-H]— at m/z 327.3. Anal. ($C_{15}H_3$)$F_2O_3P$.0.2$H_2O$)C, H.

Example 7

Analysis of Compounds for LPA Receptor Agonist or Antagonist Activity

Compounds were tested for their ability to induce or inhibit LPA-induced calcium transients in RH7777 rat hepatoma cells stably expressing $LPA_1$, $LPA_2$, and $LPA_3$ receptors and in PC-3 that express $LPA_{1-3}$ endogenously, using a FlexStation II automated fluorometer (Molecular Devices, Sunnyvale, Calif.) (Fischer et al., 2001; Virag et al., 2003). RH7777 cells stably expressing either $LPA_1$, $LPA_2$ or $LPA_3$ (Fischer et al 2001; Virag et al., 2003) or PC-3 cells were plated on poly-D lysine-coated black wall clear bottom 96-well plates (Becton Dickinson, San Jose, Calif.) with a density of 50000 cells/well, and cultured overnight. The culture medium (DMEM containing 10% FBS) was then replaced with modified Krebs solution (120 mM NaCl, 5 mM KCl, 0.62 mM $MgSO_4$, 1.8 mM $CaCl_2$, 10 mM HEPES, 6 mM glucose, pH 7.4) and the cells were serum starved for 6-8 hours (12 h for PC-3 cells). Cells were loaded with Fura-2 AM for 35 minutes in modified Krebs medium. The Fura-2 was removed before loading the plate in the FlexStation instrument by replacing the medium once again with 100 µl modified Krebs medium/well. Plates were incubated for 4 minutes in the instrument to allow for warming to 37° C. Changes in intracellular $Ca^{2+}$ concentration were monitored by measuring the ratio of emitted light intensity at 520 nm in response to excitation by 340 nm and 380 nm wavelength lights, respectively. Each well was monitored for 80-120 seconds. 50 µl of the test compound (3× stock solution in modified Krebs) was added automatically to each well 15 seconds after the start of the measurement. Time courses were recorded using the SoftMax Pro software (Molecular Devices, Sunnyvale, Calif.). $Ca^+$ transients were quantified automatically by calculating the difference between maximum and baseline ratio values for each well.

Selected compounds were tested for PPARγ activation in CV1 cells, transfected with an acyl-coenzyme A oxidase-luciferase (PPRE-Acox-Rluc) reporter gene construct as previously reported (Zhang et al., 2004). The assay of PPARγ activation in CV1 cells was run as reported in Zhang et al. Briefly, CV-1 cells were plated in 96-well plates (5×$10_3$ cells per well) in Dulbecco's modified Eagle's medium supplemented with 10% fetal bovine serum. The next day, the cells were transiently transfected with 125 ng of pGL3-PPRE-Acox-Rluc, 62.5 ng of pcDNAI-PPARγ, and 12.5 ng of pSV-β-galactosidase (Promega, Madison, Wis.) using LipofectAMINE 2000 (Invitrogen). Twenty-four hours after System (Promega) and the Galacto-Light Plus™ System (Applied Biosystems, Foster City, Calif.), respectively, samples were run in quadruplicate and the mean ±standard errors were calculated. Data are representative of at least two independent transfections. Student's t-test was used for null hypothesis testing and P<0.05 was considered transfection, cells were treated with 1% FBS supplemented OptiMEMI (Invitrogen) containing DMSO or 10 µM test compound dissolved in DMSO for 20 h. Luciferase and β-galactosidase activities were measured with the Steady-Glo® Luciferase Assay as significant (in the figures P<0.05 is denoted by * and P<0.01 is **).

According to the original two-point contact model (Wang et al., 2001; Sardar et al., 2002), both a polar phosphate head group and a hydrophobic tail are required for specific interactions with the LPA GPCRs (Fischer et al., 2001). The phosphate group was identified as a necessary component that interacts with two positively charged conserved amino acid residues in the third and seventh transmembrane helices of the LPA receptors (Wang et al., 2001). The hydrophobic tail interacts with a pocket of hydrophobic residues in the transmembrane regions of the receptors, significantly contributing to the ligand-receptor binding (Wang et al., 2001; Sardar et al., 2002).

Based on this model the inventors identified DGPP and dioctyl phosphatidic acid as selective $LPA_1$ and $LPA_3$ antagonists and FAPs as subtype selective agonists/antagonists of $LPA_{1-3}$ receptors (Fischer et al., 2001; Virag et al., 2003). Bandoh et al. (2000) showed that $LPA_3$ prefers unsaturated fatty acyl LPA species over saturated LPAs. Replacement of the phosphate with a phosphonate renders compounds metabolically stable against degradation by lipid phosphate phosphatases. Phosphonate modification also affects ligand-receptor interactions by reducing charge density on the polar head group. Phosphonate analogs of LPA have been studied recently and are less potent than LPA (Hooks et al., 2001; Xu et al., 2002). Alternatively, thiophosphate in place of phosphate yielded metabolically stable compounds with increased charge on the polar head group such as OMPT, a selective $LPA_3$ agonist (Hasegawa et al., 2003; Qian et al., 2003).

To explore the effects of these modifications along with the variations in the side chain in the FAP structure, the inventors synthesized a series of FAP analogs with an unsaturation at different positions in the sidechain (5a-f), thiophosphates (8a-g) and phosphonates (9ad, 11). These new analogs were evaluated as agonists and antagonists with respect to $LPA_{1-3}$. Saturated FAP analogs containing 10, 12 or 14 carbons (2a-c) were previously shown to be the most effective agonists and/or inhibitors at $LPA_{1-3}$ in the initial study (Virag et al., 2003). For this reason the inventors synthesized and characterized modified FAP analogs with these optimum chain lengths.

Each FAP analog was tested for the ability to induce $Ca^{2+}$ transients in RH7777 cells transfected with $LPA_{1-3}$ receptors (agonism), as well as the ability to inhibit LPA-induced $Ca^{2+}$ transients in the same cells (antagonism) (see Table 3). None of the compounds examined in this study induced intracellular $Ca^{2+}$ transients when applied up to a concentration of 30 µM in non-transfected RH7777 cells. The effects of unsaturation at different positions, modification of head group by phosphonate, difluoro phosphonate and thiophosphate with/without unsaturation on the activity of C-14 analogs at $LPA_{1-3}$ receptors are shown in FIG. 2. These modifications dramatically changed the pharmacological properties of FAPs on $LPA_{1-3}$ receptors. The mono-unsaturated FAP analogs (5a-e) showed a trend of increasing the potency and/or efficacy when compared to the saturated analogs, except C-10 analogs, without changing their ligand properties as agonists or antagonists at the $LPA_2$ and $LPA_3$ receptors (Table 3). The position of the double bond also had an impact on the activity. Comparison of the activities between decenyl regio isomers 5a and 5b, suggests that the $C_9$=$C_{10}$ double bond, as found in LPA 18:1, was preferred over $C_4$=$C_5$ in activating $LPA_2$ receptor ($EC_{50}$=3800 nM for 5a versus >10000 nM for 5b). Though 5b ($K_i$=370 nM) was moderately more active than 5a ($K_i$=504 nM), the preference for the double bond position was much less pronounced for inhibition of $LPA_3$ receptor.

Similarly, the $LPA_2$ receptor showed preference for $C_9$=$C_{10}$ unsaturation between the tetradecenyl isomers 5d ($EC_{50}$=397 nM) and 5e ($EC_{50}$=4100 nM), and $LPA_3$ showed no significant preference for double bond position. In contrast, $LPA_1$ preferred $C_{11}$=$C_{12}$ over $C_9$=$C_{10}$ between 5d ($K_i$=1146 nM) and 5e ($K_i$=457 nM), indicating the possibility of a differential conformational requirement in the side chain for each of the three LPA receptors (FIG. 2). In the unsaturated series, only tetradecenyl compounds (5d, 5e) antagonized the LPA response at $LPA_1$ receptor. This further supports our belief that the length of the side chain is critical for interaction with LPA receptors.

The replacement of phosphate with a thiophosphate as the headgroup in 10-, 12-, and 14-carbon saturated FAP analogs (8a-c) had a major impact on their agonist/antagonist properties at all three LPA receptor subtypes. At $LPA_1$, the thiophosphate modification completely abolished the inhibitory effects of the original FAP analogs. At $LPA_2$ on the other hand, the thiophosphate invariably increased the efficacy of the original FAP to 100%. At the $LPA_3$ receptor, the saturated thiophosphate FAP analogs consistently showed improved inhibition of the LPA response compared to the original FAPs. Dodecyl-thiophosphate (8b) is the most potent agonist and antagonist in the saturated thiophosphate analogs at $LPA_2$ ($EC_{50}$=1000 nM) and $LPA_3$ ($K_i$=14 nM), respectively. These results are consistent with our two-point contact model as the increase in the charge density, influenced by the properties of the hydrophobic tail, increased the agonist or antagonist properties of the FAP.

Next, we investigated the effect of combining a thiophosphate headgroup with mono-unsaturation ($C_9\!=\!C_{10}$) in the side chain. The combination of the thiophosphate headgroup with $C_9\!=\!C_{10}$ unsaturation resulted in analogs (8d-8f) with agonist/antagonist properties that were the combined properties of the saturated thiophosphates and unsaturated FAPs substantially lowering the $EC_{50}$ and $IC_{50}$ values. Similar to the saturated thio analogs, compounds 8d-8f were inactive at $LPA_1$ receptor. When the effects of saturated and unsaturated $C_{12}$, $C_{14}$ thiophosphates at $LPA_2$ and $LPA_3$ are compared, there is an increase in potency with the unsaturated analogs at $LPA_2$ with a minimal change in the potency at $LPA_3$ receptor. The tetradec-9-enyl thiophosphate (8f) compound needs to be discussed separately. It has retained the features of the saturated thio analogs at $LPA_1$, as it had no effect on the LPA-induced $Ca^{2+}$ mobilization. On the other hand, at 8f was found to be the best agonist at $LPA_2$ ($EC_{50}$=480 nM) and most potent antagonist at $LPA_3$ ($K_i$=14 nM) among all C-10, -12, and -14 thiophosphate analogs (FIGS. 2B and 2D). Dodec-9-enyl analog (8e) was an equipotent antagonist as 8f at the $LPA_3$ receptor. These differences in the effects of the thiophosphate analogs at the LPA receptor subtypes may provide us with a practical advantage in developing future subtype-selective agonists and antagonists, as short-chain thiophosphates interact selectively with $LPA_2$ and $LPA_3$ receptors.

Oleoyl-phosphate (5f), an unsaturated FAP analog of oleoly-LPA, did not inhibit nor did it activate $Ca^{2+}$ mobilization in cells expressing $LPA_{1-3}$. However, it potentiated LPA response at all three LPA receptors when the two compounds were co-applied. This observation led us to the hypothesis that by increasing the charge density of the 5f headgroup by replacing the phosphate with a thiophosphate, we may increase the binding of this compound to the receptors that is essential to turn this analog into an agonist. To test this hypothesis, we synthesized and evaluated the oleoylthiophosphate (8 g) at $LPA_{1-3}$ receptors. In agreement with our prediction, compound 8g was a partial agonist at $LPA_1$ ($EC_{50}$ ($E_{max}$)=193 nM (80%)), and $LPA_3$ ($EC_{50}$ ($E_{max}$)=546 nM (78%)), and a potent and full agonist at $LPA_2$ with the $EC_{50}$ of 244 nM ($E_{max}$=175% of LPA response), lower than that of oleoyl-LPA ($EC_{50}$=300 nM). The dose responses of 8 g, comparing its effects with LPA 18:1 at $LPA_{1-3}$ receptors, are shown in FIG. 3.

The phosphonate analogs (9a-d) were weaker inhibitors and agonists at the LPA receptors than their phosphate counterparts, consistent with data reported previously (Hooks et al., "Lysophosphatidic Acid-Induced Mitogenesis Is Regulated by Lipid Phosphate Phosphatases and Is Edg-Receptor Independent," *J. Biol. Chem.* 276:4611-4621 (2001)). However, tetradecyl-phosphonate (9c) inhibited LPA-induced $Ca^{2+}$ mobilization at all three receptor subtypes with $IC_{50}$ values in the micromolar range, thus becoming the first pan antagonist of the EDG family LPA receptors (FIG. 2). The importance of this finding is twofold. Compound 9c is the only known inhibitor of the $LPA_2$ receptor subtype apart from Ki16425 that exerts only a modest and partial inhibition (Ohta et al., 2003). Compound 9c, with a simpler structure and phosphonate headgroup, is presumably resistant to degradation by lipid phosphate phosphatases. These features make this molecule a good lead structure for further development of pan-antagonists for the $LPA_{1-3}$ receptors. We synthesized compound II, a difluorophosphonate analog of compound 9c, with an isosteric replacement of phosphonate by difluorophosphonate and tested at $LPA_{1-3}$ receptors. This compound retains the metabolic stability against phosphatases and at the same time increases the acidity of the phosphonate group, which presumably increases the binding to the receptor. Increase in the acidity of phosphonate group by the two fluorine atoms in compound II reversed the compound from an antagonist to a weak and partial agonist with an $EC_{50}$ of 10 μM ($E_{max}$=40%) at $LPA_2$ receptor. Compound II showed improved antagonistic activity at $LPA_3$ ($K_i$=575 nM) compared to 9c ($K_i$=1120 nM), while it showed partial antagonism ($\approx K_i$=788 nM; 40% inhibition of LPA response) at $LPA_1$.

LPA was shown to activate mitogenic and motogenic signaling in PC-3 cells (Kue et al., 2002). RT-PCR analysis of PC-3 cells, an androgen-independent human prostate cancer cell line, showed expression of transcripts encoding all three LPA receptors (Daaka et al., 2002). We tested the FAP analogs in PC-3 cells, which unlike the transfected RH7777 cells endogenously express $LPA_{1-3}$ receptors. Since PC-3 cells express $LPA_{1-3}$ receptors, the effects shown by the FAP compounds (Table 3) represent the combination of the effects of these compounds at the three LPA receptors. These experiments confirmed the pharmacological properties of the FAP analogs obtained from RH7777 cells expressing each LPA receptor individually. Thiophosphate analogs (8e and 8f) showed both independent activation and inhibition of LPA-induced $Ca^{2+}$ transients in PC-3 cells as they have different effects at each of the $LPA_{1-3}$ receptors. Oleoyl-thiophosphate (8 g) showed a maximal response of 30% of maximal LPA response, with no inhibition of LPA response, consistent with data from transfected RH7777 cells. Similarly the inhibitory activity shown by other compounds (Table 3) is a combination of effects of these compounds at individual $LPA_{1-3}$ receptors. The consistency of the results obtained from PC-3 cells that endogenously express LPA receptors with those results obtained using transfected RH7777 cells validates our assay systems.

To compare the effects of these FAP analogs at LPA receptors with the other available agonists and antagonists, we tested DGPP 8:0, Ki16425, N-acyl serine phosphoric acid (Ser-PA), N-acyl tyrosine phosphoric acid (Tyr-PA), and VPC12249 in our RH7777 cell system. This comparison, where a single test system is used for all compounds, has the benefit of providing us with reliable information on the relative effectiveness of these compounds despite the inherent shortcomings the individual test systems may have. Our results were consistent with previously published data for DGPP 8:0, Ser-PA and Ki16425, however we encountered differences for Tyr-PA, and VPC12249 (Table 3). DGPP 8:0 was identified in our lab as a subtype-selective inhibitor for $LPA_3$ and $LPA_1$, with $K_i$ values of 106 nM and 6.6 µM, respectively (Fischer et al., 2001). In order to test our high throughput test system we evaluated the effects of DGPP 8:0 in the same stably transfected RH7777 cell lines. The $K_i$ values were 202 nM for $LPA_3$ and 4.3 µM for $LPA_1$ (Table 3). These results convincingly showed the reproducibility of the DGPP results, even after the modification of the original assay method. Ki16425 was synthesized and identified as a subtype-selective antagonist for $LPA_1$ and $LPA_3$ with a very weak inhibitory effect on $LPA_2$ with $K_i$ values 250 nM, 360 nM, and 5.6 µM, respectively, using GTPγS loading assay in HEK293T cells transfected with LPA receptors (Ohta et al., 2003). When this compound was tested in our high throughput intracellular $Ca^{2+}$ monitoring system, we obtained similar $K_i$ values for $LPA_1$ (425 nM) and $LPA_3$ (148 nM), however Ki16425 seemed to inhibit $LPA_3$ slightly better compared to $LPA_1$ (Table 3). N-acyl serine phosphoric acid and N-acyl tyrosine phosphoric acid were originally identified as inhibitors of LPA-induced platelet aggregation (Sugiura et al., 1994) and inhibitors of the LPA induced Cl⁻ current in *Xenopus* oocytes (Liliom et al., 1996). In a mammalian cell line, however, Ser-PA was found to be an LPA-like agonist (Hooks et al., 1998). It was also shown to be an agonist at $LPA_1$ and $LPA_2$ when these receptor subtypes were heterologously expressed in TAg-Jurkat T-cells (An et al., 1998b). In our experiments Ser-PA was a full agonist at $LPA_1$ ($EC_{50}$=1.85 µM), but only a weak agonist at $LPA_2$. At $LPA_3$, Ser-PA was also a weak but full agonist with an $EC_{50}$ value of 1.6 µM (Table 3).

An et al. (1998b) showed that Tyr-PA did not affect LPA signaling at $LPA_1$ and $LPA_2$ receptors when applied at a concentration of 1 µM. Tyr-PA in our experiments had no effect on $LPA_1$, however it was found to be a weak agonist at $LPA_2$ ($EC_{50}$=11 µM) and an inhibitor at $LPA_3$ ($K_i$=2.3 µM) as shown in Table 3. VPC12249 is a 2-substituted analog of the N-acyl ethanolamide phosphate that was identified as a subtype-selective inhibitor of the $LPA_1$ and $LPA_3$ receptors, using a GTPγS-loading assay with cell membranes isolated from HEK293T cells expressing $LPA_1$, $LPA_2$, or $LPA_3$. VPC12249 was a better antagonist at $LPA_1$ ($K_i$=137 nM) than at $LPA_3$ ($K_i$=428 nM) (Heise et al. 2001). In our experiments however VPC12249 was only a weak inhibitor at $LPA_1$ and a better inhibitor at $LPA_3$ with a $K_i$ value of 588 nM (Table 3). This value is reasonably close to the published data in addition to the observation that VPC12249 did not affect LPA signaling through $LPA_2$ (Table 3). Analogous to the FAPs, these compounds also showed effects that are combination of effects at three LPA receptors on PC-3 cells, further validating our assay system.

In addition to its plasma membrane receptors, LPA was shown to be an agonist of the nuclear transcription factor PPARγ (McIntyre et al., 2003). Many agents have been reported to activate PPARγ, including thiazolidinedione family represented by Rosiglitazone, oxidized phospholipids, fatty acids, eicosanoids, and oxidized LDL. Zhang et al showed that unsaturated and alkyl ether analogs of LPA, 1,1-difluorodeoxy-(2R)-palmitoyl-sn-glycero-3-phosphate, its mono-fluoro analog 1-palmitoyl-(2R)-fluorodeoxy-sn-glycero-3-phosphate, and the oxidized phosphatidylcholine 1-O-hexadecyl-2-azeleoyl-phosphatidylcholine induced neointima formation, an early step leading to the development of atherogenic plaques, through PPARγ activation (Zhang et al., 2004).

The SAR of neointima formation by LPA analogs in vivo was identical to PPARγ activation in vitro and different from LPA G-protein coupled receptors (Zhang et al., 2004). We tested selected compounds including FAP-12 (2b), unsaturated thiophosphate analogs (8d-g), tetradecylphosphonate 9c, previously reported $LPA_1/LPA_3$ antagonists DGPP, Ki16425, VPC12249, and thiophosphate analog OMPT, a selective $LPA_3$ agonist, for PPARγ activation in vitro in CV1 cells using the PPRE-Acox-Rluc reporter gene assay. Interestingly, results from this assay (FIG. 4) indicate that along with previously reported agonists (OMPT) and antagonists (DGPP, Ki16425, VPC12249) FAP analogs, which have $LPA_{1-3}$ agonist/antagonist activities, can activate PPRE-Acox-Rluc reporter. These results are consistent with previously reported results (Zhang et al., 2004) in that LPA GPCR ligands can activate PPARγ. However, the results also emphasize that the SAR of PPARγ activation is different from GPCRs.

The present study extended the validity of our previously described two-point contact model as the minimal requirement to elicit specific interactions with LPA GPCRs, and provides further refinement of the minimal pharmacophore FAP by identifying modifications that allowed the synthesis of a pan-agonist and a pan-antagonist and several subtype-selective ligands. A systematic SAR study of the FAP pharmacophore with phosphonate, thiophosphate and introduction of unsaturation in the side chain outlined important principles for the design of subtype-selective LPA receptor agonists and antagonists. The results of the FAP analogs, and previously reported LPA agonists and antagonists by other groups, obtained from transfected RH7777 cells expressing each LPA receptor individually were consistent with results obtained from PC-3 cells that endogenously express $LPA_{1-3}$ receptors. In addition to their ligand properties on LPA GPCR, we showed that FAPs also activate nuclear transcription factor PPARγ with an SAR different from LPA GPCR. Based on the principles that emerged from SAR of FAP-12, oleoyl-thiophosphate (8 g) was synthesized and identified as a novel pan-agonist at all three LPA receptors confirming the previously predicted necessity for an $LPA_{1-3}$ agonist to possess both appropriate charge and side chain (length and unsaturation). Tetradecyl-phosphonate (9c) was identified as a metabolically stable first pan-antagonist that could serve as a lead structure for further development of $LPA_{1-3}$ receptor antagonists that are not sensitive to degradation by lipid phosphate phosphatases. Our results provide the first comprehensive evaluation of LPA-GPCR ligands as agonists of PPARγ. It was an unexpected surprise that with the exception of VPC12249 all other analogs, regardless of their agonist or antagonist activity on LPA GPCR, were agonists of PPARγ.

TABLE 3

Effects of FAP analogs 5a-f, 8a-g, 9a-d and 11 on LPA$_{1-3}$ transfected
RH7777 cells and comparison of the activities with the previously reported compounds $$R-X-\overset{\overset{Y}{\|}}{\underset{\underset{OH}{|}}{P}}-OH$$

| Cmp | X | Y | R | LPA$_1$ EC$_{50}$ (E$_{max}$) nM | LPA$_1$ IC$_{50}$ (K$_i$) nM | LPA$_2$ EC$_{50}$ (E$_{max}$) nM | LPA$_2$ IC$_{50}$ (K$_i$) nM | LPA$_3$ EC$_{50}$ (E$_{max}$) nM | LPA$_3$ IC$_{50}$ (K$_i$) nM | PC-3 EC$_{50}$ (E$_{max}$) nM | PC-3 IC$_{50}$ (K$_i$) nM |
|---|---|---|---|---|---|---|---|---|---|---|---|
| 2a[b] | O | O | —(CH$_2$)$_9$CH$_3$ | NE[c] | NE | 1800 (82) | NE | NE | 384 (121) | ND[d] | ND |
| 2b[b] | O | O | —(CH$_2$)$_{11}$CH$_3$ | NE | 2800 (1354) | 3100 (50) | NE | NE | 128 (61) | ND | ND |
| 2c[b] | O | O | —(CH$_2$)$_{13}$CH$_3$ | NE | 2300 (1081) | NE | NE | NE | 422 (211) | ND | ND |
| 5a | O | O | —(CH$_2$)$_8$CH=CH$_2$ | NE | >10000 | 3800 (100) | NE | NE | 770 (504) | NA[e] | 1510 (574) |
| 5b | O | O | —(CH$_2$)$_3$CH=CH(CH$_2$)$_4$CH$_3$ | NE | >10000 | >10000 | NE | NE | 830 (370) | NA | 1300 (735) |
| 5c | O | O | —(CH$_2$)$_8$CH=CHCH$_2$CH$_3$ | NE | >10000 | 717 (78) | NE | NE | 32 (27) | NA | 916 (390) |
| 5d | O | O | —(CH2)$_8$CH=CH(CH$_2$)$_3$CH$_3$ | NE | 3000 (1146) | 397 (58) | NE | NE | 96 (58) | NA | 241 (123) |
| 5e | O | O | —(CH$_2$)$_{10}$CH=CHCH$_2$CH$_3$ | NE | 2200 (457) | 4100 (75) | NE | NE | 103 (40) | ND | ND |
| 5f | O | O | —(CH$_2$)$_8$CH=CH(CH$_2$)$_7$CH$_3$ | NE | NE | NE | NE | NE | NE | —(11) | NA |
| 8a | O | S | —(CH$_2$)$_9$CH$_3$ | NE | NE | 4570 (100) | NE | NE | 122 (49) | NA | 1220 (521) |
| 8b | O | S | —(CH$_2$)$_{11}$CH$_3$ | NE | NE | 1000 (100) | NE | NE | 28 (14) | NA | 2838 (1300) |
| 8c | O | S | —(CH$_2$)$_{13}$CH$_3$ | NE | NE | 2500 (100) | NE | NE | 162 (76) | NE | NE |
| 8d | O | S | —(CH$_2$)$_8$CH=CH$_2$ | NE | NE | >10000 (56) | NE | NE | 340 (128) | NA | 1000 (533) |
| 8e | O | S | —(CH$_2$)$_8$CH=CHCH$_3$ | NE | NE | 677 (100) | NE | NE | 27 (14) | —(27) | 2972 (1460) |
| 8f | O | S | —(CH$_2$)$_8$CH=CH(CH$_2$)$_3$CH$_3$ | NE | NE | 480 (150) | NE | NE | 28 (14) | —(40) | 938 (397) |
| 8g | O | S | —(CH$_2$)$_8$CH=CH(CH$_2$)$_7$CH$_3$ | 193 (80) | NE | 244 (175) | NE | 546 (78) | NE | —(30) | NA |
| 9a | CH$_2$ | O | —(CH$_2$)$_8$CH$_3$ | NE | NE | NE | NE | NE | 1200 (68) | NA | 3122 (1500) |
| 9b | CH$_2$ | O | —(CH$_2$)$_{10}$CH$_3$ | NE | NE | NE | NE | NE | 654 (303) | NA | 2638 (1270) |
| 9c | CH$_2$ | O | —(CH$_2$)$_{12}$CH$_3$ | NE | ~10000 | NE | 5500 (3550) | NE | 3100 (1120) | NA | 9674 (4620) |
| 9d | CH$_2$ | O | —(CH$_2$)$_{16}$CH$_3$ | NE | NE | NE | NE | NE | NE | NE | NE |
| 11 | CF$_2$ | O | —(CH$_2$)$_{13}$CH$_3$ | NE | 2500 (788)[f] | ~10000 (40) | NE | NE | 1513 (575) | ND | ND |
| DGPP[g] | | | | NE | 5500 (4300) | NE | NE | NE | 454 (202) | ND | ND |
| Ki16425[h] | | | | NE | 762 (425) | NE | NE | NE | 301 (148) | NA | 3384 (1740) |
| Ser-PA | | | | 1850 (100) | NE | >10000 | NE | 1600 (100) | NE | —(42) | NA |
| Tyr-PA | | | | NE | NE | ~11000 | NE | NE | 5570 (2325) | —(25) | WA[i] |
| VPC12249[j] | | | | NE | WA | NE | NE | NE | 1186 (588) | NA | WA |

[a]E$_{max}$ = maximal efficacy of the drug/maximal efficacy of LPA 18:1, expressed as the percentage.
[b]Previously reported in Virag et al. (2003).
[c]NE = no effect was shown at the highest concentration (30 µM) tested.
[d]ND = not determined.
[e]NA = not applicable.
[f]Partial antagonist with 40% inhibition of the LPA response.
[g]Reported Ki values of DGPP are 106 nM and 6.6 µM at LPA3 and LPA1, respectively (Hasegawa et al., 2003).
[h]Reported Ki values of Ki16425 are 250 nM, 360 nM and 5.6 µM at LPA1, LPA3 and LPA2, respectively (Virag et al., 2003).
[i]WA = weak antagonist.
[j]Reported Ki values of VPC12249 are 137 nM and 428 nM at LPA1 and LPA3, respectively (Ohta et al., 2003).

Example 8

In vitro Evaluation of Compound 8 g For Protection of Intestinal Epithelial Cells Against Radiation or Chemotherapy Induced Apoptosis The experimental procedure utilized was substantially the same as that reported in Deng et al. (2002) and Deng et al., (2003).

Basically, IEC-6 cells were grown in DMEM medium supplemented with 5% fetal bovine serum, insulin (10 µg/ml), gentamycin sulfate (50 µg/ml), and incubated at 37° C. in a humidified 90% air-10% CO$_2$ atmosphere. Medium was changed every other day. Sub-confluent cells were washed twice and replaced by DMEM without serum the night before experiments.

Damage and IEC-6 cell apoptosis was induced via either γ-irradiation or chemotherapy. 20 Gy single dose of [$^{137}$Cs] source γ-irradiation was used in all experiments. Serum starved IEC-6 cells were pretreated with LPA, FAP12, or compound 8 g (FAP 18:1d9) for 15 minutes and then irradiated with a Mark I Model 25 Gamma Irradiator (J. L. Shepherd & Associate, San Fernando, Calif.) at a rate of 416 R/min for 4.81 minutes on a rotating platform. In some experiments, LPA was added at different times before or after irradiation. Treatment with 20 µM camptothecin of IEC-6 cells induces DNA fragmentation as measured by the ELISA assay at 16 h after treatment. DNA fragmentation was quantified using the Cell Death Detection ELISA kit from Boehringer (Indianapolis, Ind.) according to the instructions of the manufacturer. Samples were run in triplicate. A duplicate of the sample was used to quantify protein concentration using the BCA kit from Pierce (Rockford, Ill.). DNA fragmentation was expressed as absorbance units per µg protein per minute.

Figure 5:
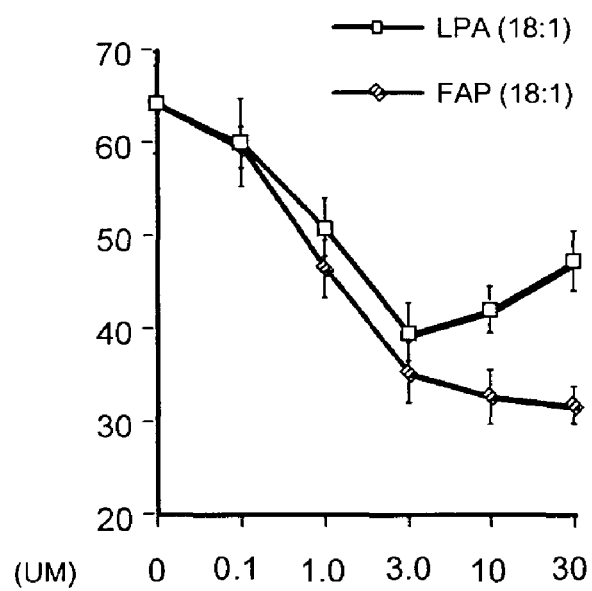
FIG. 5 is a graph illustrating LPA and FAP18:1d9 thiophosphate (8 g) dose-dependently inhibit DNA fragmentation induced by Campothotecin (20 μM).

LPA and FAP 12 (both 10 µM) inhibited Campthotecin-induced (20 µM) DNA fragmentation in IEC-6 cells. The effect of FAPs is dose dependent as illustrated for FAP 18:1d9 thiophosphate (8 g) in FIG. 5 and is comparable to that of LPA but supersedes it at concentrations above 3 µM.

Example 9

In vivo Evaluation of Compound 8g for Protection of Intestinal Epithelial Cells Against Radiation or Chemotherapy Induced Apoptosis The experimental procedure utilized was substantially the same as that reported in Deng et al. (2002).

The whole body irradiation (WBI) protocol has been reviewed and approved by the ACUC Committee of the University of Tennessee Health Sciences Center. ICR strain male mice (Harlan Laboratories, body weight 30-33 g) on a 12 h light/dark cycle and otherwise maintained on a standard laboratory chow ad libitum were starved for 16 h prior to treatment. WBI was done with a 12 Gy or 15 Gy dose using $Cs^{137}$ source at a dose rate of 1.9 Gy per minute. Groups of four mice received either 250 µl of 1 mM LPA complexed with 100 µM BSA dissolved in Hanks basal salt solution or the BSA vehicle alone 2 h prior to irradiation.

For detection of the apoptotic bodies, mice were euthanized with carbon dioxide inhalation 4 h after irradiation and the small intestine was dissected and fixed in neutral phosphate buffered isotonic 10% formalin. Four ~3- to 4-mm long segments from the small intestine were embedded in paraffin, 5 µM thick sections were cut and stained with hematoxylin and eosin. The number of surviving crypts was counted 3.5 days after irradiation.

Figure 6:
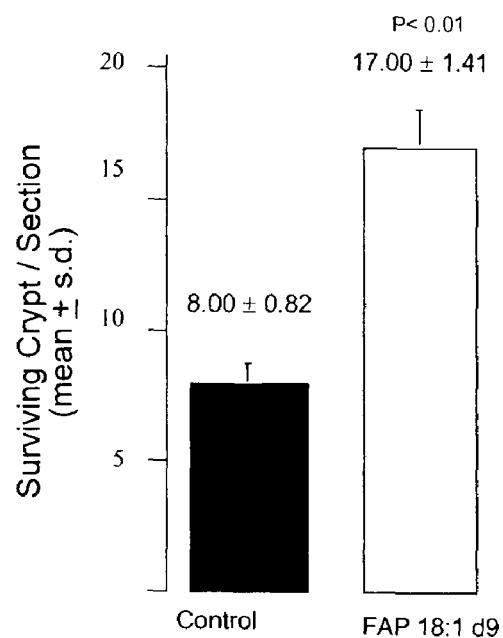
FIG. 6 is a graph illustrating that FAP 18:1d9 thiophosphate (8 g) enhances crypt survival.
Figure 7:
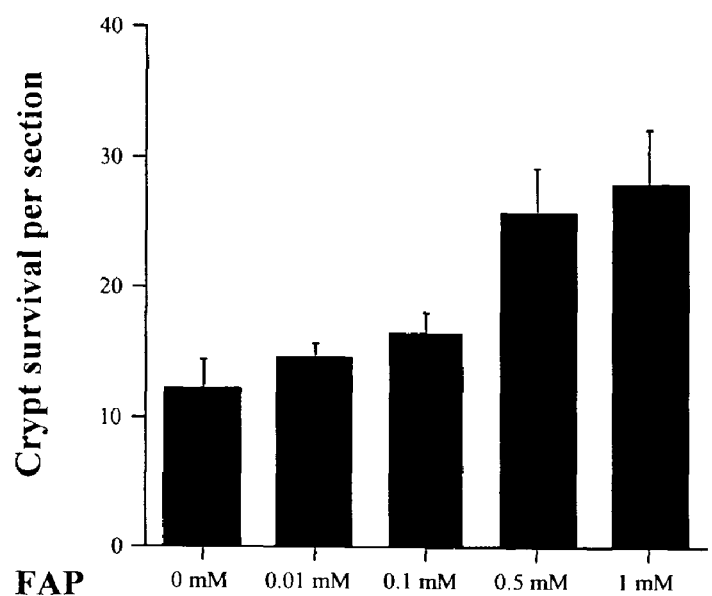
FIG. 7 is a graph illustrating the dose-dependent enhancement of crypt survival in FAP 18:1d9-treated mice.
Figure 8:
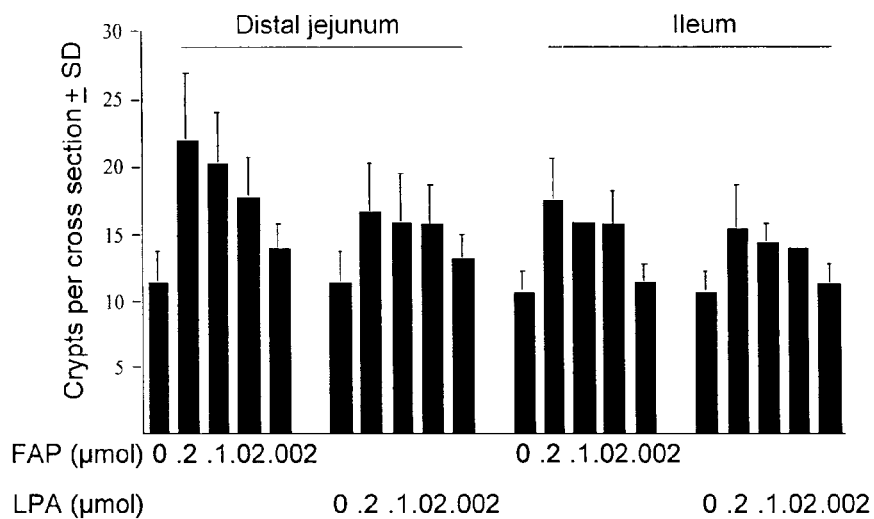
FIG. 8 is a graph demonstrating that FAP 18:1d9 elicits dose-dependent crypt survival in the ileum and jejunum of γ-irradiated mice.
Figure 9:
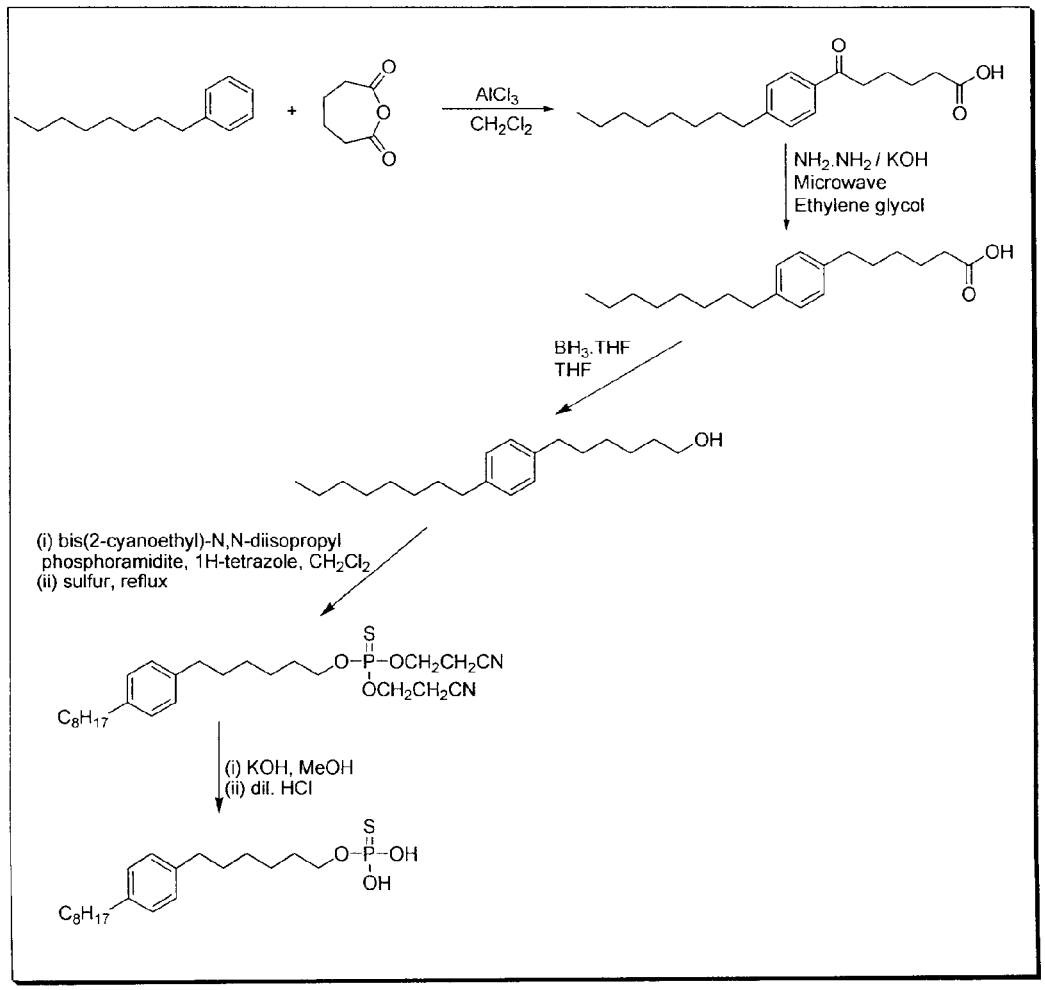
FIG. 9 illustrates a synthesis scheme for preparing thiophosphoric acid esters containing an arylalkyl $R^1$ group when $Y^1$ is also an alkyl.

FAP 18:1d9 (200 µM into the stomach 2 h prior irradiation) significantly (P>0.01) enhanced crypt survival in the irradiated animals (FIG. 6). The effect of FAP was dose-dependent (FIG. 7). The effect of FAP 18:1d9 was present in the jejunum and ileum and exceeded that of LPA (FIG. 8).

List Of References

Ahn et al., "Src-mediated tyrosine phosphorylation of dynamin is required for beta2-adrenergic receptor internalization and mitogen-activated protein kinase signaling," *J. Biol. Chem.* 274:1185-1188 (1999).

An et al., "Identification of cDNAs encoding two G protein-coupled receptors for lysosphingolipids," *FEBS. Lett.* 417:279-282 (1997a).

An et al., "Molecular cloning of the human Edg2 protein and its identification as a functional cellular receptor for lysophosphatidic acid," *Biochem. Biophys. Res. Commun.*, 231 (3):619-622 (1997b).

An et al., "Characterization of a novel subtype of human G protein-coupled receptor for lysophosphatidic acid," *J. Biol. Chem.* 273:7906-7910 (1998a).

An et al., "Recombinant human G protein-coupled lysophosphatidic acid receptors mediate intracellular calcium mobilization," *Mol. Pharmacol.* 54:881-888 (1998b).

Balazs et al., "Topical application of LPA accelerates wound healing," *Ann. N.Y. Acad. Sci.* 905:270-273 (2000).

Balboa et al., "Proinflammatory macrophage-activating properties of the novel phospholipid diacylglycerol pyrophosphate," *J. Biol. Chem.* 274:522-526 (1999).

Balsinde et al., "Group IV cytosolic phospholipase A2 activation by diacylglycerol pyrophosphate in murine P388D1 macrophages," *Ann. NY Acad. Sci.* 905:11-15 (2000).

Bandoh et al., "Molecular cloning and characterization of a novel human G-protein-coupled receptor, EDG7, for lysophosphatidic acid," *J. Biol. Chem.* 274:27776-27785 (1999).

Bandoh et al., "Lysophosphatidic acid (LPA) receptors of the EDG family are differentially activated by LPA species; Structure-activity relationship of cloned LPA receptors," *FEBS Lett.* 478: 159-165 (2000).

Bishop and Bell, "Assembly of phospholipids into cellular membranes: biosynthesis, transmembrane movement and intracellular translocation," *Annu. Rev. Cell Biol.* 4:579-610 (1988).

Bittman et al., "Inhibitors of lipid phosphatidate receptors: N-palmitoyl-serine and N-palmitoyl-tyrosine phosphoric acids," *J. Lipid Res.* 37:391-398 (1996).

Bosch, "Phosphoglyceride metabolism," *Annu. Rev. Biochem.* 43:243-277 (1974).

Cherrick et al., "Effects of topically applied 5-fluorouracil in the Syrian hamster," *J. Invest. Dermatol.*, 63:284-286 (1974).

Cunnick et al., "Role of tyrosine kinase activity of epidermal growth factor receptor in the lysophosphatidic acid-stimulated mitogen-activated protein kinase pathway," *J. Biol. Chem.* 273:14468-14475 (1998).

Daaka et al., "Mitogenic Action of LPA in Prostate," *Biochim. Biophys. Acta* 1582:265-269 (2002).

Deng et al., "Lysophosphatidic acid protects and rescues intestinal epithelial cells from radiation- and chemotherapy-induced apoptosis," *Gastroenterology*, 123 (1): 206-16 (2002).

Deng et al., "LPA protects intestinal epithelial cells from apoptosis by inhibiting the mitochondrial pathway," *Am. J. Physiol. Gastrointest. Liver Physiol.* 284 (5): G821-9 (2003).

Durieux et al., "Lysophosphatidic acid induces a pertussis toxin-sensitive Ca activated Cl⁻ current in *Xenopus laevis* oocytes," *Am. J. Physiol.* 263:896-900 (1992).

Dyer et al., "The effect of serum albumin on PC12 cells: I. Neurite retraction and activation of the phosphoinositide second messenger system," *Mol. Brain. Res.* 14:293-301 (1992).

Eicholtz et al., "The bioactive phospholipid lysophosphatidic acid is released from activated platelets," *Biochem. J.* 291:677-680 (1993).

Fernhout et al., "Lysophosphatidic acid induces inward currents in *Xenopus laevis* oocytes; evidence for an extracellular site of action," *European Journal of Pharmacology* 213: 313-315 (1992).

Fischer et al., "Naturally occurring analogs of lysophosphatidic acid elicit different cellular responses through selective activation of multiple receptor subtypes," *Mol. Pharmacol.* 54:979-988 (1998).

Fischer et al., "Short-Chain Phosphatidates Are Subtype-Selective Antagonists of Lysophosphatidic Acid Receptors. *Mol. Pharmacol.* 60:776-784 (2001).

Fukami and Takenawa, "Phosphatidic acid that accumulates in platelet-derived growth factor-stimulated Balb/c 3T3 cells is a potential mitogenic signal," *J. Biol. Chem.* 267: 10988-10993 (1992).

Fukushima et al., "A single receptor encoded by vzg-1/1pA1/edg-2 couples to G proteins and mediates multiple cellular responses to lysophosphatidic acid," *Proc. Natl. Acad. Sci. USA* 95:6151-6 (1998).

Gerrard et al., "Lysophospatidic acids influence on platelet aggregation and intracellular calcium flux," *Am. J. Path.* 96:423-438 (1979).

Ghosh et al., "Lipid biochemistry: functions of glycerolipids and sphingolipids in cellular signaling," *Faseb. J.* 11:45-50 (1997).

Goetzl et al., "Lysophospholipid Growth Factors," in *Cytokine Reference* (Oppenheim, J, ed.), Academic Press, New York, 1407-1418 (2000).

Gohla et al., "The G-protein G13 but not G12 mediates signaling from lysophosphatidic acid receptor via epidermal growth factor receptor to Rho," *J. Biol. Chem.* 273:4653-4659 (1998).

Gonda et al., "The novel sphingosine 1-phosphate receptor AGR16 is coupled via pertussis toxin-sensitive and -insensitive G-proteins to multiple signaling pathways," *Biochem. J.* 337:67-75 (1999).

Guo et al., "Molecular cloning of a high-affinity receptor for the growth factor-like lipid mediator lysophosphatidic acid from *Xenopus* oocytes," *Proc. Natl. Acad. Sci. USA.* 93:14367-14372 (1996).

Halazy et al., "9-(Difluorophosphonoalkyl)- Guanines as a New Class of Multisubstrate Analogue Inhibitors of Purine Nulceoside Phosphorylase," *J. Am. Chem. Soc.* 113:315-317 (1991).

Haines et al. ("Synthesis of the Dipotassium Salts of Methyl .alpha.-DMannopyranoside 6-Phosphorothioate and D-Mannose 6-Phosphorothioate," *Synthesis* 12:1422-1424 (1996).

Hasegawa et al., "Identification of a Phosphothionate Analogue of Lysophosphatidic Acid (LPA) as a Selective Agonist of the $LPA_3$ Receptor," *J. Biol. Chem.* 278:11962-11969 (2003).

Hecht et al., "Ventricular zone gene-1 (vzg-1) encodes a lysophosphatidic acid receptor expressed in neurogenic regions of the developing cerebral cortex," *J. Cell. Biol.* 135: 1071-1083 (1996).

Heise et al., "Activity of 2-Substituted Lysophosphatidic Acid (LPA) Analogs at LPA Receptors: Discovery of a Lpa1/Lpa3 Receptor Antagonist," *Mol. Pharmacol.* 60:1173-1180 (2001).

Herrlich et al., "Ligand-independent activation of platelet-derived growth factor receptor is a necessary intermediate in lysophosphatidic, acid-stimulated mitogenic activity in 1 cells," *Proc. Natl. Acad. Sci. USA.* 95:8985-8990 (1998).

Hill et al., "The Rho family GTPases RhoA, Rac1, and CDC42Hs regulate transcriptional activation by SRF," *Cell* 81:1159-1170 (1995).

Hoffmann-Wellenhof et al., "Correlation of melanoma cell motility and invasion in vitro," *Melanoma. Res.* 5:311-319 (1995).

Hooks et al., "Characterization of a receptor subtype-selective lysophosphatidic acid mimetic," *Mol. Pharmacol.* 53:188-194 (1998).

Hooks et al., "Lysophosphatidic Acid-Induced Mitogenesis Is Regulated by Lipid Phosphate Phosphatases and Is Edg-Receptor Independent," *J. Biol. Chem.* 276:4611-4621 (2001).

Hunt and Goodson, In: *Current Surgical Diagnosis & Treatment* (Way, Appleton & Lange), pp. 86-98 (1988).

Im et al., "Molecular cloning and characterization of a lysophosphatidic acid receptor, Edg-7, expressed in prostate," *Mol. Pharmacol.* 57:753-759 (2000).

Imamura et al., "Serum requirement for in vitro invasion by tumor cells," *Jpn. J. Cancer Res.* 82:493-496 (1991).

Imamura et al., "Induction of in vitro tumor cell invasion of cellular monolayers by lysphosphatidic acid or phospholipase D," *Biochem. Biophys. Res. Com.* 193:497-503 (1993).

Imamura et al., "rho-Mediated protein tyrosine phosphorylation in lysophosphatidic-acid-induced tumor-cell invasion," *Int. J. Cancer* 65:627-632 (1996).

Jalink et al., "Lysophosphatidic acid, but not phosphatidic acid, is a potent $Ca^{2+}$-mobilizing stimulus for fibroblasts," *J. Biochem.* 265:12232-12239 (1990).

Jalink and Moolenaar, "Thrombin receptor activation causes rapid neural cell rounding and neurite retraction independent of classic second messengers," *J. Cell Biol.* 118:411-419 (1992).

Jalink et al., "Lysophosphatidic Acid is a Chemoattractant for Dictyostelium Discoideum Arnoebae," *Proc. Natl. Acad. Sci. USA.* 90:1857-1861 (1993a).

Jalink et al., "Lysophosphatidic acid induces neuronal shape changes via a novel, receptor-mediated signaling pathway: similarity to thrombin action," *Cell Growth Differ.* 4:247-255 (1993b).

Jalink et al., "Growth factor-like effects of lysophosphatidic acid, a novel lipid mediator," *Biochimica. et. Biophysica. Acta.* 1198:185-196 (1994a).

Jalink et al., "Inhibition of lysophosphatidate- and thrombin-induced neurite retraction and neuronal cell rounding by ADP ribosylation of the small GTP-binding protein Rho," *J. Cell Biol.* 126:801-810 (1994b).

Jalink et al., "Lysophosphatidic acid-induced $Ca^{2+}$ mobilization in human A431 cells: structure-activity analysis," *Biochem. J.* 307:609-616 (1995).

Kartha et al., "Adenine nucleotides stimulate migration in wounded cultures of kidney epithelial cells," *J. Clin. Invest.,* 90:288-292 (1992).

Kawasawa et al., "Brain-specific expression of novel G-protein-coupled receptors, with homologies to *Xenopus* PSP24 and human GPR45," *Biochem. Biophys. Res. Commun.,* 276 (3):952-956 (2000).

Kimura et al., "Effect of sphingosine and its N-methyl derivatives on oxidative burst, phagokinetic activity, and trans-endothelial migration of human neutrophils," *Biochem. Pharmacol.* 44:1585-1595 (1992).

Kimura et al., "Regulation of myosin phosphatase by Rho and Rho-associated kinase (Rho-kinase)," *Science* 273:245-248 (1996).

Kobayashi et al., "Existence of a Bioactive Lipid, Cyclic Phosphatidic Acid in Human Serum," *Life Sci.* 56:245-253 (1999).

Kue et al., "Lysophosphatidic Acid-Regulated Mitogenic Erk Signaling in Androgen-Insensitive Prostate Cancer Pc-3 Cells." *Int. J. Cancer* 102:572-579 (2002).

Liliom et al., "N-palmitoyl-serine and N-palmitoyl-tyrosine phosphoric acids are selective competitive antagonists of the lysophosphatidic acid receptors," *Mol. Pharmacol.* 50:616-623 (1996).

Liliom et al., "Identification of a novel growth factor-like lipid, 1-O-cis-alk-1'-enyl-2-lyso-sn-glycero-3-phospha-te (alkenyl-GP) that is present in commercial sphingolipid preparations," *J. Biol. Chem.* 273:13461-13468 (1998).

Lin et al., "Clathrin-mediated endocytosis of the beta-adrenergic receptor is regulated by phosphorylation/dephosphorylation of beta-arrestinl," *J. Biol. Chem.* 272:31051-31057 (1997).

Liotta et al., "Biochemical mechanisms of tumor invasion and metastasis," *Anticancer Drug Des.* 2:195-202 (1987).

Liu et al., "Synthesis, calcium mobilizing, and physicochemical properties of D-chiro-inositol 1,3,4,6-tetrakisphosphate, a novel and potent ligand at the D-myo-inositol 1,4,5-trisphosphate receptor," *J. Med. Chem.* 42:1991-1998 (1999).

Luttrell et al., "Beta-arrestin-dependent formation of beta2 adrenergic receptor-Src protein kinase complexes," *Science* 283:655-661 (1999).

Lynch et al., "Structure/activity relationships in lysophosphatidic acid: the 2-hydroxyl moiety," *Mol. Pharmacol.* 52:75-81 (1997).

Machesky and Hall, "Rho: a connection between membrane signaling and cytoskeleton," *Trends Cell Biol.* 6:304-310 (1996).

Macrae et al., "Cloning, characterization, and chromosomal localization of rec1.3, a member of the G-protein-coupled receptor family highly expressed in brain," *Brain Res. Mol. Brain. Res.* 42:245-254 (1996).

McIntyre et al., "Identification of an Intracellular Receptor for Lysophosphatidic Acid (LPA): LPA Is a Transcellular PPAR-gamma Agonist," *Proc. Natl. Acad. Sci. USA,* 100:131-136 (2003).

Mills et al., "A putative new growth factor in ascitic fluid from ovarian cancer patients: identification, characterization, and mechanism of action," *Cancer Res.* 48:1066-1071 (1988).

Mills et al., "Ascitic fluid from human ovarian cancer patients contains growth factors necessary for intraperitoneal growth of human ovarian adenocarcinoma cells," *J. Clin. Invest.* 86:851-855 (1990).

Miyata et al., "New wound-healing model using cultured corneal endothelial cells: Quantitative study of healing process," *Jpn. J. Opthalmol.,* 34:257-266 (1990).

Moolenaar, "G-protein-coupled receptors, phosphoinositide hydrolysis, and cell proliferation," *Cell Growth Differ.* 2:359-364 (1991).

Moolenaar, "A novel lipid mediator with diverse biological actions," *Trends in Cell Biology* 4:213-219 (1994).

Moolenar, "Lysophosphatidic acid, a multifunctional phospholipid messenger," *J. Biol. Chem.,* 270:12949-12952 (1996).

Moolenaar et al., "Lysophosphatidic acid: G-protein signalling and cellular responses," *Curr. Opin. Cell Biol.* 9:168-173 (1997).

Mukai et al., "Mechanism of tumor cell invasion studied by a culture model-modification of invasiveness by host mediators," *Hum. Cell* 6:194-198 (1993).

Muller et al., "Inhibitory action of transforming growth factor beta on endothelial cells," *Proc. Natl. Acad. Sci. USA* 84:5600-5604 (1987).

Munnik et al., "Identification of diacylglycerol pyrophosphate as a novel metabolic product of phosphatidic acid during G-protein activation in plants," *J. Biol. Chem.* 271:15708-15715 (1996).

Murakami-Murofushi et al., "Inhibition of cell proliferation by a unique lysophosphatidic acid, PHYLPA, isolated from *Physarum polycephalum*: signaling events of antiproliferative action by PHYLPA," *Cell Struct. Funct.* 18:363-370 (1993).

Myher et al., "Molecular species of glycerophospholipids and sphingomyelins of human plasma: comparison to red blood cells," *Lipids* 24:408-418 (1989).

Noguchi et al., "Identification of p2y$_9$/GPR23 as a Novel G Protein-coupled Receptor for Lysophosphatidic Acid, Structurally Distant from the Edg Family," *J. Biol. Chem.* 278(28):25600-25606 (2003).

Ohkawara et al., In: Biochemistry of Cutaneous Epithelial Differentiation, Seiji et al., eds., University Park Press, Baltimore, 1977, pp. 274-278.

Ohta et al., "Ki16425, a Subtype-Selective Antagonist for Edg-Family Lysophosphatidic Acid Receptors. *Mol. Pharmacol.* 64:994-1005 (2003).

Parrill et al., "Identification of edg1 receptor residues that recognize sphingosine 1-phosphate," *J. Biol. Chem.* 275:39379-393784 (2000).

Postma et al., "Sphingosine-1-phosphate rapidly induces Rho-dependent neurite retraction: action through a specific cell surface receptor," Embo. J. 15:2388-2392 (1996).

Qian et al., "Enantioselective Responses to a Phosphorothioate Analogue of Lysophosphatidic Acid with LPA$_3$ Receptor-Selective Agonist Activity," *J. Med. Chem.* 46:5575-5578 (2003).

Ridley, "Rho: theme and variations," *Curr. Biol.* 6:1256-1264 (1996).

Ridley and Hall, "The small GTP-binding protein rho regulates the assembly of focal adhesions and actin stress fibers in response to growth factors," *Cell* 70:389-399 (1992).

Sardar et al., "Molecular Basis for Lysophosphatidic Acid Receptor Antagonist Selectivity," *Biochim. Biophys. Acta* 1582:309-317 (2002).

Sato et al., "Autocrine activities of basic fibroblast growth factor: regulation of endothelial cell movement, plasminogen activator synthesis, and DNA synthesis," *J. Cell Biol.,* 107:1199-1205 (1988).

Schumacher et al., "Platelet aggregation evoked in vitro and in vivo by phosphatidic acids and lysodervatives: identity with substances in aged serum (DAS)," *Thrombos. Haemostas.* 42:631-640 (1979).

Simon et al., "Human platelet aggregation induced by 1-alkyl-lysophosphatidic acid and its analogs: a new group of phospholipid mediators?," *Biochem. Biophys. Res. Commun.* 108:1743-1750 (1982).

Spiegel and Milstien, "Functions of a new family of sphingosine-1-phosphate receptors," *Biochim. et. Biophys. Acta.* 1484:107-116 (2000).

Stenn et al., "Expression of the bc1-2 Protoocogene in the Cycling Adult Mouse Hair Follicle," *J. Invest. Dermatol.* 103:107-111 (1994).

Sugiura et al., "Biochemical characterization of the interaction of lipid phosphoric acids with human platelets: Comparison with platelet activating factor," *Arch. Biochem. Biophys.* 311:358-368 (1994).

Sun et al., "Synthesis of Chiral 1-(2'-Amino-2'-carboxyethyl)-1,4-dihydro-6,7-quinoxaline-2,3-diones: alpha.-amino-3-hydroxy-5-methyl-4-isoxazolepropionate Receptor Agonists and Antagonists," *J. Med. Chem.* 39:4430-4438 (1996).

Tigyi et al., "A serum factor that activates the phosphatidylinositol phosphate signaling system in *Xenopus* oocytes," *Proc. Natl. Acad. Sci. USA* 87:1521-1525 (1990).

Tigyi et al., "A factor that activates oscillatory chloride currents in *Xenopus* oocytes copurifies with a subfraction of serum albumin," *J. Biol. Chem.* 266:20602-20609 (1991).

Tigyi and Miledi, "Lysophosphatidates bound to serum albumin activate membrane currents in *Xenopus* oocytes and neurite retraction in PC12 pheochromocytoma cells," *J. Biol. Chem.* 267:21360-21367 (1992).

Tigyi et al., "Lysophosphatidic acid possesses dual action in cell proliferation," *Proc. Natl. Acad. Sci. USA.* 91:1908-1912 (1994).

Tigyi et al., "Lysophosphatidic acid-induced neurite retraction in PC12 cells: control by phosphoinositide-$Ca^{2+}$ signaling and Rho," *J. Neurochem.* 66:537-548 (1996).

Tigyi et al., "Pharmacological characterization of phospholipid growth factor receptors," *Ann. NY Acad. Sci.* 905: 34-53 (2000).

Tokumura et al., "Effects of synthetic and natural lysophosphatidic acid on the arterial blood pressure of different animal species," *Lipids* 13:572-574 (1978).

Tokumura et al., "Stimulatory effect of lysophosphatidic acids on uterine smooth muscles of non-pregnant rats," *Arch. Int. Pharmacodyn. Ther.* 245:74-83 (1980).

Tokumura et al., "Lysophosphatidic acid-induced aggregation of human and feline platelets: structure-activity relationship," *Biochem. Biophys. Res. Commun.* 99:391-398 (1981).

Tokumura et al., "Involvement of lysophospholipase D in the production of lysophosphatidic acid in rat plasma," *Biochim. et. Biophys. Acta.* 875:31-38 (1986).

Tokumura et al., "Lysophosphatidic acids induce proliferation of cultured vascular smooth muscle cells from rat aorta," *Am. J. Physiol.* 267:204-210 (1994).

Tokumura, "A family of phospholipid autacoids: occurrence, metabolism, and bioactions," *Prog. Lipid Res.* 34:151-184 (1995).

Umansky et al., "Prevention of rat neonatal cardiomyocyte apoptosis induced by stimulated in vitro ischemia and reperfusion," *Cell Death Diff.* 4:608-616 (1997).

van Brocklyn et al., "Dual actions of sphingosine-1-phosphate: extracellular through the Gi-coupled receptor Edg-1 and intracellular to regulate proliferation and survival," *J. Cell. Biol.* 142:229-240 (1998).

van Brocklyn et al., "Sphingosine-1-phosphate is a ligand for the G protein-coupled receptor EDG-6," *Blood* 95:2624-2629 (2000).

van Corven et al., "Lysophosphatidic-induced cell proliferation: identification and dissection of signaling pathways mediated by G proteins," *Cell* 59:45-54 (1989).

van Corven et al., "Mitogenic action of lysophosphatidic acid and phosphatidic acid on fibroblasts: Dependence on acyl-chain length and inhibition by suramin," *Biochem. J.* 281:163-169 (1992).

van der Bend et al., "The biologically active phospholipid, lysophosphatidic acid, induces phosphatidylcholine breakdown in fibroblasts via activation of phospholipase D: Comparison with the response to endothelin," *Biochem. J.* 285: 235-240 (1992a).

van der Bend et al., "Identification of a putative membrane receptor for the bioactive phospholipid, lysophosphatidic acid," *EMBO J.* 11:2495-2501 (1992b).

Verrier et al., "Wounding a fibroblast monolayer results in the rapid induction of the c-fos proto-oncogene," *EMBO J.,* 5:913-917 (1986).

Virag et al., "Fatty Alcohol Phosphates Are Subtype-Selective Agonists and Antagonists of Lysophosphatidic Acid Receptors," *Mol. Pharmacol.* 63:1032-1042 (2003).

Wang et al., "A Single Amino Acid Determines Lysophospholipid Specificity of the S1p1 (Edg1) and Lpa1 (Edg2) Phospholipid Growth Factor Receptors," *J. Biol. Chem.* 276: 49213-49220 (2001).

Wissing and Behrbohm, "Diacylglycerol pyrophosphate, a novel phospholipid compound," *FEBS Lett.* 315: 95-99 (1993).

Xu et al., "Characterization of an ovarian cancer activating factor in ascites from ovarian cancer patients," *Clin. Cancer Res.* 1:1223-1232 (1995a).

Xu et al., "Effect of lysophospholipids on signaling in the human Jurkat T cell line," *J. Cell. Physiol.,* 163:441-450 (1995b).

Xu et al., "Synthesis of Chiral (.alpha.,.alpha.-Difluoroalkyl)Phosphonate Analogues of (Lyso)Phosphatidic Acid Via Hydrolytic Kinetic Resolution. *Org. Lett.* 4:4021-4024 (2002).

Yatomi et al., "Sphingosine-1-phosphate: a platelet-activating sphingolipid released from agonist-stimulated human platelets," *Blood* 86:193-202 (1995).

Zhang et al., "Lysophosphatidic Acid Induces Neointimaformation through PPARγ Activation," *J. Exp. Med.* 199: 763-774 (2004).

Zhou et al., "Phosphatidic acid and lysophosphatidic acid induce haptotactic migration of human monocytes," *J. Biol. Chem.* 270:25549-25556 (1995).

Zsiros et al., "Naturally occurring inhibitors of lysophosphatidic acid," Abstr. 6th. International Congress on Platelet Activating Factor and Related Lipid Mediators, p. 128 (1998).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for protecting intestinal and hematopoietic cells of a mammalian subject from apoptosis caused by radiation exposure or chemotherapy, the method comprising administering to the subject a therapeutically effective amount of a composition comprising a compound of formula (I)

$$CQ^1—CH(X^3)—CQ^2$$
with $X^1$ and $X^2$ substituents wherein,
$X^1$ is $R^1$—$Y^1$-A-;
$X^2$ is —$Z^1$—P(S)(OH)$_2$;
$X^3$ is hydrogen;
A is a direct link or (CH$_2$)$_l$ with l being an integer from 1-30;
$Y^1$ is (CH$_2$)$_l$ with l being an integer from 1-30;
$Z^1$ is oxygen;
$Q^1$ and $Q^2$ are independently selected from the group consisting of two hydrogens, =NR$^4$, =O, and a combination of H and —NR$^5$R$^6$;
$R^1$ is independently a straight or branched-chain C$_1$ to C$_{30}$ alkyl, a straight or branched-chain C$_2$ to C$_{30}$ alkenyl, an aromatic or heteroaromatic ring (optionally substituted), an acyl, an arylalkyl, an aryloxyalkyl,

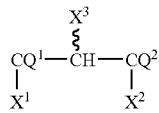

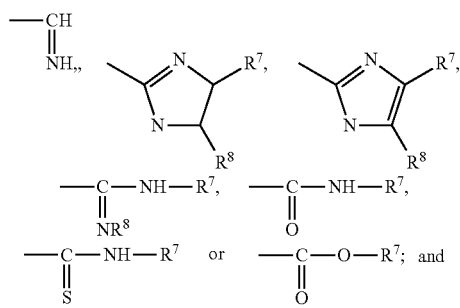

$R^4$, $R^5$, $R^6$, $R^7$, and $R^8$ are independently hydrogen, a straight or branched-chain C$_1$ to C$_{30}$ alkyl, a straight or branched-chain C$_2$ to C$_{30}$ alkenyl, an aromatic or heteroaromatic ring with or without mono-, di-, or tri-substitutions of the ring, an acyl, an arylalkyl, or an aryloxyalkyl including straight or branched-chain C$_1$ to C$_{30}$ alkyl.

2. The method of claim 1 wherein $Q^1$ and $Q^2$ of compound (I) are each two hydrogen and $R^1$ is a straight or branched-chain C$_2$ to C$_{30}$ alkenyl.

3. The method of claim 1 wherein the composition comprises thiophosphoric acid O-octadec-9-enyl ester.

4. The method of claim 1 wherein the step of administering is performed via a method chosen from among the group consisting of oral, topical, transdermal, parenteral, subcutaneous, intravenous, intramuscular, intraperitoneal, intranasal, intracavitary, intravesicalar, intraocular, intraarterial, intralesional, or a combination thereof.

5. A method for treating chemotherapy-induced tissue damage in the intestine of a mammalian subject, the method comprising administering to the subject a composition comprising a compound of formula (I)

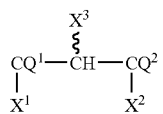

wherein,
$X^1$ is $R^1$—$Y^1$-A-;
$X^2$ is —$Z^1$—$P(S)(OH)_2$;
$X^3$ is hydrogen;
A is a direct link or $(CH_2)_l$ with l being an integer from 1-30;
$Y^1$ is $(CH_2)_l$ with l being an integer from 1-30;
$Z^1$ is oxygen;
$Q^1$ and $Q^2$ are independently selected from the group consisting of two hydrogens, =$NR^4$, =O, and a combination of H and —$NR^5R^6$;
$R^1$ is independently a straight or branched-chain $C_1$ to $C_{30}$ alkyl, a straight or branched-chain $C_2$ to $C_{30}$ alkenyl, an aromatic or heteroaromatic ring (optionally substituted), an acyl, an arylalkyl an aryloxyalkyl,

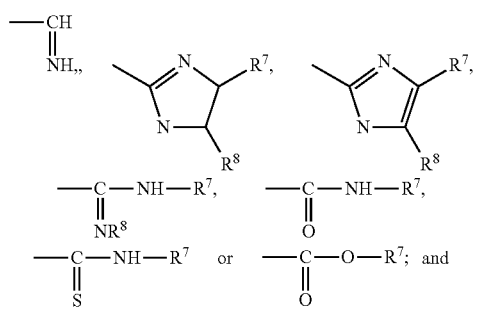

$R^4$, $R^5$, $R^6$, $R^7$, and $R^8$ are independently hydrogen, a straight or branched-chain $C_1$ to $C_{30}$ alkyl, a straight or branched-chain $C_2$ to $C_{30}$ alkenyl, an aromatic or heteroaromatic ring with or without mono-, di-, or tri-substitutions of the ring, an acyl, an arylalkyl including straight or branched-chain $C_1$ to $C_{30}$ alky, or an aryloxyalkyl.

6. The method of claim 5 wherein $Q^1$ and $Q^2$ of compound (I) are each two hydrogen and $R^1$ is a straight or branched-chain $C_2$ to $C_{30}$ alkenyl.

7. The method of claim 5 wherein the step of administering is performed via oral, parenteral, subcutaneous, intravenous, or intraperitoneal route.

* * * * *